(12) United States Patent
Warpeha et al.

(10) Patent No.: US 8,492,614 B2
(45) Date of Patent: Jul. 23, 2013

(54) PLANT BIOCHEMICAL SYSTEMS AND USES THEREOF

(75) Inventors: Katherine Warpeha, Chicago, IL (US); Lon Kaufman, Highland Park, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 692 days.

(21) Appl. No.: 12/528,780

(22) Filed: Aug. 26, 2009

(65) Prior Publication Data

US 2010/0257636 A1 Oct. 7, 2010

Related U.S. Application Data

(63) Continuation-in-part of application No. PCT/US2008/055036, filed on Feb. 26, 2008.

(60) Provisional application No. 60/975,513, filed on Sep. 26, 2007, provisional application No. 60/891,698, filed on Feb. 26, 2007, provisional application No. 61/096,533, filed on Sep. 12, 2008.

(51) Int. Cl.
*A01N 33/00* (2006.01)
*A01N 65/20* (2009.01)
*C07K 17/00* (2006.01)
*C12P 13/00* (2006.01)

(52) U.S. Cl.
USPC ........... 800/295; 435/108; 435/410; 435/415; 504/100; 800/298; 800/312

(58) Field of Classification Search
USPC ................ 435/108, 410; 504/100; 800/295
See application file for complete search history.

(56) References Cited

PUBLICATIONS

Rozema et al., Journal of Photochemistry and Photobiolgoy B: Biology 66:2-12, 2002.*
Warpeha et al., Plant Physiol., 140:844-855, 2006.*

* cited by examiner

*Primary Examiner* — Phuong Bui
(74) *Attorney, Agent, or Firm* — Michael Best & Friedrich LLP

(57) ABSTRACT

Compositions including phenylalanine, analogues, and phenylalanine precursors protect plants against environmental stressors. Delivery systems and methods of treating are provided. A method of protecting plants against environmental and/or biological stressors includes administering a composition including phenylalanine, a phenylalanine precursor or other skikimate pathway or phenylpropanoid pathway compound, or an amino acid that can be converted to phenylalanine to at least one root, at least one germinating seed, or at least one epidermal surface of a plant. Administration of the composition to the root, seed, or plant improves or restores at least one growth characteristic of the plant when the plant is exposed to an environmental stressor such as ultra-violet radiation, cold, drought, salt, heat, fungus, beetles (e.g., Japanese beetles), hormones, bacteria, arthropods, and worms (e.g., soybean cyst nematode) or products of biotic organisms. Another method of protecting plants against environmental and/or biological stressors includes coating a plant (e.g., soybean) seed with a composition including phenylalanine, a phenylalanine precursor or other skikimate pathway or phenylpropanoid pathway compound, or an amino acid that can be converted to phenylalanine such that the composition protects the seed and a plant that grows from the seed from ultra-violet radiation, cold, drought, salt, heat, fungus, beetles (e.g., Japanese beetles), hormones, bacteria, arthropods, and worms (e.g., soybean cyst nematode) or products of biotic organisms. Plants and plant cells including an isolated nucleic acid encoding at least one prephenate dehydratase operably linked to a promoter are described herein.

3 Claims, 20 Drawing Sheets

FIG. 4
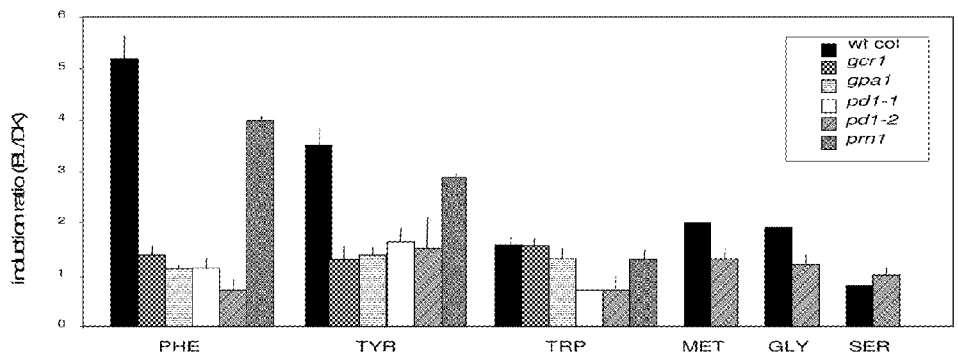
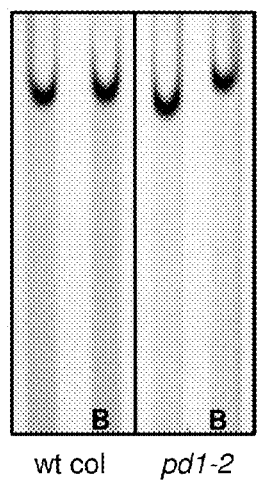
FIG. 5
wt col        pd1-2
FIG. 6
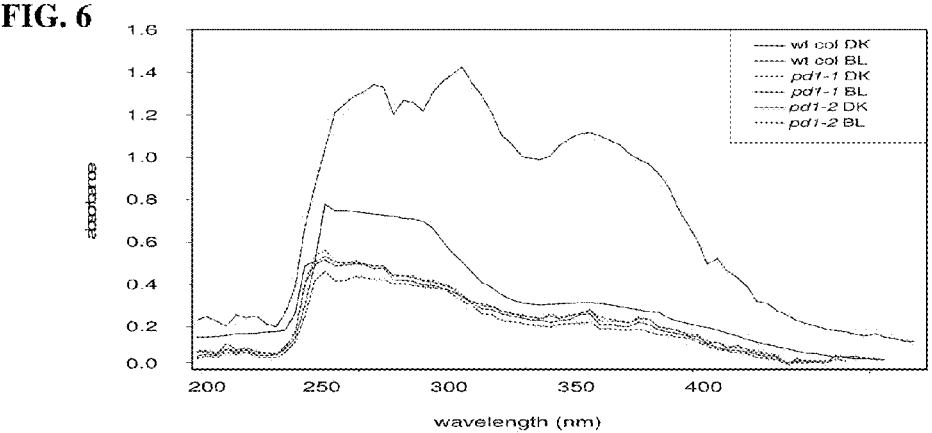

Untreated    300    317    368
(nm)

A

B

Untreated     300 nm + 1.0 mM phe     300 nm + 100 µM phe

Spectra in extract at room temp (low light)

v=vacuole

A

Untreated       300 nm + 1.0 mM phe   300 nm + 100 µM phe

B

FIG. 27 A　　　　　　　　　FUNGUS
Wt untreated　　　　　　　Wt + crypto
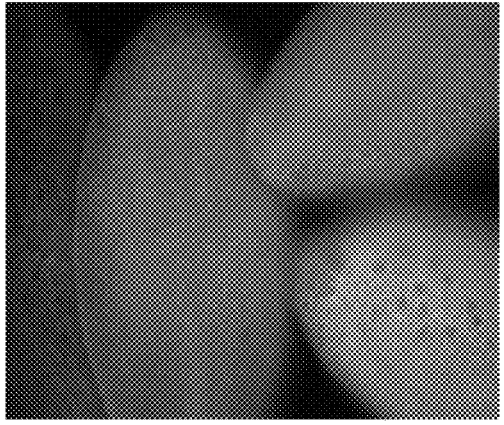
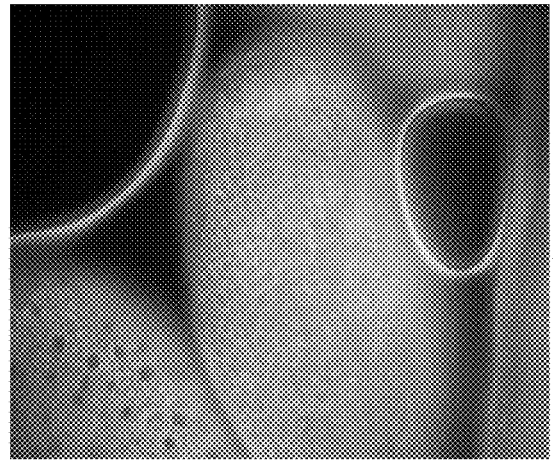
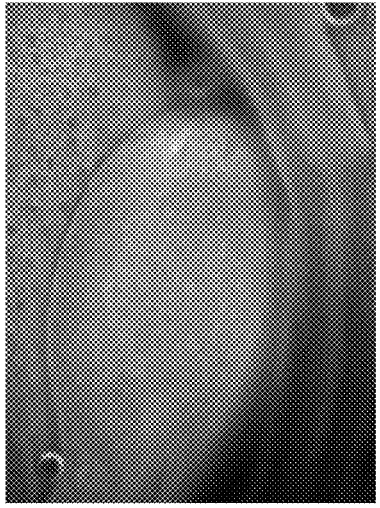
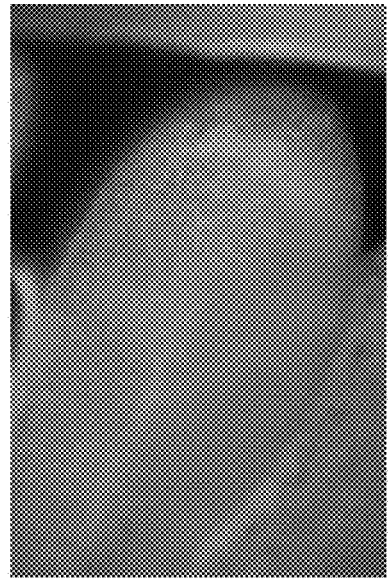
Wt + crypto example 2
Wt crypto + UV (UV enhances defense as it would in the real world)

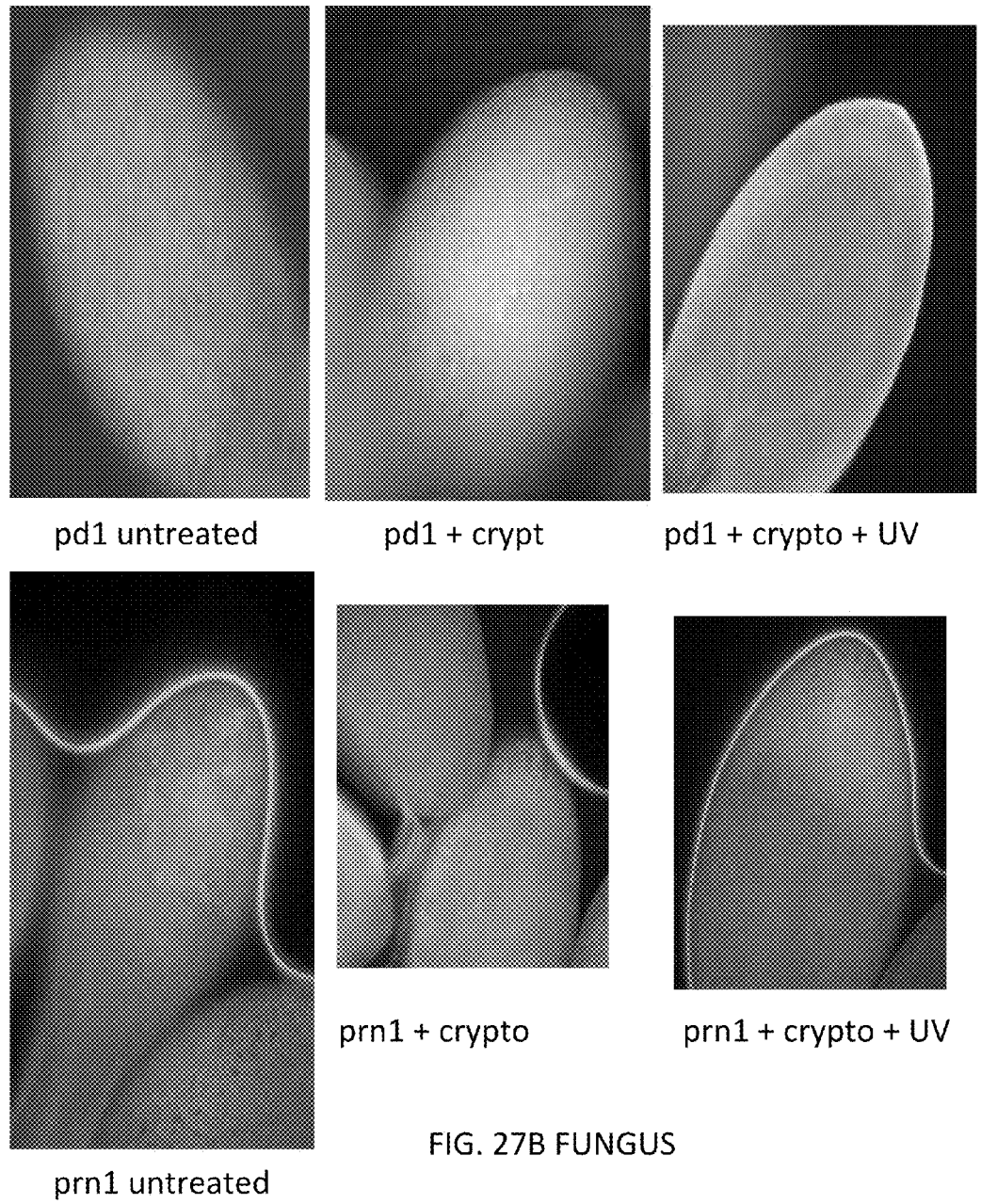
FIG. 27B FUNGUS

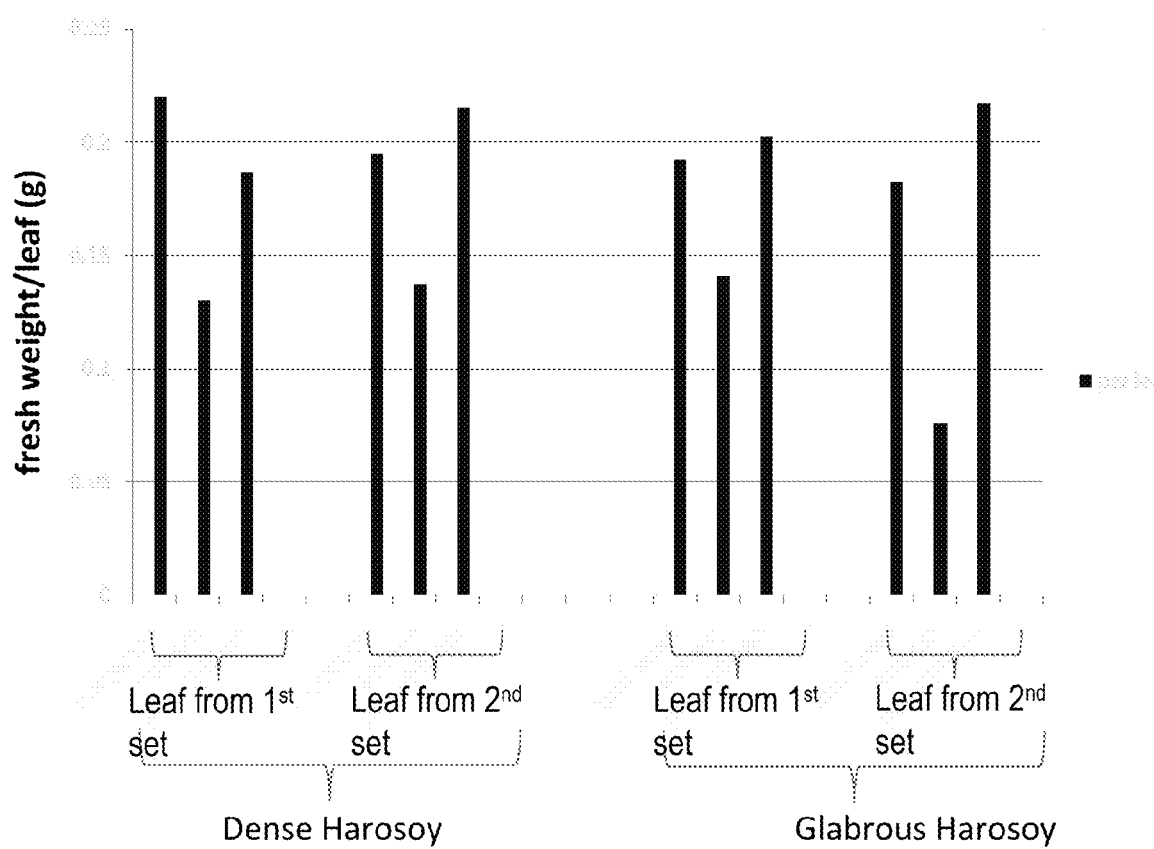
FIG. 28A    JAPANESE BEETLES

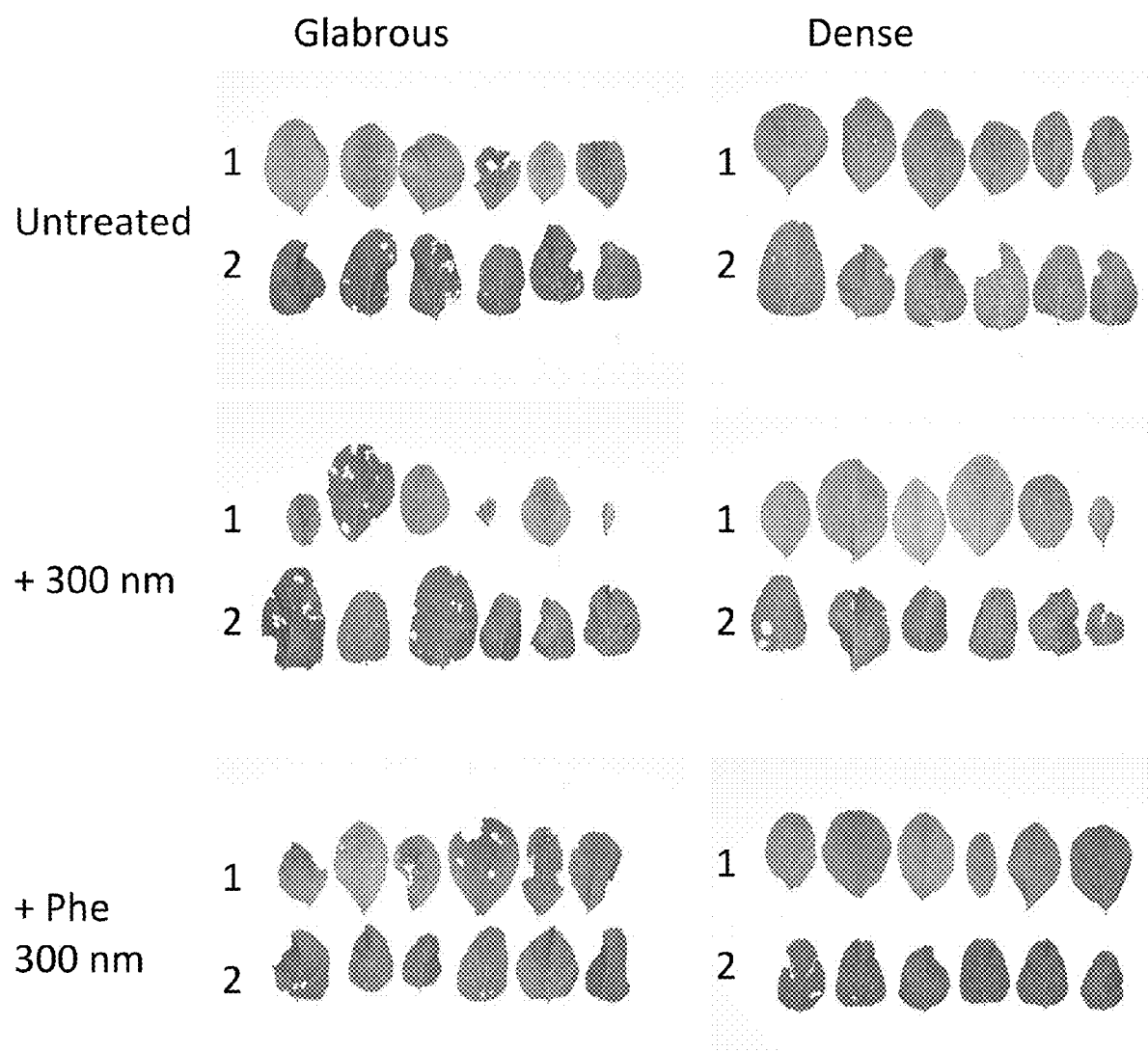

PLANT BIOCHEMICAL SYSTEMS AND USES THEREOF

CROSS-REFERENCE TO RELATED APPLICATIONS

This application is a Continuation-in-Part of International Patent Application No. PCT/US2008/55036, filed Feb. 26, 2008, which claims the benefit of U.S. Provisional Patent Application No. 60/975,513 filed Sep. 26, 2007 and U.S. Provisional Patent Application No. 60/891,698 filed Feb. 26, 2007. This application also claims the benefit of U.S. Provisional Patent Application No. 61/096,533 filed Sep. 12, 2008.

STATEMENT AS TO FEDERALLY SPONSORED RESEARCH

This invention was made with government support under grants USDA/CSREES 2003-35304-13482 and USDA/CSREES 2006-34263-16926 awarded by the Cooperative State Research, Education, and Extension Service (CSREES), which is an agency within the U.S. Department of Agriculture (USDA), part of the executive branch of the Federal Government. The government has an interest in the invention.

FIELD OF THE INVENTION

The invention is related to plant biochemical systems and protection of plants against environmental and biological effects and changes.

BACKGROUND

Environmental stressors are capable of causing genetic mutations in plants that result in severe damage to the photosynthetic apparatus. Light in the ultra-violet (UV) range is capable of causing the formation of thymidine dimers that result in genetic mutation in all organisms and in plants, severe damage to the photosynthetic apparatus. It is also the case that irradiation of plants with UV-B and the more energetic parts of UV-A causes major perturbations in cellular homeostasis and significant amounts of substrates, especially phenylalanine (Phe), are diverted from normal primary and secondary metabolic pathways into the production of specific UV screening pigments via the phenylpropanoid pathway. Ultra-violet-B (UV-B) radiation, for example, causes damage to plant life worldwide, and many mechanisms have evolved to help defend against the UV-A (320-400 nm) and UV-B (290-320 nm) that penetrates the atmosphere (Rozema et al., P. Photochem. Photobiol. B: Biology 66:2-12, 2002). Important to plant defenses are UV-screening compounds, such as the flavonoids, particularly inducible flavonols like quercetin (Rozema et al., P. Photochem. Photobiol. B: Biology 66:2-12, 2002; Stapleton and Walbot, Plant Physiology 105:881-889, 1994). Etiolated *Arabidopsis* seedlings, lacking a functional PD1 gene are unable to synthesize phenylalanine (Phe) and as a consequence, phenylpropanoid pigments (Warpeha et al., Plant Physiol. 140:844-855, 29006). Low doses of high energy UV-C (254 nm) are lethal to etiolated pd1 mutants (Phe absorbs up to 280 nm), gcr1 mutants and gpa1 mutants, but not to etiolated wt seedlings or seedlings of mutants of other members of the prephenate dehydratase (PD) family, indicating that this specific G-protein signaling pathway is critical to provide protection from UV via synthesis of Phe.

The erosion of the ozone layer and the consequential increase in UV exposure is an issue of increasing concern, as all populations are dependent upon vegetation for food, medicines and building materials. In addition to environmental stressors such as UV exposure, a number of biological stressors (e.g., fungi, bacteria, arthropods, etc.) cause harm to plants and threaten food crop yields. With the escalation of atmospheric and ecological onslaughts on plants and the continued increase in the world's population, there is a need to understand the pathways involved in conferring resistance to stressors and producing plants, especially crops, which are resistant to such onslaughts.

SUMMARY

Compositions and methods for protecting plants from environmental stressors (e.g., radiation) are described herein. The regulation of biosynthesis of phenylalanine by light and hormones, the relationship of phenylalanine concentration to the synthesis of various products of the phenylpropanoid pathway (e.g., flavonoids, hydroxycinnamic acid esters, glucosinolates and indole phytoalexins), how these products of phenylalanine contribute to protection from incident UV radiation, and how phenylalanine may behave in solution by itself and in a mixture with those products of phenylalanine (those that contribute to protection from incident UV radiation) or the substances utilized to deliver the phenylalanine/products of phenylalanine mixture are also discussed. In the experiments described below, soybean plants were protected from stressors using the compositions and methods described herein. However, the compositions and methods described herein can be applied to any plant. Examples of plants include rice, cotton, soybean, wheat, alfalfa, corn, garden pea, barley, rye. As used herein, the terms "blue light," "BL," "blue light/UVA" and "BL/UVA" mean ultra-violet A (320-350). Unless indicated otherwise, use of the terms "UV" or "ultra-violet" throughout the specification means ultra-violet B (290-320 nm).

By the term "biotic stressor" is meant any biological organism itself or materials, secretions or compounds derived from living organisms.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 4 is a graph showing the results from an HPLC analysis of 7-day-old etiolated wild-type and pd1 and other mutants directly in the *Arabidopsis* PD1 signaling pathway demonstrating that wild-type makes phenylalanine in response to blue light (BL), but pd1 mutants and other pathway constituents do not make phenylalanine in response to BL.

FIG. 5 is a photograph of the cell-free extract solutions of six-day-old dark-grown wt and pd1 mutant seedlings that were treated on day 6 with BL or no light, returned to darkness for 2 h with phenylalanine and pigments visible in spectra (shown in FIGS. 6 and 7).

FIG. 6 is a graph of absorbance spectra of cell-free extracts of six-day old etiolated *Arabidopsis* seedlings with buffer containing phenylalanine. There is significant pigment absorbance and stability in wild-type seedlings treated with BL but not pd1 mutants, measured at 2 h or 16 h post irradiation (solution kept at 4° C.).

" FIG. 10A: Seedlings seven d past treatment from the side view.

FIG. 27A is a series of photographs of *Arabidopsis* seedlings that have been grown in complete darkness for 6 days. On day 6 seedlings received an application of *Cryptococcus* ("crypto") fungi direct to the cotyledon tip under green safelight then seedlings were returned to the complete darkness. 24 hours later seedlings were photographed under deconvoluting microscopy on real color. Wt=wild type *Arabidopsis*.

FIG. 27B is a series of photographs of *Arabidopsis* mutant seedlings that have been grown in complete darkness for 6 days. On day 6 seedlings received an application of *Cryptococcus* ("crypto") fungi direct to the cotyledon tip under green safelight then seedlings were returned to the complete darkness. 24 hours later seedlings were photographed under deconvoluting microscopy on real color. pd1=prephenate dehydratase 1 mutant; prn1=pirin1 mutant.

FIG. 28A is a graph showing results from experiments in which germinating soybean seedlings exposed to UV-B radiation demonstrated increased predation that can be reduced by Phe.

FIG. 28B is a series of photographs of soybean leaves that are representative of the data presented in FIG. 28A.

DETAILED DESCRIPTION

Figure 1:
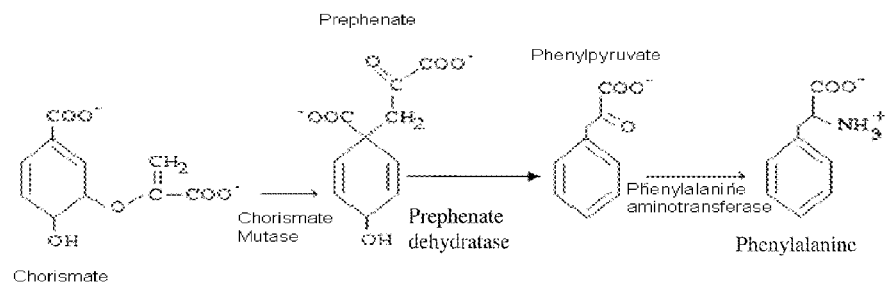
FIG. 1 is a schematic illustration showing the phenylalanine synthesis pathway for many organisms including etiolated *Arabidopsis*.
Figure 2:
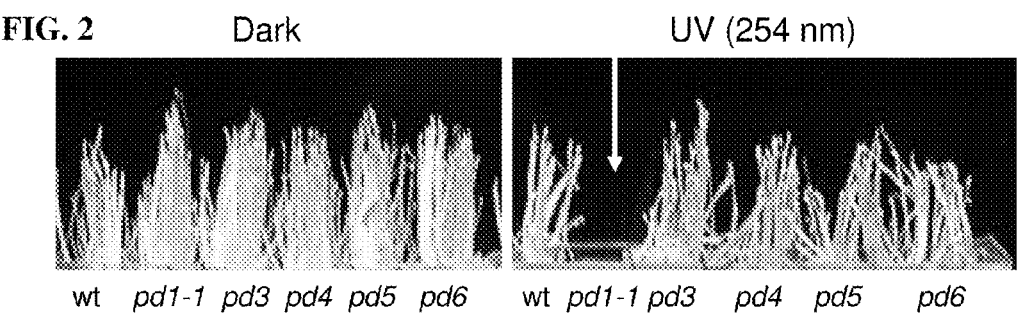
FIG. 2 is a scan of a photograph showing six-day-old etiolated wild type and insertion mutants of pd1, 2, 3, 4, 5 and 6 that were treated with no light or with a single 4 min pulse of 254 nm radiation and photographed 24 hr later. The UV treatment is lethal to only pd1 and they are lying flat on the agar surface.

In one embodiment of the present disclosure, a method includes administering a composition comprising phenylalanine or a phenylalanine precursor to at least one root or at least one epidermal surface of a plant, wherein administration of the composition to the plant improves or restores at least one growth characteristic of the plant when the plant is exposed to an environmental stressor such as but not limited to UV radiation, heat, salt and/or a biotic stressor such as, for example, fungus, beetles (e.g., Japanese beetles), hormones, bacteria, arthropods, worms (e.g., soybean cyst nematode), and exudates and compounds made by a biotic entity.

In one embodiment of the present disclosure, a soybean seed is coated with a composition comprising phenylalanine or at least one phenylalanine precursor, wherein the composition protects the seed and a soybean plant that grows from the seed from stressors including but not limited to ultraviolet radiation, salt, heat, fungus, beetles (e.g., Japanese beetles), hormones, bacteria, arthropods, worms (e.g., soybean cyst nematode), and exudates and compounds made by a biotic entity.

In one embodiment of the present disclosure, a plant cell includes an isolated nucleic acid encoding at least one prephenate dehydratase, the nucleic acid operably linked to a promoter.

In one embodiment of the present disclosure, a method includes contacting soil containing a plurality of soybean seeds or roots of a plurality of soybean plants with a composition comprising phenylalanine, a phenylalanine precursor, or an amino acid that can be converted to phenylalanine, wherein contacting the soil with the composition protects the plurality of soybean seeds or the plurality of plants from at least one environmental stressor such as but not limited to UV radiation, heat, salt, and/or at least one biotic stressor such as, for example, fungus, beetles (e.g., Japanese beetles), hormones, bacteria, arthropods, worms (e.g., soybean cyst nematode), and exudates and compounds made by a biotic entity.

In this embodiment, any amount suitable for protecting the plurality of soybean seeds or the plurality of plants from at least one environmental stressor can be used. Typically this amount is no higher than 2 mM but can be as low as 50 μM in some applications, and for some seed types, even lower quantities can be employed.

In one embodiment of the present disclosure, a method includes administering to a plant, plant cell or seed a composition comprising a nucleic acid encoding at least one prephenate dehydratase, the nucleic acid operably linked to a promoter, wherein administration of the composition protects the plant, plant cell or seed from at least one environmental stressor such as UV radiation, heat, salt and/or at least one biotic stressor such as, for example, fungus, beetles (e.g., Japanese beetles), hormones, bacteria, arthropods, worms (e.g., soybean cyst nematode) or exudates and compounds (any products) made by a biotic entity.

In one embodiment of the present disclosure, a vector includes a nucleic acid encoding at least one prephenate dehydratase, the nucleic acid operably linked to a promoter.

In another embodiment, a plant cell (e.g., a crop plant such as soybean) includes an isolated nucleic acid encoding for prephenate dehydratase (e.g., prephenate dehydratase 1 or a homologue thereof), the nucleic acid operably linked to a promoter such that prephenate dehydratase is expressed at sufficient levels to protect the plant cell from damage from a stressor such as UV radiation, cold, drought, heat, salt, hormones, fungi, bacteria, arthropods, worms, and products of living organisms. Examples of damage include root damage, leaf damage, meristematic damage, shoot damage, inflorescence damage, pod damage, seed damage, and any damage adversely impacting or reducing yield. In different tissues of the plant, sufficient levels may be nanomolar quantities, in other tissues they may be micromolar quantities. In this embodiment, sufficient levels have been detected as low as nanomolar quantities by HPLC.

In yet another embodiment, a plant seed (e.g., a crop plant such as soybean) is coated with a composition including phenylalanine, at least one phenylalanine precursor or other skikimate pathway phenylpropanoid pathway compound that can be converted to phenylalanine, or an amino acid that can be converted to phenylalanine in an amount sufficient to protect the plant seed and a plant that grows from the plant seed from damage from a stressor such as UV radiation, cold, drought, heat, salt, hormones, fungi, bacteria, arthropods, worms and products of biotic organisms. Plant coatings approximately 1-100 μM have worked in the field. Typically, an amount sufficient to protect the plant varies but can be low as 1 μM.

Upon reviewing the aforementioned embodiments, it would be evident to an artisan with ordinary skill in the art that said embodiments can be modified, reduced, or enhanced without departing from the scope and spirit of the claims described below.

These are but a few examples of modifications that can be applied to the present disclosure without departing from the scope of the claims. Accordingly, the reader is directed to the claims section for a fuller understanding of the breadth and scope of the present disclosure.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

Soybean has tremendous economic importance as a domestic and export crop for oil and protein and because it can fix atmospheric nitrogen and thereby add nitrogen to the soil—making it an ideal rotation crop for maize or wheat. Soybean cultivation is a multi-billion dollar industry and one of the USA's chief agricultural exports, and is predicted to continue to grow. In Illinois, soybean derived goods now account for a significant percentage of agricultural profit for US farmers and breeders. Illinois is among the top three soybean producers within the US, with a record crop produced in 2006 (USDA National Agricultural Statistics Service, 2007). Moreover, as atmospheric damage is not expected to improve immediately, the sustainable agriculture will likely become reliant on crop species that can fix atmospheric nitrogen and can withstand increased penetration of UV radiation. Soybean is known to be a UV-sensitive plant and numerous varieties of commercially used soybean remain highly sensitive to UV radiation. Soybean (and other crop plants) are also susceptible to a multitude of pests (fungus, nematode worms, insects) and environmental sensitivities which costs agriculture billions a year in preventative and therapeutic treatments. These externally applied treatments are delivered to soil, seed or plants via liquid, gels, liquid coatings that dry on seed, and other solid forms, in order to minimize environmental and pest damage to crops. Because phenylalanine facilitates hair and pigment development in plants, and hair and pigment development have been shown to repel pests, the compositions and methods described herein can find use in protecting plants from pests.

Seed Coatings

The compositions described herein for protecting plants from UV and other environmental stressors can be applied by seed treatment (e.g., applying the composition directly to the seed). An advantage of seed treatment is that by being applied on the seed directly, a significantly smaller amount of composition is required per hectare compared to other methods that do not involve direct application to the seed. Any suitable delivery vehicle can be used for delivering compositions as described herein, including liquids, gels, and powders. If the delivery vehicle is a liquid or a gel, the liquid or gel typically has a pH in the range of about 5.8 to about 7.5. Liquid, gel (e.g., agarose-based, gelatin, etc.) and power-based delivery systems are known in the art. For example, in some embodiments, the delivery vehicle is a polymer-based system, in which a composition for protecting plants from UV is added to a commercially available inert polymer and the resultant composition provides for slow or temperature-induced delivery of the agent. In another example, a gelatinous polymer containing a composition for protecting plants from environmental stressors (e.g., UV radiation) is used to coat the seed and is dried on. In another example, a slurry treatment can be used to coat seeds with a composition as described herein. In a typical slurry treatment, a composition as described herein is added to water, and this mixture is applied as a slurry treatment on the seed.

One example of a liquid delivery vehicle that is commercially available is the Disco Ag filmcoat sold by Incotec (Salinas, Calif.). In some embodiments, a composition as described herein can provide a controlled release of an agent for protecting a plant from UV (e.g., a nucleic acid encoding an enzyme responsible for the production of phenylalanine or a phenylalanine precursor, a nucleic acid encoding an enzyme that converts an amino acid (e.g., tyrosine) to phenylalanine) to make the agent available when required. Such a composition can also provide for a delayed release of the agent until conditions are optimal, e.g., prevent imbibing of water until a sufficiently warm growing season for soybean.

Nucleic Acids Encoding Phenylalanine and Phenylalanine Precursors and Expression Control Sequences:

Described herein are nucleic acids encoding enzymes responsible for the production of phenylalanine, nucleic acids encoding enzymes responsible for the production of phenylalanine precursors (e.g., chorismate, prephenate, phenylpyruvate, tyrosine, and any amino acid that can be converted to phenylalanine), and nucleic acids encoding enzymes that can convert an amino acid (e.g., tyrosine) to phenylalanine. In some embodiments, such nucleic acids are incorporated into recombinant nucleic acid constructs, e.g., DNA constructs such as vectors, capable of introduction into and replication in a host cell. Such a construct includes at least one expression control sequence, e.g., a replication sequence, a promoter, an enhancer, a transcription initiation start site, a ribosome binding site, a transcription termination site, a polyadenylation signal, etc. One example of an enzyme that is responsible for the production of a phenylalanine precursor is prephenate dehydratase (PD), one enzyme in the PD family of enzymes (e.g., PD1, PD2, PD3, etc.). This enzyme converts prephenate to phenylpyruvate. Phenylpyruvate can then be converted to phenylalanine by any of several transaminases (i.e., enzymes responsible for the production of phenylalanine. PD amino acid sequences and nucleic acid sequences encoding PD are known in the art. A non-exhaustive list of pd gene names and corresponding accession numbers includes: At1g08250, prephenate dehydratase family protein, NM_100698; At1g11790, prephenate dehydratase family protein, NM_001035947; At2g27820, Prephenate dehydratase 1 (PD1), NM_128342; At3g07630, prephenate dehydratase family protein, NM_111642.2; At3g44720, prephenate dehydratase family protein, NM_114340; and At5g22630, prephenate dehydratase family protein, NM_122169.

Synthesis of phenylalanine and phenylalanine precursors in plants is achieved by introducing into a plant a nucleic acid sequence encoding one or more enzymes responsible for the production of phenylalanine, a nucleic acid sequence encoding one or more enzymes responsible for the production of phenylalanine precursors, or a nucleic acid encoding an enzyme that can convert an amino acid (e.g., tyrosine) to phenylalanine. Such nucleic acid sequences can be incorporated into any suitable vector (e.g., expression vector) for stable transformation of plant cells or for the establishment of transgenic plants.

Any type of suitable promoter can be used. Promoters useful in the compositions and methods described herein are any known promoters that are functional in a plant. Many such promoters are well known to the ordinarily skilled artisan e.g. (*Phaseolus vulgaris*) stress-related gene number 2 (PvSR2) gene responds to heavy metals but not to other forms of environmental stresses. The promoter region was identified as the region (−1623/+48) of PvSR2 (X. Qi et al, *Plant Physiology* 143:50-59 (2007)).

Inducible or other types of promoters include promoters normally associated with other genes, and/or promoters isolated from any bacterial, viral, eukaryotic e.g. mammalian, or plant cell. It may be advantageous to employ a promoter that effectively directs the expression of the foreign coding sequence in the cell or tissue type chosen for expression. The use of promoter and cell type combinations for protein expression is generally known to those of skill in the art of molecular biology, for example, see Sambrook et al., In: Molecular Cloning: A Laboratory Manual, Cold Spring Harbor Laboratory, Cold Spring Harbor, N.Y., 1989. The promoters employed may be constitutive, or inducible, and can be used under the appropriate conditions to direct high level expression of the introduced DNA segment, such as is advantageous in the large-scale production of recombinant proteins or peptides. The term "constitutive" used in the context of a promoter means that the promoter is capable of directing transcription of an operably linked nucleic acid sequence in the absence of a stimulus (e.g., heat shock, chemicals, etc.). In contrast, an "inducible" promoter is one which is capable of directing a level of transcription of an operably linked nucleic acid sequence in the presence of a stimulus or environmental stress (e.g., heat shock, irradiation, chemicals, etc.), wherein the level of the transcription is different from that in the absence of the stimulus.

Promoters which are useful for plant transgene expression include those that are inducible, viral, synthetic, constitutive, temporally regulated, spatially regulated, tissue-specific, and spatio-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A number of plant promoters have been described with various expression characteristics. Examples of some constitutive promoters which have been described include the rice actin 1 (Wang et al., 1992; U.S. Pat. No. 5,641,876), CaMV 35S, CaMV 19S, sucrose synthase, and the ubiquitin promoters.

Examples of tissue specific promoters which have been described include the lectin, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, truncated CaMV 35s, potato patatin, root cell, maize zein, globulin-1, α-tubulin, cab, PEPCase, R gene complex-associated promoters, and chalcone synthase promoters.

Inducible promoters that have been described include the ABA- and turgor-inducible promoters, the promoter of the auxin-binding protein gene, the UDP glucose flavonoid glycosyl-transferase gene promoter, the MPI proteinase inhibitor promoter, and the glyceraldehyde-3-phosphate dehydrogenase gene promoter.

Several tissue-specific regulated genes and/or promoters have been reported in plants. These include genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase, fatty acid desaturases (fad 2-1)), and other genes expressed during embryo development (such as Bce4, see, for example. EP 255378 a). Particularly useful for seed-specific expression is the pea vicilin promoter. (See also U.S. Pat. No. 5,625,136, herein incorporated by reference.) Other useful promoters for expression in mature leaves are those that are switched on at the onset of senescence, such as the SAG promoter from *Arabidopsis*.

Other exemplary plant functional promoters, which can be used to express a gene of the present invention, are among the following: CaMV 35S and 19S promoters (U.S. Pat. Nos. 5,352,605 and 5,530,196); patatin promoter (U.S. Pat. No. 5,436,393); a B33 promoter sequence of a patatin gene derived from *Solanum tuberosum*, and which leads to a tuber specific expression of sequences fused to the B33 promoter (U.S. Pat. No. 5,436,393); tomato E8 promoter (WO 94/24298); tomato fruit promoters (U.S. Pat. No. 5,556,653); -a plant ubiquitin promoter system (U.S. Pat. Nos. 5,614,399 and 5,510,474); 5' cis-regulatory elements of abscisic acid-responsive gene expression (U.S. Pat. No. 5,824,865); promoter from a badnavirus, rice tungro bacilliform virus (RTBV) (U.S. Pat. No. 5,824,857); a chemically inducible promoter fragment from the 5' flanking region adjacent the coding region of a tobacco PR-1a gene (U.S. Pat. No. 5,789,214); a raspberry dru1 promoter (U.S. Pat. No. 5,783,394); strawberry promoters and genes (WO 98/31812); promoter is the napin promoter, the phaseolin promoter, and the DC3 promoter (U.S. Pat. No. 5,773,697); a LEA promoter (U.S. Pat. No. 5,723,765); 5' transcriptional regulatory region for sink organ specific expression (U.S. Pat. No. 5,723,757); G-box related sequence motifs, specifically lwt and PA motifs, which function as cis-elements of promoters, to regulate the expression of heterologous genes in transgenic plants (U.S. Pat. No. 5,723,751); P119 promoters and their use (U.S. Pat. No. 5,633,440); Group 2 (Gp2) plant promoter sequences (U.S. Pat. No. 5,608,144); nucleic acid promoter fragments derived from several genes from corn, petunia and tobacco (U.S. Pat. No. 5,608,143); promoter sequences isolated from the nuclear gene for chloroplast GS2 glutamine synthetase and from two nuclear genes for cytosolic GS3 glutamine synthetase in the pea plant, *Pisum sativum* (U.S. Pat. No. 5,391,725); full-length transcript promoter from figwort mosaic virus (FMV) (U.S. Pat. No. 5,378,619); an isocitrate lyase promoter (U.S. Pat. No. 5,689,040); a microspore-specific regulatory element (U.S. Pat. No. 5,633,438); expression of heterologous genes in transgenic plants and plant cells using plant asparagine synthetase promoters (U.S. Pat. No. 5,595,896); a promoter region that drives expression of a 1450 base TR transcript in octopine-type crown gall tumors (U.S. Pat. No. 4,771,002); promoter sequences from the gene from the small subunit of ribulose-1,5-bisphosphate carboxylase (U.S. Pat. No. 4,962,028); the *Arabidopsis* histone H4 promoter (U.S. Pat. No. 5,491,288); a seed-specific plant promoter (U.S. Pat. No. 5,767,363); a 21 by promoter element which is capable of imparting root expression capability to a rbcS-3A promoter, normally a green tissue specific promoter (U.S. Pat. No. 5,023,179); promoters of tissue-preferential transcription of associated DNA sequences in plants, particularly in the roots (U.S. Pat. No. 5,792,925); *Brassica* sp. polygalacturonase promoter (U.S. Pat. No. 5,689,053); a seed coat-specific cryptic promoter region (U.S. Pat. No. 5,824,863); a chemically inducible nucleic acid promoter fragment isolated from the tobacco PR-1a gene inducible by application of a benzo-1,2,3-thiadiazole, an isonicotinic acid compound, or a salicylic acid compound (U.S. Pat. No. 5,689,044); promoter fragment isolated from a cucumber chitinase/lysozyme gene that is inducible by application of benzo-1,2,3-thiadiazole (U.S. Pat. No. 5,654,414); a constitutive promoter from tobacco that directs expression in at least ovary, flower, immature embryo, mature embryo, seed, stem, leaf and root tissues (U.S. Pat. No. 5,824,872); alteration of gene expression in plants (U.S. Pat. No. 5,223,419); a recombinant promoter for gene expression in monocotyledenous plants (U.S. Pat. No. 5,290,924); method for using TMV to overproduce peptides and proteins (WO 95/21248); nucleic acid comprising shoot meristem-specific promoter and regulated sequence (WO 98/05199); phaseolin promoter and structural gene (EP-B-0122791); plant promoters [sub domain of CaMV 35S] (U.S. Pat. No. 5,097,025); use of tomato E8-derived promoters to express heterologous genes, e.g. 5-adenosylmethionine hydrolase in ripening fruit (WO 94/24294); method of using transactivation proteins to control gene expression in transgenic plants (U.S. Pat. No. 5,801,027); DNA molecules encoding inducible plant promoters and tomato Adh2 enzyme (U.S. Pat. No. 5,821,398); synthetic plant core promoter and upstream regulatory element (WO 97/47756); monocot having dicot wound inducible promoter (U.S. Pat. No. 5,684,239); selective gene expression in plants (U.S. Pat. No. 5,110,732); CaMV 35S enhanced mannopine synthase promoter and method for using the same (U.S. Pat. No. 5,106,739); seed specific transcription regulation (U.S. Pat. No. 5,420,034); seed specific promoter region (U.S. Pat. No. 5,623,067); DNA promoter fragments from wheat (U.S. Pat. No. 5,139,954); chimeric regulatory regions and gene cassettes for use in plants (WO 95/14098); production of gene products to high levels (WO 90/13658); HMG promoter expression system and post harvest production of gene products in plants and plant cell cultures (U.S. Pat. No. 5,670,349); gene expression system comprising the promoter region of the alpha amylase genes in plants (U.S. Pat. No. 5,712,112).

Organelle-specific, tissue-specific, and development-specific promoters are also contemplated for use in the present invention. Examples of these included, but are not limited to: the ribulose bisphosphate carboxylase (RuBisCo) small subunit gene promoters or chlorophyll a/b binding protein (CAB) gene promoters for expression in photosynthetic tissue; the various seed storage protein gene promoters for expression in seeds; and the root-specific glutamine synthetase gene promoters where expression in roots is desired. Examples of organelle specific promoters include, but are not limited to the ribulose bisphosphate carboxylase (RuBisCo) large subunit gene promoter and the D1 protein promoter. In one preferred embodiment, the expression cassette comprises a chloroplast specific promoter.

The Effects of UV Radiation on Higher Plants:

Environmental data collected over the last decade indicate UV radiation is increasing in the highly energetic and damaging UV-B range. Increased exposure of agriculturally important plants to UV-B results in reduced biomass yield, reduced nutritional content, decreased photosynthetic capability, decreased disease resistance, changes in species competition in ecosystems, changes in plant ultrastructure and pigment production, decreased seed viability, and decreased seed production. Young plants are the most vulnerable to external stresses, including UV-B radiation.

Soybean is particularly sensitive to UV-B radiation and exposure of soybean to UV-B has deleterious effects on a variety of physical and metabolic characters including photosynthetic capacity, overall growth, and reproductive fitness, although the magnitude of specific responses may vary from cultivar to cultivar.

The Relevance of Phenylalanine and Phenylpropanoids to UV Resistance:

Plants are thought to screen out harmful UV radiations by placing phenylpropanoid based pigments in strategic locations; tissues with high rates of cell division and/or DNA replication, or tissues with a direct role in gamete formation. The phenylpropanoid pathway initiates with, and is thought to be limited by the concentration of, the aromatic amino acid phenylalanine. Thus, a plant with low levels of phenylalanine may not be able to produce adequate levels of pigment to protect against UV damage. This may be particularly critical for young etiolated or newly emergent crop seedlings in the field which contain very little phenylalanine, because UV damage that occurs at the seed or young plant stage has been shown to negatively affect the adult plant.

The Pathway(s) from Chorismate to Phenylalanine in Higher Plants, Etiolated *Arabidopsis* and Soybean:

The biosynthesis of phenylalanine is well understood and documented in prokaryotes, but not higher plants although a significant amount of progress has been made in the past few years.

In prokaryotes chorismate serves as the substrate for first branch point in the production of phenylalanine (See FIG. 1). Chorismate mutase catalyzes the conversion of chorismate to prephenate which is then converted to phenylpyruvate via prephenate dehydratase. Phenylpyruvate is converted immediately to phenylalanine by any of several transaminases. In some bacteria chorismate mutase and prephenate dehydratase are synthesized as a single [fusion] protein referred to as P-protein.

In higher plants, prephenate was commonly thought to be converted to phenylalanine in the chloroplast via an arogenate intermediate and that this conversion was in part catalyzed by arogenate dehydratase. However, our evidence demonstrates that in etiolated *Arabidopsis*, phenylalanine production is catalyzed by prephenate dehydratase 1 (PD1) and proceeds via a phenylpyruvate intermediate much the same as in bacteria. We have also demonstrated that the process could be induced by BL acting though a G-protein intermediate.

In *Arabidopsis* there are two confirmed (CM1, CM2) and one potential (CM3) genes coding for chorismate mutase. CM1 (chloroplast pathway) is subject to feedback inhibition from phenylalanine, while CM2 (cytoplasmic pathway) is not, but all lead to phenylalanine formation.

For Soybean, public databases indicate more than 36 ESTs coding for genes with amino acid sequence homology to P-Protein. Until the full genome is sequenced it will be difficult to determine exactly how many chorismate mutase and prephenate dehydratase genes there are.

Light Regulation of the Phenylpropanoid Pathway:

The phenylpropanoid pathway produces four different classes of secondary metabolites one of which is the flavonoids. The UV-screening pigments are often members of flavonoid class of metabolites. The pathway responsible for the general production of the flavonoids is well studied both genetically and with respect to regulation by light. In *Arabidopsis*, BL light acting alone can regulate the expression of phenylalanine ammonia lyase (PAL), the first enzyme in the general phenylpropanoid-committed pathway, and chalcone synthase (CHS), the first enzyme in the flavonoid-committed pathway. It has been shown in cultured parsley cells that either UV or BL alone are sufficient to enhance transcription of CHS. BL irradiation can also eliminate the lag in CHS transcript accumulation resulting from UV irradiation. In contrast, little is known regarding the genetics or the photoregulation of plant phenylalanine synthesis.

GCR1, GPA1 and Prephenate Dehydratase 1 are Required for Blue Light-Induced Production of Phenylalanine in Etiolated *Arabidopsis*:

Activated GPA1 has a specific physical interaction with PD1 that results in a significant increase in PD1 activity. PD1 is the only member of the PD family that is expressed in etiolated *Arabidopsis*. BL irradiation or ABA treatment of etiolated wild type (wt) *Arabidopsis* results in an increase in cytosolic PD1 activity, an increase in cytosolic levels of phenylpyruvate, phenylalanine and a series of UV absorbing compounds, and the appearance of specific fluorescent and waxy materials at the tips of the cotyledons. The increase in PD1 activity in response to BL or ABA treatment also requires GCR1. BL Irradiation or ABA treatment of pd1, gcr1 and gpa1 T-DNA insertion mutants result in none of these events described for wt. We conclude that GCR1, GPA1 and PD1 form a signaling chain that is responsible for ABA and BL induced synthesis of phenylpyruvate, phenylalanine and a series of UV absorbing products from the phenylpropanoid pathway. In etiolated seedlings phenylalanine is synthesized via a phenylpyruvate intermediate, much like in bacteria and fungi, and not via an arogenate pathway (Warpeha et al., Plant Physiol. 140:844-855).

The GCR1, GPA1, PRN1, NF-Y Signal Chain Mediates Both Blue Light and ABA Responses in *Arabidopsis*:

We have demonstrated that Pirin 1 (PRN1) acts as an effector for GPA1, the sole G alpha subunit coded by the *Arabidopsis* genome and that this GPA1-PRN1 interaction is critical to both ABA and BL activation of Lhcb gene transcription etiolated *Arabidopsis* seedlings. We have also established that the regulatory element responsible for BL regulated Lhcb expression contains a perfect CCAAT box. The data demonstrate that: PRN1 interacts with NF-Y (heterotrimeric CCAAT box binding proteins). NF-Y-A5, NF-Y-B9, and NF-Y-C9 are the likely components of the NF-Y heterotrimer responsible for BL and ABA mediated Lhcb expression in etiolated *Arabidopsis* (Warpeha et al. Plant Physiol. 143: 1590-1600).

Figure 3:
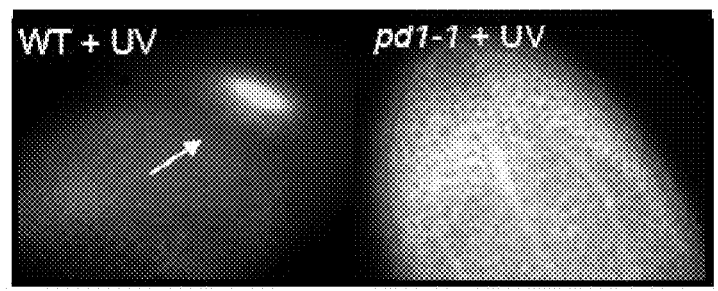
FIG. 3 is a photograph showing six-day-old etiolated wild type and pd1 mutants of *Arabidopsis*, which were irradiated with 366 nm radiation, placed back in the dark for 24 hr and then photographed using a deconvoluting microscope. As a result of the treatment, the tips of the cotyledons of wild type accumulate UV absorbing pigments, but not pd1-1 or pd1-2 mutants.
Figure 7:
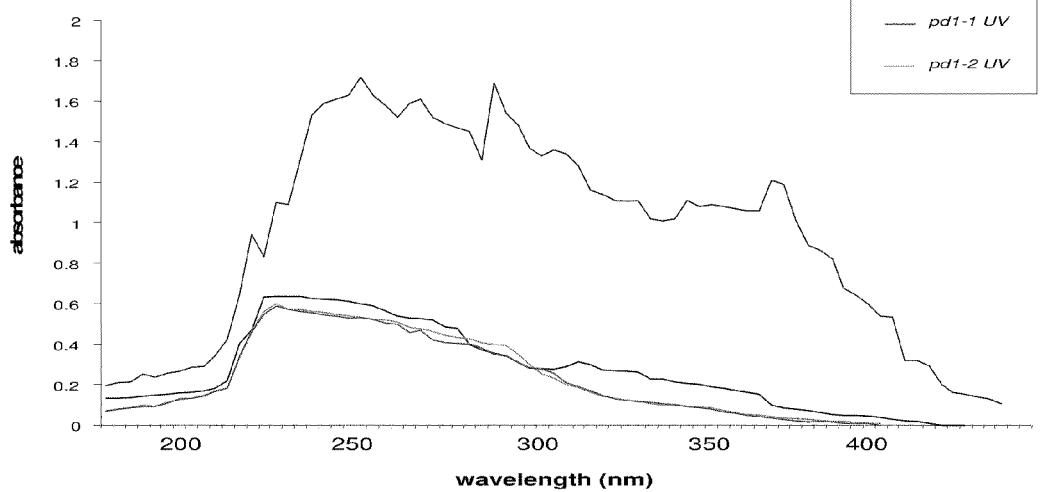
FIG. 7 is a graph of absorbance spectra of cell-free extracts of six-day old etiolated *Arabidopsis* seedlings with phenylalanine and buffer irradiated with UV (368 nm). There is significant pigment absorbance and stability in wild-type seedlings treated with BL but not pd1 mutants. Methods are same as for FIG. 6.
Figure 8:
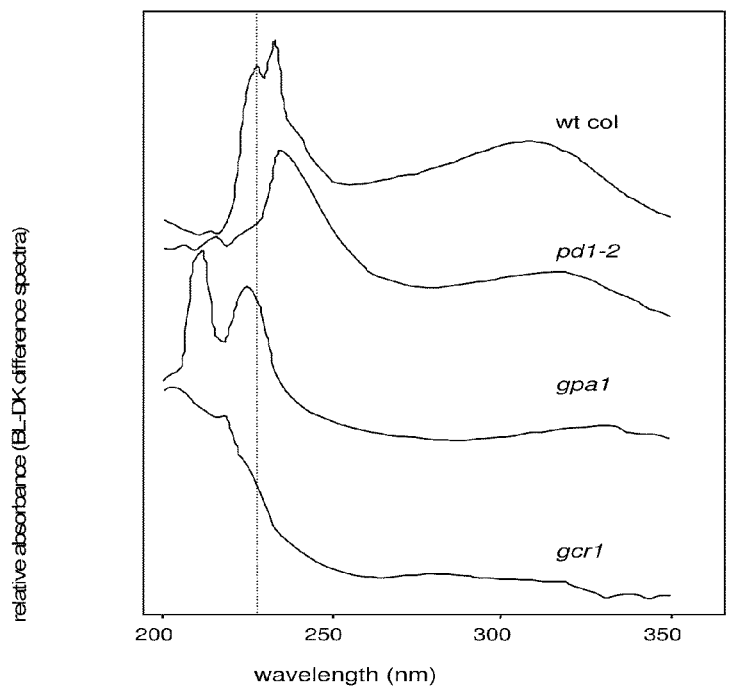
FIG. 8 is a graph of absorbance spectra of cell-free extracts of six-day old etiolated *Arabidopsis* mutant seedlings (indicated on figure) with phenylalanine and buffer irradiated with BL.

Phenylalanine Synthesized by the Prephenate Dehydratase Pathway is Important for Protection from UV Radiation Damage in Etiolated *Arabidopsis* and Soybean:

Environmental assessments over the last ten years indicate significant increases in incident UV radiation. We have demonstrated that phenylalanine is produced in response to BL or ABA treatment of etiolated wt *Arabidopsis* seedlings occurs via a G-protein mediated pathway and the specific activation of PD1 by direct interaction with activated GPA1 (the sole G-alpha encoded by the *Arabidopsis* genome). The phenylalanine produced in response to BL or ABA treatment via the GCR1-GPA1-PD1 pathway is used by the phenylpropanoid pathway to produce a range of UV absorbing compounds that protect etiolated seedlings *Arabidopsis* from UV damage. Mutants in gcr1, gpa1 or pd1 all show increased sensitivity to UV irradiation. The addition of phenylalanine to the growth media can rescue gcr1, gpa1 or pd1 mutants. The same phenomena that occur in etiolated *Arabidopsis* occur in etiolated soybean. Etiolated pd1 mutants are significantly more sensitive to UV-C radiation (254 nm) than are etiolated wt, or pd2, pd3, pd4, pd5, and pd6 mutants. Etiolated pd1 mutants fail to synthesize a range of UV light-absorbing compounds in response to BL or UV (FIGS. 2-7). The total lack of such compounds indicates that etiolated pd1 mutants may be more sensitive to high energy UV radiation than wt seedlings. Further, RT-PCR shows that only PD1 is expressed in etiolated seedlings suggesting that PD2-6 have no role in protecting etiolated seedlings from UV exposure. The cotyledons of etiolated wt *Arabidopsis* and pd1 mutants exhibit differences in the distribution of UV absorbing compounds following exposure to UV light. Etiolated wt and pd1 mutants were exposed to a brief pulse of UV-A (366 nm) and the resulting accumulation of UV absorbing materials in the cotyledons was observed via deconvolution microscopy. There is accumulation of UV-absorbing, fluorescent material in the epidermal cells of the wt cotyledons but not in the pd1 mutant (FIG. 3). Etiolated pd1 mutants and mutants of other genes important to the phenylalanine-synthesis pathway (i.e. gpa1, gcr1) do not absorb in the UV-blue range since they do not make all of the protective compounds. Wild type shows a prominent absorbance of protective compounds and phenylalanine itself (FIG. 8).

Figure 9:
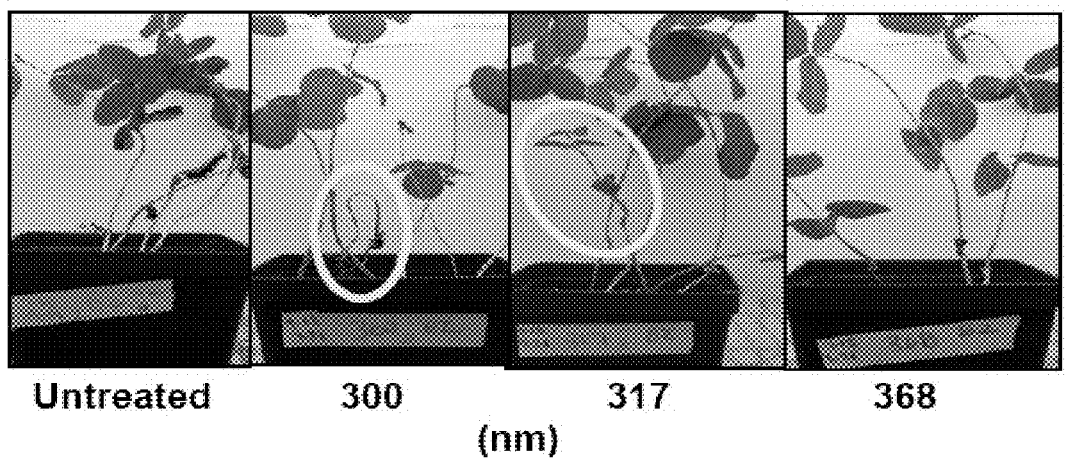
FIG. 9 is a series of photographs showing soybean grown in darkness from day 1-3 after planting, then treated with UV (300 or 317 or 368 nm), after which seedlings were maintained in lt-dk cycles for 21 days prior to photographing. Abnormal growth is highlighted in the figure.
Figure 10:
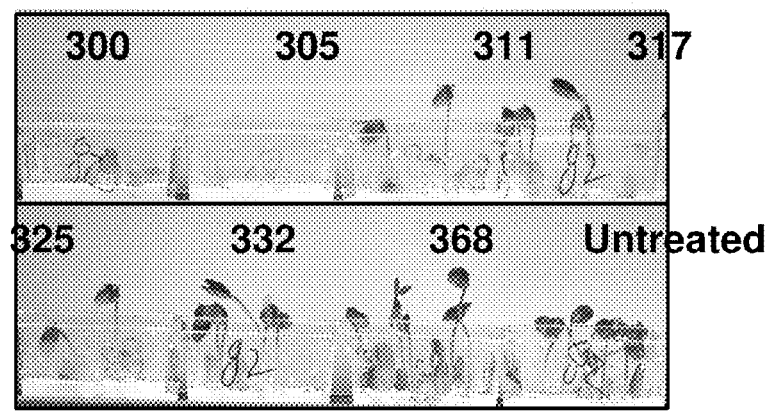
FIGS. 10A and B are photographs showing the soybean response to UV depends on wavelength and white light "recovery.
FIG. 10B: Sample seedling sets of five d past treatment, from overhead view.
Figure 10:
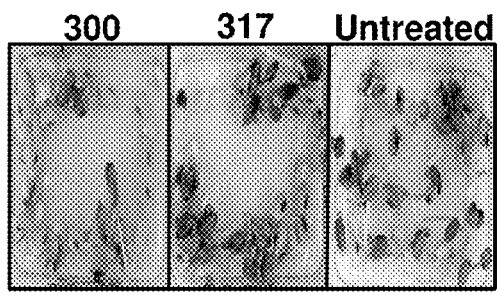
Figure 11A:
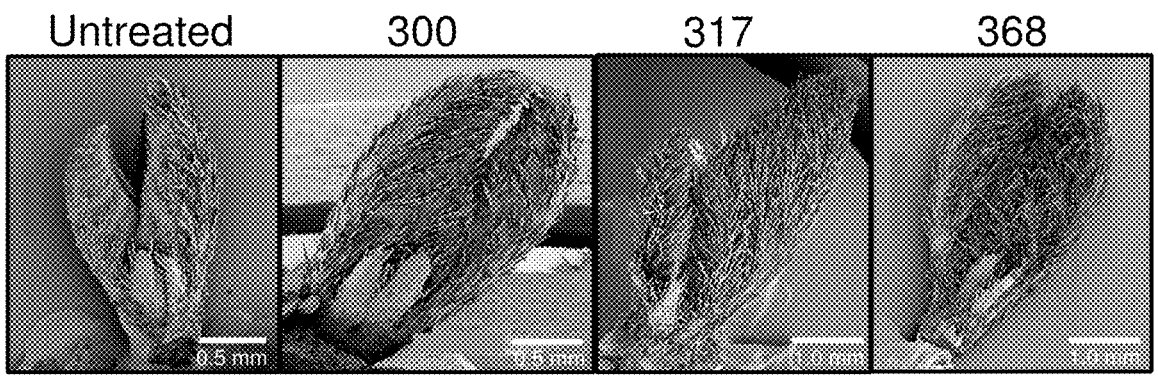
FIGS. 11A and 11B are Scanning EM (SEM) photographs showing that UV radiation suppresses hair growth (300 nm) and stimulates hair growth (317, 368 nm) in young soybean leaves.
Figure 11B:
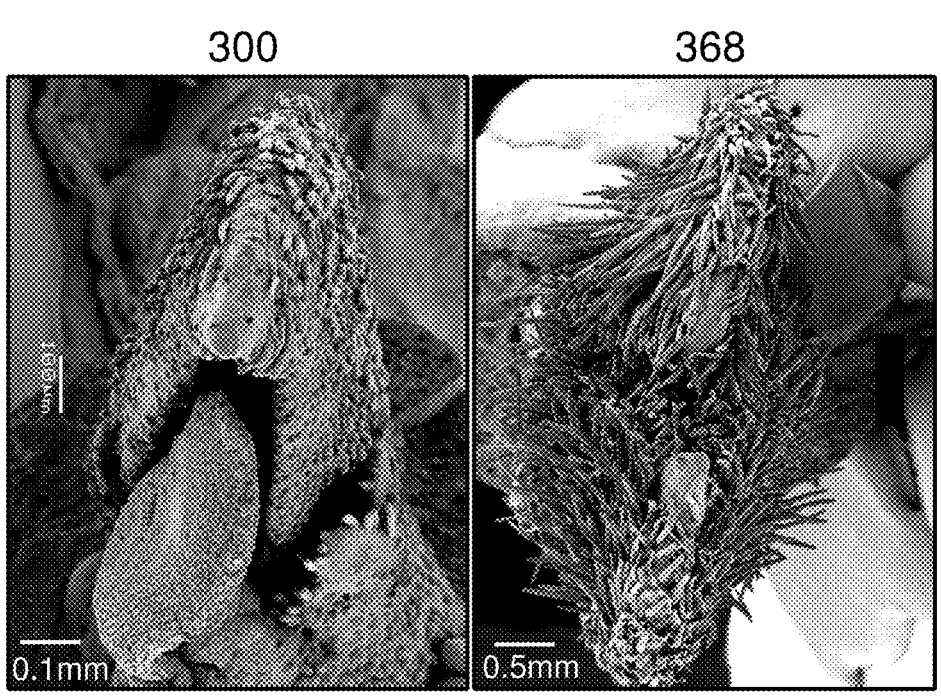
Figure 12:
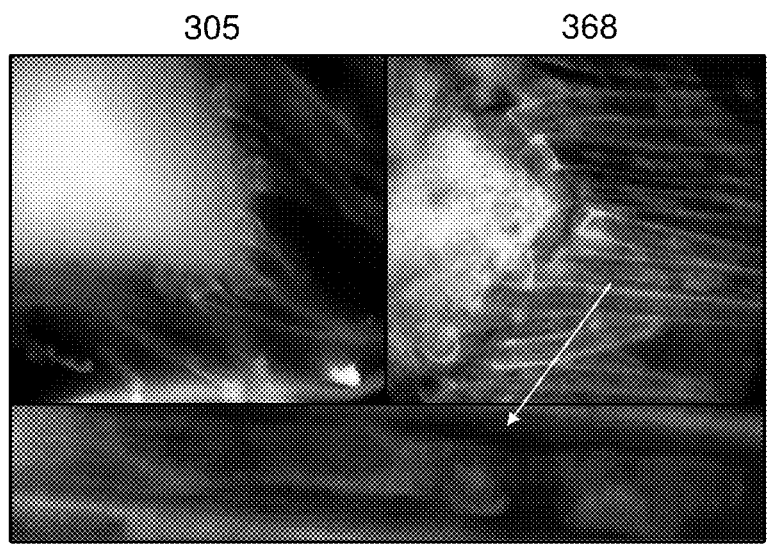
FIG. 12 is a pair of images showing natural fluorescence in the young leaves of soybean seedlings treated with 305 or 368 nm. The images shown are natural fluorescence and represent optical sections of the Z-stack focused at the adaxial epidermal surface of the cotyledon using DAPI, FITC, and Texas Red excitation blocking filter sets. The arrow points to an enlargement of a hair under the fluorescence microscopy.

Soybean Data:

Three varieties, Williams, Forrest, and Williams 82, serve as the progenitor germplasms used in many US soybean breeding programs. These germplasms were used in the experiments described in the Examples, and representative data is shown. In general soybean experiments are done using etiolated seedlings irradiated 3 days after planting or 7 days after planting, in contrast to the regime (6 days dark growth) used for *Arabidopsis* experiments. For the soybean experiments we have used a high intensity light source filtered through narrow band pass for a low fluence radiation dose of ($10^4$ μmol m$^{-2}$), with (10 nm half band width) filters of peak pass-through at 300, 305, 311, 317, 325, 332 and 368 nm. Soybean primary leaves are sensitive to UV, with the greatest damage occurring in response to irradiation with the greatest energy (smallest wavelength). Three day old etiolated wild type Williams, Forest and Williams 82 soybean seedlings of were individually irradiated with a single low fluence pulse of 300, 305, 311, 317, 325, 332, 368 nm or no light (as a control). After irradiation seedlings were maintained in a summer day-night cycle (14 hr white light: 10 hr dark) to allow for photoreactivation and other forms of light mediated repair until day 8. Irradiation with 300, 305 or 311 nm light results in a "severe" damage with a greater then 70% mortality rate by day 8 (FIGS. 9,10). Irradiation with 317 or 325 nm results in a 'moderate' response, with a mortality of approximately 20%. Irradiation with 332 and 368 nm did not cause appreciable death or cessation of growth by day 7 as compared to untreated germinating seeds. Returning the seedling to complete darkness rather then the light-dark cycle, amplifies the lethal effects of UV such that 300, 305, 311, 317 and 325 nm all effectively proves lethal. In a separate experiment seedlings were transplanted to soil immediately following UV treatment for use in long-term growth studies. Seedlings irradiated with 300, 317 or 368 nm light, or no UV light (as a control) were assessed 3, 7, 14, 21 and 28 days post planting. Irradiation with 300 or 317 nm resulted in approximately 25% mortality by 21 days post planting in all varieties tested. Examples of plants at 21 days post-planting are shown in FIG. 9. One example of a long term growth character is the average height of the plant. Unirradiated Williams will have an average height of 35.95 cm (14.2+1 inches) at 28 days post planting while plants surviving the 300 nm irradiation have an average height of 29.9 cm (11.8+1.5 inches). The SEM data show the surface characteristics of the developing primary leaf pairs (FIG. 11). The primary leaves of the seedlings treated with 317 nm and 368 nm light appear to expand to twice the size of the unirradiated controls suggesting a photomorphogenic response to the UV light. Most striking is the proliferation of fully developed and densely packed hairs, suggesting a role for the hairs in UV protection (FIGS. 11, 12). The fluorescent microscopy discussed below confirms the presence of UV absorbing pigments in the hairs (FIG. 12). Fluorescent microscopy reveals evidence of phenylalanine-derived pigments collecting in the hairs. Seedlings irradiated at 332 nm and 368 nm, but not more energetic wavelengths have pigments forming in the hairs that coat the primary leaves (FIG. 12), indicating a protective role for the hairs. Again, varieties with no hairs or few hairs would be sought to investigate the relationship between phenylalanine-derived products, hairs and protection from UV radiation. Exogenous phenylalanine can prevent even the most severe UV damage to plants—death. In order to determine if exogenously added phenylalanine can, as it does in *Arabidopsis*, allow for enhanced protection from UV damage in soybean, duplicate sets of seeds from each of the three varieties were planted identically to those used in the germination studies described above, with the media in one set supplemented with 1 mM of the amino acid phenylalanine. Three days after planting, seedlings (+ or − phenylalanine) were irradiated with a low fluence dose of 300 nm, 305 nm, 311 nm, or 317 nm light or no light (as a control) and then placed into normal day-light cycles for seven days. The sample data shown in FIGS. 13 and 14 indicate that the addition of phenylalanine to the growth media was able to ameliorate the most negative of the effects of high energy UV—namely lack of seed development and seed death. The very young seedlings were able to use the phenylalanine in the growth media to supplement the limiting amounts available in the seed to produce a larger quantity of UV screening pigments, and perhaps other compounds important to UV protection, thereby protecting themselves against the UV itself and perhaps enacting enhanced repair functions after the UV irradiation. Long-term studies also indicate that phenylalanine serves a protective role to the plant in permitting the plant to achieve adult stage and seed set (FIG. 15). Given that other branches of the phenylpropanoid pathway produces compounds important to other stress tolerances, the simple addition of phenylalanine may also confer protection against a host of stresses, including soybean cyst nematode (SCN).

Plant Transformation:

In preparing the constructs, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the coding sequence inserted into plant cells is dependent upon the influence of endogenous plant DNA adjacent to the insert. Generally, the insertion of heterologous genes appears to be random using any transformation technique; however, technology currently exists for producing plants with site specific recombination of DNA into plant cells (see WO 91/09957). Any method or combination of methods resulting in the expression of the desired sequence or sequences under the control of the promoter is acceptable.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, *Virology*, 54(02):536 539, 1973; Zatloukal, Wagner, Cotten, Phillips, Plank, Steinlein, Curiel, Bimstiel, Ann. N.Y. Acad. Sci., 660:136 153, 1992); Physical methods including microinjection (Capecchi, *Cell*, 22(2):479 488, 1980), electroporation (Wong and Neumann, *Biochim. Biophys. Res. Commun.* 107(2):584 587, 1982; Fromm, Taylor, Walbot, *Proc. Natl. Acad. Sci.* USA, 82(17):5824 5828, 1985; U.S. Pat. No. 5,384,253) and the gene gun (Johnston and Tang, Methods Cell. Biol., 43(A):353 365, 1994; Fynan, Webster, Fuller, Haynes, Santoro, Robinson, *Proc. Natl. Acad. Sci.* USA 90(24):11478 11482, 1993); Viral methods (Clapp, *Clin. Perinatol.*, 20(1):155 168, 1993; Lu, Xiao, Clapp, Li, Broxmeyer, J. Exp. Med. 178(6):2089 2096, 1993; Eglitis and Anderson, Biotechniques, 6(7):608 614, 1988; Eglitis, Kantoff, Kohn, Karson, Moen, Lothrop, Blaese, Anderson, *Avd. Exp. Med. Biol.*, 241:19 27, 1988); and Receptor-mediated methods (Curiel, Agarwal, Wagner, Cotten, *Proc. Natl. Acad. Sci.* USA, 88(19):8850 8854, 1991; Curiel, Wagner, Cotten, Birnstiel, Agarwal, Li, Loechel, Hu, *Hum. Gen. Ther.*, 3(2):147 154, 1992; Wagner et al., *Proc. Natl. Acad. Sci. USA*, 89 (13):6099 6103, 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.*, 87:671 674) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

Agrobacterium-mediated transfer is a widely applicable system for introducing foreign DNA into plant cells because the DNA can be introduced into whole plant tissues, eliminating the need to regenerate an intact plant from a protoplast. The use of Agrobacterium-mediated plant integrating vectors to introduce DNA into plant cells is well known in the art. See, for example, the methods described in Fraley et al., 1985, Biotechnology, 3:629; Rogers et al., 1987, Meth. in Enzymol., 153:253 277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, Mol. Gen. Genet., 205:34; Jorgensen et al., 1987, Mol. Gen. Genet., 207:471.

Modern Agrobacterium transformation vectors are capable of replication in E. coli as well as Agrobacterium, allowing for convenient manipulations. Moreover, recent technological advances in vectors for Agrobacterium-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, Agrobacterium containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, Mol. Gen. Genet., 199:183; Marcotte et al., Nature, 335:454, 1988). Application of these systems to different plant species depends on the ability to regenerate the particular species from protoplasts.

Once the plant cells have been transformed, selected and checked for antigen expression, it is possible in some cases to regenerate whole fertile plants. This will greatly depend on the plant species chosen. Methods for regenerating numerous plant species have been reported in the literature and are well known to the skilled artisan. For practice of the present invention, it is preferable to transform plant cell lines that can be cultured and scaled-up rapidly by avoiding the generally lengthy regeneration step. In addition the use of plant cell cultures avoids open field production and greatly reduces the chances of gene escape and food contamination. Tobacco suspension cell cultures such as NT-1 and BY-2 (An, G., 1985 Plant Physiol. 79, 568 570) can be used because these lines are particularly susceptible to handling in culture, are readily transformed, produce stably integrated events and are amenable to cryopreservation.

Many plant cell culture techniques and systems ranging from laboratory-scale shaker flasks to multi-thousand liter bioreactor vessels have been described and are well know in the art of plant cell culture. See for example Fischer, R. et al, 1999 Biotechnol. Appl. Biochem. 30, 109 112 and Doran, P., 2000 Current Opinions in Biotechnology 11, 199 204. After the transformed plant cells have been cultured to the mass desired, they are harvested, gently washed and placed in a suitable buffer for sonication. Many different buffers are compatible with the present invention. In general the buffer is an aqueous isotonic buffered salt solution at or near a neutral pH value that does not contain any detergent. Preferred buffers include Dulbecco's Phosphate Buffered Saline and PBS containing 1 mM EDTA.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Example 1

The Biosynthetic Pathway, and Regulatory and Feedback Systems Responsible for the Synthesis of Phenylalanine in Etiolated Soybean Seedlings Four main experiments are to be carried out: 1. Confirming the presence of cytosolic prephenate dehydratase activity in etiolated soybean and its role in phenylalanine synthesis. 2. Determining the effects of ABA and BL treatment on the activity of cytosolic prephenate dehydratase in etiolated soybean. 3. Characterization of the biochemical feedback effecting cytosolic prephenate dehydrates activity in etiolated soybean. 4. Determining if G-proteins have a role in the BL or ABA regulation of cytosolic prephenate dehydrates activity in etiolated soybean.

In order to confirm the presence of cytosolic prephenate dehydratase activity in etiolated soybean and its role in phenylalanine synthesis, the following experiments are conducted.

Developing primary leaves from seven-day-old dark-grown soybean seedlings were harvested into a pre-chilled extraction buffer consisting of potassium phosphate buffer (pH 7.5; 50 mM), DTT (1 mM), and plant protease cocktail (1:250; Sigma), homogenized for 60 sec at a setting of #6 in a Polytron followed by centrifugation to remove debris. This supernatant can be used as a crude extract directly in the assays described below or can be subjected to ultracentrifugation to remove any remaining debris and organeller material. All steps are carried out at 4° C.

These cytosolic extracts described above are tested for prephenate dehydratase activity; the ability to convert prephenate to phenylpyruvate, as well as the ability to convert phenylpyruvate to phenylalanine, and the absorbance and stability characteristics of phenylalanine and subsequent pigments as described above. Reactions are initiated with the addition of prephenate (Sigma) and terminated by the addition of an equal volume of 2 N NaOH. Production of phenylpyruvate and phenylalanine are determined spectrophotometrically, and can be confirmed by HPLC. All initial assay conditions, concentrations of substrate and length of assay are as discussed above and adjusted as needed.

We have determined that treatment of etiolated *Arabidopsis* with ABA, or BL results in an increase in the level of cytosolic PD1 activity, that the increase is the result of increased PD1 enzymatic activity and not simply an increase in the amount of PD1 protein, and that the activation of PD1 occurs as a result of a specific, direct physical interaction between PD1 and activated GPA1. From our collected data from soybean responses to BL and UV, it is likely that the same regulatory system exists in soybean.

To determine if ABA and/or BL treatment can change the cytosolic levels of prephenate dehydratase activity, 7 day old etiolated soybean are subjected to low fluence BL treatment or exogenously applied ABA as described above or no treatment as a control. All plants are returned to complete darkness for two hours after which cytosolic extracts are prepared and assayed as described infra.

L-Leucine and L-methionine are activators of the prephenate dehydratase activity. Our data using *Arabidopsis* cytosolic extracts indicates either amino acid can activate PD1 approximately 3-fold. Conversely, tyrosine and phenylalanine inhibit prephenate dehydratase activity in bacteria and fungi.

Extracts derived from untreated and BL or ABA treated 7 day old *Arabidopsis* (and other plants) were tested for prephenate dehydratase activity as a function of exogenously added leucine, methionine, tyrosine and phenylalanine (Warpeha et al., Plant Physiol. 143:1590-1600). Both L and D racimers are tested with the latter serving as a biologically inactive control. Various times of pre-incubation, and concentration and combination of amino acids for effects on prephenate dehydratase activity are tested. Absorbance and stability characteristics are tested at different pH concentrations between 6.8-8.0. Absorbance and stability characteristics are tested at different temperatures and durations of storage on the pigments and phenylalanine characteristics in solution for *Arabidopsis* and this is done for all crop plant types tested.

Determining if G-proteins have a role in the BL or ABA regulation of cytosolic prephenate dehydrates activity in etiolated soybean: our published data for *Arabidopsis* confirm that BL and ABA regulation of phenylalanine synthesis in etiolated *Arabidopsis* is directly dependent on a signal transduction chain consisting of GCR1 (a G-protein coupled receptor), GPA1 (the sole Gα subunit coded within the *Arabidopsis* genome), and PD1 (a cytosolic member of the prephenate dehydratase family whose activity is up-regulated through physical interaction with activated GPA1). If BL and/or ABA regulation of prephenate dehydratase activity is observed in soybean, whether or not regulation in soybean is G protein-mediated is determined.

Soybean is known to have two Gα-proteins, SGA1 and SGA2. The same procedures outlined above for defining the ability of purified and pre-activated GPA1, but not pre-inactive GPA1, to increase the enzymatic activity of PD1 are used. A HIS-tag or other maker tagged SGA1 and SGA1, produced using in vitro-coupled transcription, translation, is purified by the appropriate means and subsequently activated or inactivated by incubation with the appropriate GTP analog.

Cytoplasmic extracts of seven day old etiolated soybean extracts are obtained as described above. Purified SGA1 or SGA2, previously incubated with GTP, GDP, GTPβ-S (a non-hydrolysable analog of GDP which acts as a permanent Gα inhibitor), GTPγ-S (a non-hydrolysable analog which acts as a permanent Gα activator), or no nucleotide, is added to the cytoplasmic extract prior to initiation of the prephenate dehydratase assay. Prephenate dehydratase assays are conducted as described.

A crude soybean cytoplasmic extract is tested as the prephenate dehydratase activity source, rather than a pure protein as is the case for PD1 from *Arabidopsis*. Once the proteins are purified, experiments are conducted to identify interactions between proteins in the cytoplasmic extract and SGA1 and/or SGA2.

In another approach, cDNA is obtained for the different potential prephenate dehydratase proteins in soybean, especially those that are predicted to be or are potentially cytoplasmic. The protein is then expressed and purified. This allows for the examination of a direct activation of the soybean PD1-like protein by co-incubation with pure SGA1 and SGA2.

Example 2

Metabolites Made from Phenylalanine Used in Screening/Protection Against UV Radiation The regulation of phenylalanine and the metabolites made from phenylalanine in young *Arabidopsis* and soybean seedlings that are utilized in protection from UV radiation are identified and characterized. Some pigment(s) made in response to UV radiation have been identified that may be used to screen young etiolated seedlings from UV. These pigments are analyzed by HPLC & LC-MS methods. The pigments include anthocyanins, coumarin-related compounds and hydroxylcinnamate-related compounds. The comparisons needed to establish these correlations can be achieved through two non-overlapping means—the use of mutants or varieties that are known to have differing sensitivities to UV and the use of specific environmental conditions (e.g. BL or UV or ABA treatment, or the addition of phenylalanine or tyrosine to the growth media or externally to the plant surface) that result in an altered sensitivity to UV radiation. As indicated these can be used separately or in conjunction with each other (e.g. the use of PD1 to test the efficacy of phenylalanine in producing screening pigments). We will use a battery of analytical techniques to ascertain the phenylpropanoid derived compounds present as a result of any mutation or altered biochemical pathway.

Methods:

The primary leaves of soybean or the cotyledons of *Arabidopsis* are harvested into liquid nitrogen and subsequently prepared for absorbance, NMR, LC-MS or HPLC inclusive. Identification of specific compounds based on the output of these analytical methods requires a set of standards. We have built a strong library of standards comprised of compounds known to be produced as a function of the major areas of the phenylpropanoid pathway. We are using an "integrated" approach where pigments, proteins and key structures can be grouped and studied under various growth and genetic background conditions. Standards include but are not limited to: Anthocyanin, trans-Cinnamic Acid, p-coumaric Acid, Suberic Acid, 3-Hydroxycinnamic Acid, Flavanone, Sinapyl Alcohol, Sinapic Acid, 3,5-dimethoxy-4-Hydroxycinnamic Acid, Malonyl Dichloride (control), Phenylalanine and Phenylalanine Ammonia-Lyase (protein).

A "subtractive" analysis is used to compare the pigment content present in seedlings with either different genetic composition (mutants, varieties), and/or exposed to different conditions (e.g. treatment with ABA or BL, various media supplements such as phenylalanine or tyrosine) to determine if the presence or quantity or modifications of certain compounds correlate with sensitivity to a specific set wavelengths within the UV range.

Establishing a correlation between quantity and quality of UV radiation and a specific quantitative trait: UV sensitivity is assayed by irradiating 7 to 8-day-old etiolated *Arabidopsis* or soybean with either 300 nm, 317 nm or 368 nm. If desired, we can test for sensitivity to approximately 7 wavelengths between 300 and 368. We will attempt to use a minimum of traits for correlation purposes. Our initial work is and will be done using death (either as lack of germination or as post germination lethality) as a quick way to screen through many of the available mutants from public and private sources. Height of the plant or germination can be used as a second and more quantitative trait can be used to compare with the levels of potential screening compounds.

The use of specific environmental conditions that result in an altered sensitivity to UV radiation: our data demonstrate that BL or ABA treatments can result in a lower sensitivity to UV radiation in etiolated *Arabidopsis* and soybean seedlings, than do seedlings not receiving these treatments. The same is to be true of adding phenylalanine to the growth media. We have not yet measured the response to UV as a function the addition of other amino acids known to have a role in regulating prephenate dehydratase, and we are in the process of testing other exogenous applications of phenylalanine other than adding directly to the soil/growth media by root uptake. These specific growth conditions can be used with either *Arabidopsis* or soybean, and either wild type or mutant seedlings.

The Use of Genetic and Varietal Tools.

Soybean has a number of varieties that show some degree of UV resistance, although UV treatments can vary extremely in terms of dose, thus we will test varieties under our very low fluence conditions first in a preliminary screen. Varieties that show sensitivity to UV are retained for more detailed testing of responses to UV and exogenous regulators. Of particular interest are varieties with fewer hairs on young developing leaves, as it has been observed that one of the key features of sensitivity to UV is that the hairs that coat the young leaves completely by Day 8 of etiolated growth seem critical for UV resistance or protection. Varieties with few hairs or hairless appear susceptible to predation and this may be due to affects on the phenylpropanoid pathway, critical for defense response for predation as well as UV responses. As isoline of hard soy with dense hairs was tested vs. hard soy with few (glafrous) hairs. A correlation was found between hair density and UV sensitivity as the glafrous variety was badly damaged by small amounts of UV; phenylalanine can correct these deficiencies (see FIG. 19).

We can take advantage of the strong genetic and molecular genetic capacity of *Arabidopsis* and many identical features of the response to UV. We will examine the current catalog of mutants characterized as UV sensitive or UV insensitive. Similarly we can obtain and screen T-DNA insertion mutants effecting genes that code for phenylpropanoid pathway related activities. Given that there are hundreds of such genes, a screening hierarchy is developed. We would first test mutants at the branch point defining each of the four major sub-areas of the phenylpropanoid pathways for UV sensitivity. Those sub-areas showing a change in sensitivity would become targets for future iterations. At each stage we would examine the products present or absent from the mutants affecting UV sensitivity. The PD mutant lines, pd1-1 and pd1-2 are both T-DNA insertion mutants and both have an increased sensitivity to UV, hence they will be included in the afore-described pool.

Use of Pd1-1 and Pd1-2, to Assess Functions of Phenylalanine in Physiology and Screening of Plants.

We can also take advantage of these mutants and their homologs complete lack of phenylalanine (synthesized or existent) in the dark, and heightened sensitivity to UV and search for second site suppressors of that sensitivity. We can assess the effects of various forms of exogenous application of phenylalanine.

Our project focuses on the basic biochemistry of the initial synthesis and usage of phenylalanine particularly in the defense against UV radiation, an increasing problem in the environment. By understanding the genetics and basic biochemistry of this initial pathway, we can make the next step: which is to apply this knowledge to soybean and other plant breeding programs. Phenylalanine may have additional biochemical characteristics which can be exploited to provide external protection to plants sensitive to UV. By exogenous application of phenylalanine in solution it may be possible to apply a method of "sunscreen" to the plant surface in addition to providing a source of phenylalanine via root uptake in the soil/media.

Example 3

*Arabidopsis* Seedlings have Functional Prephenate Dehydratase Activity, and Phenylalanine Itself Appears to be a Stabilizing Factor in Solutions with Pigments and Other Compounds We have developed an assay that can be used to measure prephenate dehydratase activity in *Arabidopsis* extracts.

Methods

Plant Growth and Irradiations.

Six-day-old etiolated *Arabidopsis* seedlings (Col) were irradiated with a single short pulse of BL with a total fluence of $10^4$ μmols m$^{-2}$ [Folta and Kaufman, 2003; Warpeha and Kaufman, 1990], and/or UV (300, 317, 366 nm) at the same fluence, or ten-fold higher. UV-B treatments were as described by Warpeha et al. [2007]. Pre-irradiations of BL ($10^4$ μmols m$^{-2}$) were given at 2, 6 and 24 h prior to treatment with UV. Irradiated seedlings were returned to the darkness. Seedlings were harvested at 2 h, 6 h and 24 h post irradiation.

Preparation of General Extracts.

The aerial portions of six-day-old dark grown *Arabidopsis* seedlings were harvested into potassium phosphate buffer (pH 7.5; 50 mM), DTT (1 mM), and plant protease cocktail (Sigma), and homogenized for 60 sec at a setting of #6 in a Polytron. Cell debris was removed by centrifugation. All steps were carried out at 4° C. All plants types would be harvested by this method between 6-8 days after planting in darkness.

Measurement of Activity in Cell Free Extracts.

The reaction was initiated with the addition of prephenate and stopped with equal volume 2 N NaOH. Production of phenylpyruvate was determined spectrophotometrically. Preliminary experiments indicate that extracts had an average activity of 0.5 nmols of phenylpyruvate formed per mg protein per minute. See Warpeha et al., Plant Physiol. 140:844-855.

Results

A number of experiments were conducted with pre-incubation with L-Phenylalanine in various concentrations, where we demonstrated the reaction of producing phenylalanine itself was inhibited. Experiments were also conducted with L-Leucine or L-methionine, which resulted in an approximate 3-fold increase in activity measured (thus made more phenylpyruvate), but these did not increase stability of the solution over time over time.

In Vitro GPA1-PD1 Activation Assays with Phenylalanine.

Full-length GPA1 and PD1 templates were amplified, prepared and purified by the methods described (Lapik and Kaufman, 2003). GPA1 and PD1 proteins were individually produced by coupled in vitro transcription/translation using TNT T7 Coupled Wheat Germ Extract System (Promega; Madison, Wis.) as directed and as modified previously (Lapik and Kaufman, 2003). In vitro association assays were conducted by mixing approximately equimolar concentrations of GPA1 with PD1 in prephenate dehydratase assay buffer at 4° C. (Euverink et al., 1995) with modifications for plants: 50 mM $K_2PO_4$ pH 7.5, 1.0 mM DTT, 100 mM PMSF, 0.5% protease inhibitor cocktail for plants. "Activated" GPA1 was achieved by pre-incubation with 100 μM GTPγS (a non-hydrolysable GTP analog). "Inactivated" GPA1 was achieved by pre-incubation with GDP, or GDPβS (a non-hydrolysable GDP analog). At time "zero", prephenate at concentration of 10.0 mM (final concentration 1.0 mM) dissolved in 50 mM $K_2PO_4$ pH 7.5 (range tested 7.0-8.0 initially) was added to the reaction mixture. Reaction mixtures were stopped at time zero and various time points thereafter by adding 0.5 volume of 1N NaOH (Euverink et al., 1995). Absorbance values were read immediately afterwards at 320 nm to assess conversion of prephenate to phenylpyruvate as described in Euverink et al., (1995). For controls, activity assays with conditions such as buffer only, no protein, one protein (GPA1 or PD1) or GPA1+PD1+no Prephenate, were conducted in the same manner as described above.

Phenylalanine was included at a final concentration of 1 mM in the purified cell free extracts and the purified protein in vitro assays since it gave a reference point of absorbance in the UV range (~236 nm). Originally extracts were kept on ice up to 2 h, but it was noticed that when they were left in a cold box (+4° C. overnight) that the pigments had not degraded, even in tubes that were not protected by aluminum foil (i.e. exposed to light), the full absorbance spectra (200-800 nm) obtained were identical, indicating a very stable solution. Prephenate, a precursor of phenylalanine degraded at a rate of 15-18% for the first 30 minutes at room temperature, but phenylalanine in a buffered solution between pH 7.4-8.0 appeared to not degrade even for days at room temperature in laboratory lighting. Spectra remained stable at 24 h at room temperature or in +4° C. (shown in FIG. 16). If solutions containing extract plus phenylalanine were left at room temperature overnight exposed to the fluorescent lighting, the spectrum was reduced at some particular wavelengths but not significantly reduced. Extracts with prephenate only (no phenylalanine added) did degrade over the 24 h period at room temperature in lab lighting.

We then conducted two periods of testing cell free extracts with phenylalanine added whereby the "dark" extract was exposed to a $10^4$ μmols $m^{-2}$ up to $10^5$ μmols $m^{-2}$ of UV (366 nm) and spectra appeared unchanged from 5 h (where absorbance increased to a maximum level likely due to pigments made or "finished" from the UV treatment) until 24 h post irradiation. When the extracts were stored in the cold box (+4° C.) for 4 days, they remained unchanged with less than 10% deviation from initial 24 h post absorbance spectra.

Figure 16:
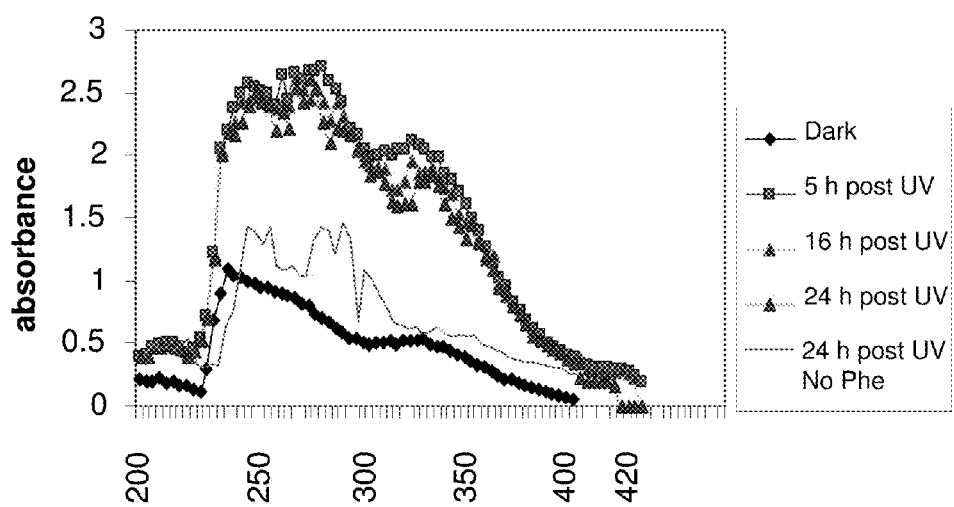
FIG. 16 is a graph showing the spectral absorbance of plant extracts. Extracts were made as described in Warpeha et al., Plant Physiol., 140:844-855. Cell free extracts were left at room temperature for 24 h after a $10^5$ μmolm$^{-2}$ treatment of UV (366 nm) in lab lighting (which is fluorescent). There is a clear difference in stability in the solution when phenylalanine is added versus solutions/extracts not containing phenylalanine.

Referring to FIG. 16, an example of these types of experiments is shown. Cell free extracts were left at room temperature for 24 h after a $10^5$ μmol $m^{-2}$ treatment of UV (366 nm) in lab lighting (which is fluorescent). It is clear that diluted extract solutions (in buffer) containing phenylalanine remain stable over time assayed (on the spectrophotometer) compared to solutions which did not have phenylalanine included during UV radiation.

Example 4

Phenylalanine Prevents UV Radiation Damage in Soybean

Figure 17:
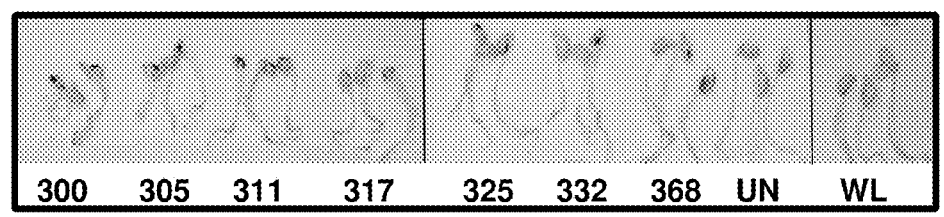
FIG. 17 is a series of photographs of seedlings showing that the soybean response to UV depends on wavelength. Seedlings that germinated and survived 5 d post-irradiation are shown.

Referring to FIG. 17, it was shown that the soybean response to UV depends on wavelength. Soybean were planted and maintained in complete darkness. On the third d after planting, germinating/etiolated seedlings were irradiated with a single pulse of low fluence UV of one of the following wavelengths: 300, 305, 311, 317, 325, 332, 368 nm or no UV (UN) or, a brief dose of white light ($10^4$ μmol $m^{-2}$; WL). After irradiation, seedlings were maintained in darkness for five d then photographed in white light. Only seedlings that germinated and survived five d past irradiation are shown (i.e. dead seeds/seedlings not shown).

Referring to FIG. 10, it was shown that the soybean response to UV depends on wavelength and white light "recovery." Soybean were planted and maintained in complete darkness. On the third d after planting, germinating/etiolated seedlings were irradiated with a single pulse of low fluence UV of one of the following wavelengths: 300, 305, 311, 317, 325, 332, 368 nm or no UV (Untreated) as described for FIG. 10, but instead of a 5 d dark period post UV treatment, they were returned to a 14:10 lt:dk cycle for up to seven d.

Referring to the SEM photographs of FIG. 11, it was shown that UV radiation suppresses hair growth (300 nm) and stimulates hair growth (317, 368 nm) in young soybean leaves. Seedlings of soybean were grown for seven d in complete darkness. Seedlings were mock-irradiated (Untreated) or irradiated with a brief pulse of UV (300, 317 or 368 nm), returned to the dark for 24 h. Primary leaves were harvested directly into fix intended for SEM.

Figure 18:
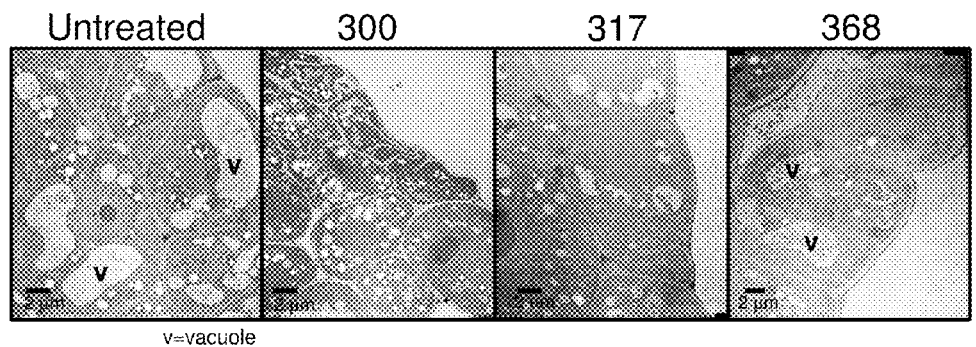
FIG. 18 is a series of transmission electron microscopy (TEM) photographs showing that high energy UV causes extensive internal damage to young soybean leaves.

Referring to FIG. 18, high energy UV causes extensive internal damage to young soybean leaves. Soybean were grown for seven d in complete darkness similar to the method of FIG. 17 (but in complete darkness). Seedlings were mock-irradiated with either no light (Untreated) or irradiated with $10^4$ μmolm$^{-2}$ of UV (300, 317 or 368 nm), then returned to the dark for 24 h after which the primary leaves were harvested directly into fixative in the dark, then processed for TEM. Sections were cut perpendicular to the adaxial surface, and representative sections are shown. v=vacuole. The TEM shows that the cells are significantly damaged by a brief treatment with 300 nm, with damage to the organelles and plasma membrane-cell wall interface.

Figure 19:
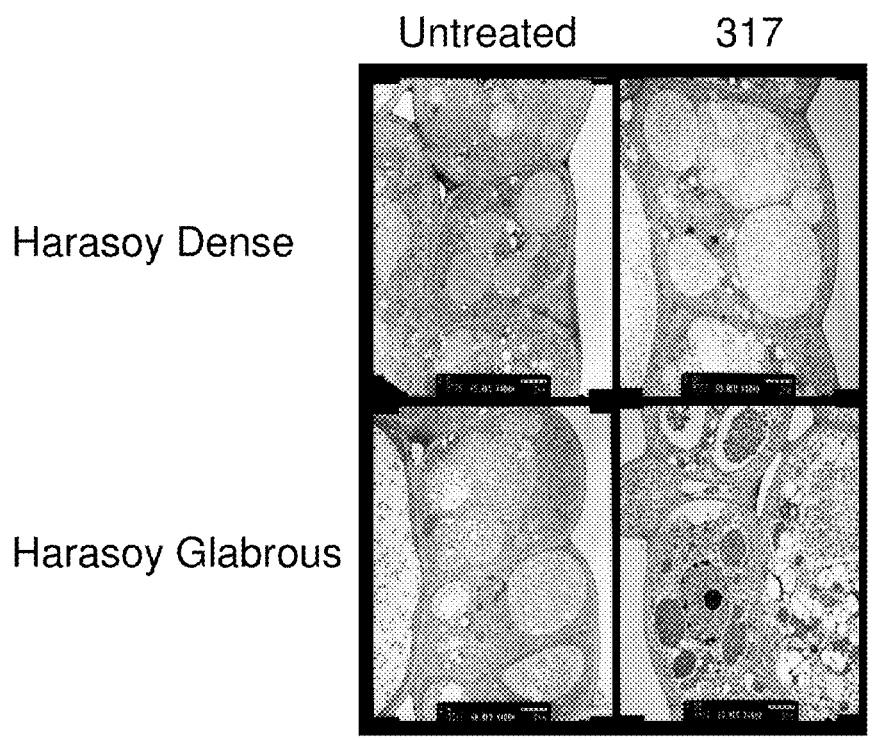
FIG. 19 is a series of TEM photographs showing that hair density does affect stability to shield from UV radiation.

Referring to FIG. 19, it was shown that hair density does affect the ability to shield from UV radiation. Isogenic lines of Harasoy "dense" (many hairs per area) and "glabrous" (few or no hairs per area) were used to see if hairs themselves directly assisted in protection from UV-B radiation. Seedlings were grown and treated in the same manner as that shown in FIG. 18, then the integrity of the internal structures assessed by TEM as shown in FIG. 18. The glabrous Harasoy was significantly damaged by a brief treatment with 300 nm, with damage to the organelles and plasma membrane-cell wall interface.

Referring to FIG. 12, natural fluorescence in the young leaves of soybean seedlings were treated with 305 or 368 nm. Seedlings of soybean were grown for seven d in complete darkness. Seedlings were mock-irradiated with either no light (untreated) or irradiated with $10^4$ μmolm$^{-2}$ of UV (305 or 368 nm), then returned to the dark for 24 h, after which the primary leaves were harvested and photographed on a deconvoluting microscope. Most of the fluorescent material is at the tip of the young leaves, most noticeably present in the hair outgrowths of the epidermal cells.

Figure 13:
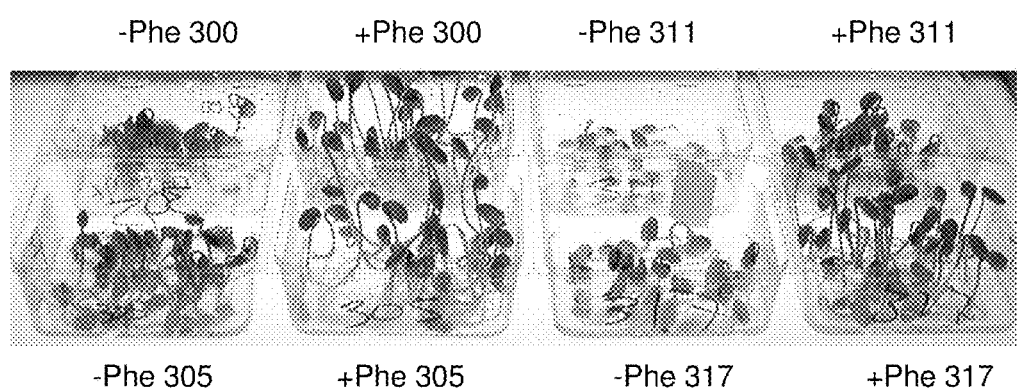
FIG. 13 is a photograph of seedlings showing that inclusion of Phe in the growth media restores growth characteristics regardless of UV wavelength. Seedlings were photographed from the diagonal/side view at seven days post-irradiation. Wavelength of treatment and + or − Phe is indicated.
Figure 14:
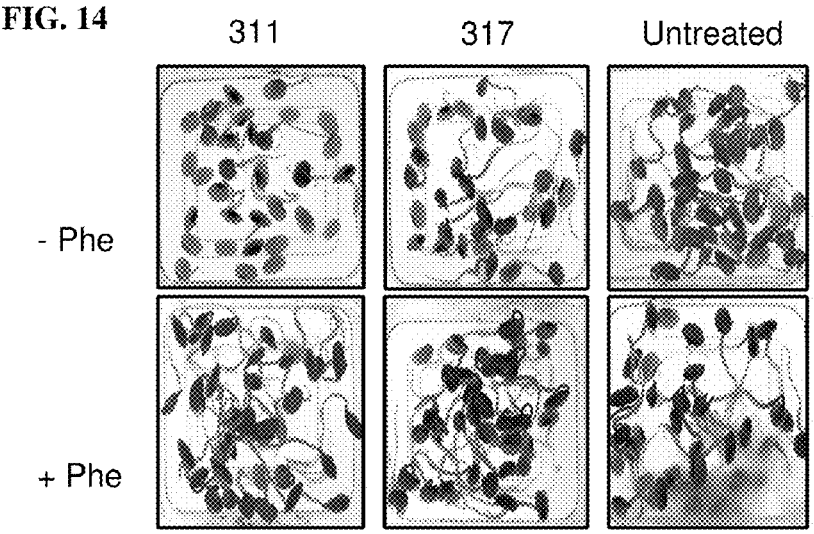
FIG. 14 is a series of photographs showing the growth response of soybean to UV 311 nm and 317 nm when Phe is included in media at 5 d past irradiation. Seedlings were grown identically to those described in FIG. 10, except that seedlings were grown on media with + and without −1.0 mM Phe. Seedlings were photographed in white light five d post-irradiation from overhead.
Figure 15:
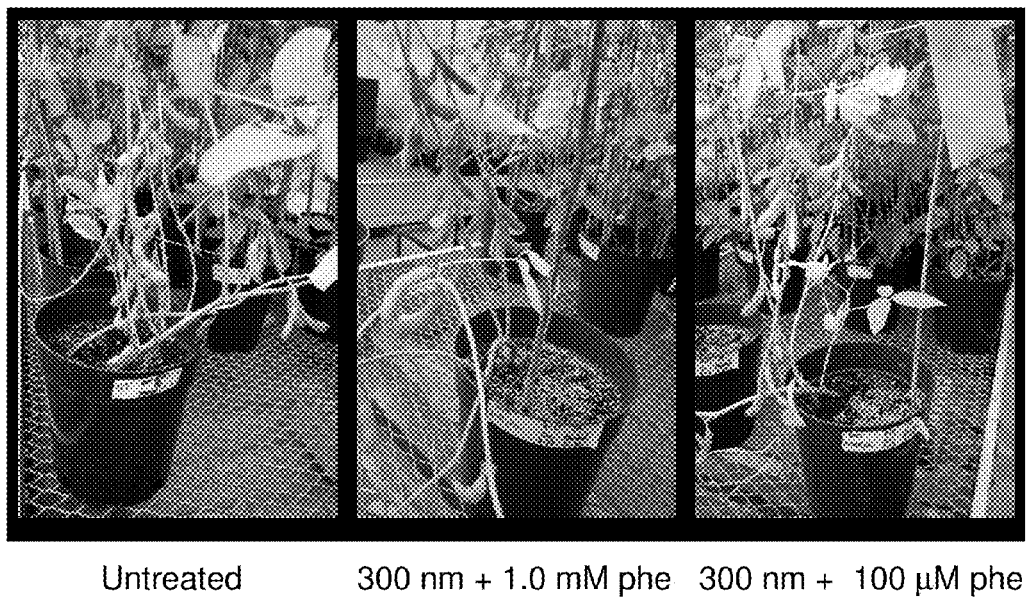
FIG. 15 is a series of photographs of plants showing the long-term growth response of soybean treated with 300 nm on day 3 after planting supplemented by Phe, e.g., reversal of the negative effects of UV-radiation.

Referring to FIGS. 13 and 14, it was shown that Phe can overcome the most deleterious effects of high energy UV in soybean. FIG. 14 shows the growth response of soybean to UV 311 nm, 317 nm when Phe is included in media at 5 d post irradiation. Seedlings were grown identically to that described in FIG. 17 except that seedlings were grown on media with (+) and without (−) 1.0 mM Phe. Seedlings were photographed in white light five d post-irradiation from overhead. FIG. 13 shows that inclusion of Phe in the growth media restores growth characteristics regardless of UV wavelength. Seedlings were grown identically to that described in FIG. 14 and photographed from the diagonal/side view at seven d post-irradiation. Wavelength of treatment and + or − Phe is indicated.

Figure 20:
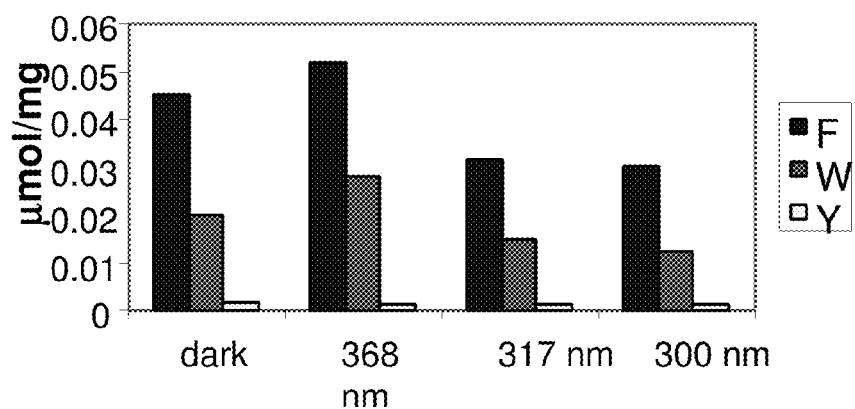
FIG. 20 is a graph showing the aromatic amino acid content of young soybean leaves after exposure to UV radiation where more energetic wavelengths damage soybean's ability to make phenylalanine.

Referring to FIG. 20, the amino acid content of young leaves after exposure to UV radiation was determined. Seedlings were grown for 7 d in complete darkness. On d 7 seedlings were irradiated with various wavelengths of UV as shown on the figure, then returned to darkness for 24 h, after which amino acids were extracted as described in Warpeha et al., (Plant Physiol. 140:844-855, 2006). 368 nm increases Phe and Tyr accumulation in young leaves, however all other UV wavelengths actually suppress Phe and Tyr. Trp seems to be generally unaffected by UV. This indicates that UV-A can aid in accumulation of Phe/Tyr to make defense chemicals but more energetic wavelengths are deleterious.

Figure 21:
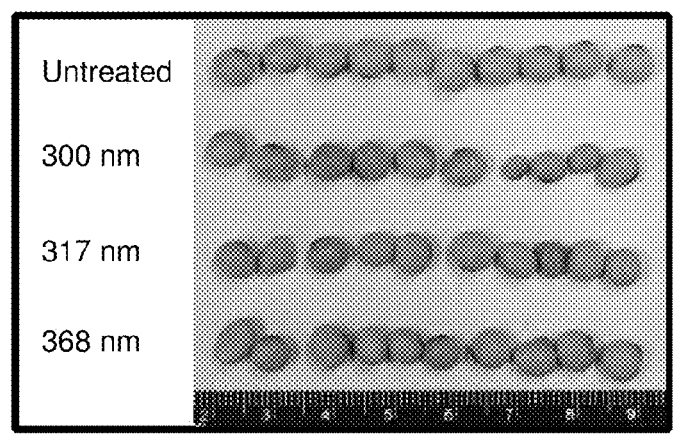
FIG. 21 is a pair of photographs of seeds showing the long-term growth effects on seed morphology. These representative seeds show some deformation and abnormality of seed production for seedlings treated with 300 nm or 317 nm in particular.
Figure 21:
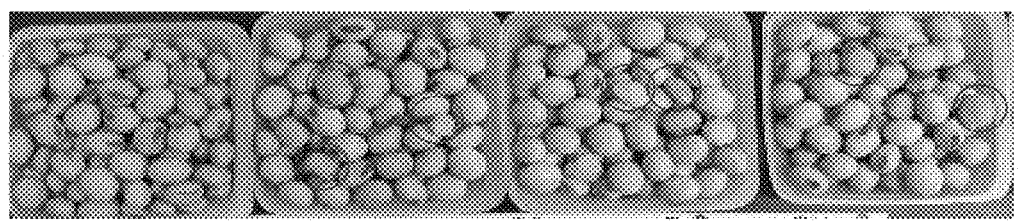

Referring to FIG. 21, seed morphology after long-term growth of soybean (exposed to UV radiation on day 3) was examined. Dark-grown seedlings were treated with different UV treatments on d 3 after planting them moved to regular day-night cycles until seed set. Seed was harvested and assessed for morphology and for yield. The photographs of representative seeds show some deformation and abnormality of seed production for seedlings treated with 300 or 317 nm in particular.

Figure 22A:
FIG. 22 is a series of photographs showing the long-term growth response of soybean seeds treated with 300 nm on Day 3 after planting supplemented by Phe, e.g., the reversal of negative effects of UV-radiation. This photograph of representative seeds (FIG. 22B) and corresponding plants (FIG. 22A) shows that phenylalanine can reverse the negative effect on yield of UV.
Figure 22B:
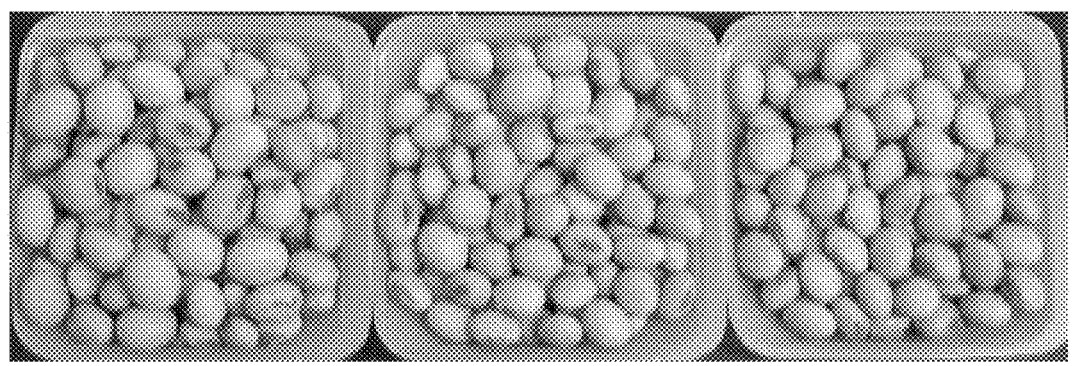

Referring to FIG. 22, it was shown that treating soybean with Phe reverses the negative effects of UV-radiation. Seedlings were grown identically to that described for FIGS. 13 and 14, where soybean were supplemented with Phe (+Phe) or not (−Phe). Soybean were grown to seed set in greenhouse conditions where growth characteristics and evaluation of pods and seeds occurred during and after ripening. The seed yield in quantity and in quality of plants given Phe supplements prior to UV treatment was indistinguishable from untreated seedlings i.e. Phe was able to restore normal seed development to UV-treated seedlings.

Metabolome studies on Soybean. The Williams variety of soybean was used for our preliminary standardizations of methods. On Day 6 after planting in darkness, separate growth trays of each variety were individually irradiated with 300 nm, 317 nm, 368 nm or no light (Dark i.e. control). After irradiation, seedlings were returned to darkness until harvest of the primary leaf material 24 h later. It took months to collect enough material to test all of the procedures in HPLC and LC-MS methods. Data is shown in Table 1. All chemicals listed on the left had to be standardized with pure chemicals first to adjust methods for identification and proper separation for when analysis was done on soybean material. Our initial observations are that 300 nm and 317 nm (both in UV-B region) seem to suppress protective pigment development (see Table I anthocyanins, 3-hydroxycinnamic acid) and production of Phenylalanine itself, the amino acid that is the precursor to the pigments (See FIG. 1), indicating that a main reason for the observed death of young plants by UV-B radiation in particular (Warpeha, K. M., Sullivan, J., Gibbons, J., Carol, A., Tree, R., Durham, W., Slusser, J., and Kaufman, L. S. (2007) Phenylalanine is the rate-limiting step for protection from atmospheric UV radiation damage in soybean (*Glycine max* L.) submitted 2008) is that young seedlings cannot make pigments due to suppression of phenylalanine production.

TABLE 1

Preliminary metabolome results of soybean etiolated seedlings treated with UV radiation. Analysis by HPLC and LC-MS and absorption.

| Metabolome compounds and substances | Dark | 300 nm | 317 nm | 368 nm |
|---|---|---|---|---|
| Anthocyanin | 1.0 | − | / | + |
| trans-Cinnamic Acid | 1.0 | * | * | * |
| Suberic Acid | 1.0 | * | * | * |
| p-coumaric Acid | 1.0 | * | + | + |
| 3-Hydroxycinnamic Acid | 1.0 | * | / | + |
| Flavanone | 1.0 | − | + | / |
| Sinapyl Alcohol | 1.0 | * | * | * |
| Sinapic Acid | 1.0 | * | + | / |
| 3,5-dimethoxy-4-Hydroxycinnamic Acid | 1.0 | * | * | * |
| Malonyl Dichloride (control) | 1.0 | / | / | / |
| Phenylalanine | 1.0 | − | − | + |
| Phenylalanine Ammonia-Lyase (protein) | 1.0 | * | * | * |

+ increase;
− decrease or no detection;
/ no change compared to Dark level;
* awaiting confirming data.
Untreated Plant Material = Dark which is set to value 1.0.

The long-term growth responses and yield of Williams treated with UV radiation are shown below in Table 2. Seedlings were treated on d 3 after planting with 300, 317 or 368 nm or untreated, then moved outside for normal day-night growth until seed set. Termination of seed development in seedlings treated with UV is the most prominent effect. Both the pod number and % aborted seeds/seed pods per plant is significantly different form Untreated seedlings. * indicates statistically significant.

TABLE 2

| Surviving plants to seed | n = 32 Untreated | n = 13 300 nm | n = 17 317 nm | n = 30 368 nm |
|---|---|---|---|---|
| Pod # per plant | 22.6 | 11.0* | 12.1* | 12.0* |
| Seed # per pod | 2.1 | 2.1 | 2.1 | 2.0 |
| % aborted seed pods per total pods | 3.0 | 8.0* | 7.2* | 4.5 |

The long-term growth responses and yield of Forrest treated with UV radiation are shown in Table 3. Seedlings were treated on d 3 after planting with 300, 317 or 368 nm or untreated, then moved outside for normal day-night growth until seed set. Termination of seed development in seedlings treated with UV is the most prominent effect. The % aborted seeds/seed pods per plant is significantly different form Untreated seedlings. * indicates statistically significant, where the 300 nm treatment for Forrest is highly statistically significant.

TABLE 3

Surviving plants to seed

| Surviving plants to seed | n = 21 Untreated | n = 9 300 nm | n = 14 317 nm | n = 14 368 nm |
|---|---|---|---|---|
| Pod # per plant | 40.8 | 43 | 38 | 44 |
| Seed # per pod | 2.1 | 1.9 | 1.8 | 1.9 |
| % aborted seed pods per total pods | 6.6 | 21.9* | 9.1* | 6.2 |

Example 5

The GCR1, GPA1, PRN1, NF-Y Signal Chain Mediates Both Blue Light and ABA Responses in *Arabidopsis*

Materials and Methods:
Plant Material:

Matched seed lots of wt col *Arabidopsis*, and siblings carrying T-DNA insertions within coding regions of these genes listed in Table 3. The accessions were obtained from the *Arabidopsis* Biological Resource Center (Alonso et al., (2003) *Science* 301: 653-657) or from the *Arabidopsis* Knockout Facility, University of Wisconsin, Madison. All lines used herein are in the col background except for pir1-1 (Lapik and Kaufman, (2003), *Plant Cell*, 15: 1578-1590) and CS6539 which are in the ws background. Seeds stocks were obtained from plants grown in Scott Metromix 200 in continuous white light. All seeds are homozygous for the reported insertion except for accessions of NF-Y-B9 (all accessions; Kwong et al., (2003), *Plant Cell* 15: 5-18; Lee et al., (2003), *Proc. Natl. Acad. Sci* 100: 2152-2156) and the pir1-1 (in the ws background only; Lapik and Kaufman, (2003) *Plant Cell*, 15: 1578-1590), as they are embryonic lethals. Where available, T-DNA seed lines with insertions located in the promoter (approx. 600-680 by upstream from the coding region; GPA1: SALK__057120, SALK__59035) were also tested. All homozygous insertion seeds appear to represent null mutants based on RT-PCR data.

BL and ABA Treatment/Northern Analysis:

Six-d-old dark-grown *Arabidopsis* seedlings col wild type or insertion mutants were grown on 0.8% agarose plates containing only 0.5× Murashige and Skoog media as described in Lapik and Kaufman (2003). The growth media contains no additional sugar, hormones, vitamins or other nutrients. Seedlings were irradiated with a single pulse (10 s) of low fluence BL (total fluence of $10^2$ μmol m$^{-2}$); or a single pulse (100 s) of saturation fluence BL (total fluence of $10^4$ μmol m$^{-2}$); or no light (DK), and/or, treated with 800 nM ABA dissolved in ethanol, or ethanol alone, placed back in the dark for two h after which total RNA was extracted and used for northern blot analysis (Lapik and Kaufman, 2003). Lhcb and rDNA probes used, quantitation methods, and means of normalization to rRNA levels are described elsewhere (Marrs and Kaufman, (1991) *Planta* 183: 327-333). Induction ratios (BL/DK or ABA/ETOH or BL+ABA/ETOH) derive from at least three independent replicates. All induction data is correct for loading through the quantitation of the rRNA as described (Warpeha and Kaufman, (1990) *Planta* 182: 553-558). Error bars represent standard error of the mean. Real time quantitative PCR (qPCR) was used to measure the level of Lhcb RNA induction in response to a single pulse of low fluence blue light as a confirmation of the Northern blot analysis methods. This PCR was performed using iCycler protocols and the SYBR kit from Invitrogen (Carlsbad, Calif.; first strand synthesis from RNA & real time PCR) from Wild Type untreated (Dark or DK) and BL treated seedlings. The qPCR-derived information (4 different RNA sets of Dark and BL-treated) data was analyzed using (ΔΔCoT). The resulting range of BL induction is 1.54-2.19. This compares well to the induction level range in replicates we observe using Northern analysis (1.40 to 2.18). The Student's T-Test indicates that the P-value for the BL induction levels by comparing the two methods (Northern vs. PCR) is 0.526; similarly the P-value for the DK controls is 0.765, so the range/means of the two methods are not different (95% confidence level). Thus, the Northern blot method of analysis is a good indicator of induced gene expression.

TABLE 4

Tested accessions of null T-DNA insertion lines for potential BL-induced Lhcb signal transduction pathway components.

| Protein | Gene | Accession |
|---|---|---|
| NF-Y-A1 | At5g12840 | SALK_047351 |
| NF-Y-A2 | At3g05690 | SALK_146170 |
| NF-Y-A3 | At1g72830 | SALK_067992 |
| NF-Y-A3 | At1g72830 | SALK_068206 |
| NF-Y-A4 | At2g34720 | SALK_003337 |
| NF-Y-A4 | At2g34720 | SALK_003338 |
| NF-Y-A5 | At1g54160 | SALK_006559 |
| NF-Y-A5 | At1g54160 | SALK_042760 |
| NF-Y-A6 | At3g14020 | SALK_028169 |
| NF-Y-A6 | At3g14020 | SALK_005942 |
| NF-Y-A7 | At1g30500 | SALK_020063 |
| NF-Y-A7 | At1g30500 | SALK_121158 |
| NF-Y-A9 | At3g20910 | SALK_002235 |
| NF-Y-B1 | At2g38880 | SALK_038840 |
| NF-Y-B1 | At2g38880 | SALK_109993 |
| NF-Y-B2 | At5g47640 | SALK_025666 |
| NF-Y-B2 | At5g47640 | SALK_105664 |
| NF-Y-B3 | At4g14540 | SALK_130295 |
| NF-Y-B3 | At4g14540 | SALK_130295 |
| NF-Y-B4 | At1g09030 | SALK_123845 |
| NF-Y-B6 | At5g47670 | SALK_118236 |
| NF-Y-B6 | At5g47670 | SALK_118238 |
| NF-Y-B7 | At2g13570 | SALK_085886 |
| NF-Y-B8 | At2g37060 | SALK_108199 |
| NF-Y-B9 | At1g21970 | SALK_000450 |
| NF-Y-B9 | At1g21970 | SALK_021549 |
| NF-Y-C1 | At3g48590 | SALK_086334 |
| NF-Y-C4 | At5g63470 | SALK_032163 |
| GCR1 | At1g48270 | SALK_027808 |
| GCR1 | At1g48270 | CS6539 |
| GPA1 | At2g26300 | SALK_066823 |
| GPA1 | At2g26300 | SALK_001846 |
| GPA1-pro | At2g26300 | SALK_059035 |
| GPA1-pro | At2g26300 | SALK_571120 |
| PRN1 | At3g59220 | SALK_006939 |
| PRN1 | At3g59220 | Pir1-1 |

RT-PCR Experiments:

RNA of dark-grown or light-grown six-day-old *Arabidopsis* was extracted as described in (Warpeha and Kaufman, 1990). First strand and PCR synthesis was achieved by using SuperScript™ First-Strand Synthesis System for RT-PCR (Invitrogen, Carlsbad, Calif.). PCR results were confirmed with Invitrogen High Fidelity PCR kit. Gene specific primers were obtained by comparing sequence via BLAST and selecting 18- to 23-mers which were specific to each NF-Y subunit (IDT, Ames, Iowa). Results were visualized by ethidium bromide staining.

ABA Hypersensitivity Germination Experiments:

Matched seed lots were planted as described for northern blot assays, except that the media was supplemented with ABA (Sigma, St. Louis, Mo., USA) ranging from 0 nM up to 1000 nM (Lapik and Kaufman, 2003). Seedlings were grown at 22° C. in continuous white light. Germination was measured as described previously (Lapik and Kaufman, 2003), assessed visually on a daily basis, and photographed seven d post-stratification.

In Vitro Protein Association Assays:

Full-length PRN1 was subcloned into the GST-fusion expression vector pGEX-4T-1 (Amersham Pharmacia Biotech, Piscataway, N.J., U.S.A.), prepared, expressed and purified as described (Lapik and Kaufman, 2003). Radiolabeled NF-Y-B9 and NF-Y-B6 protein was produced by coupled in vitro transcription/translation using TNT T7 Coupled Wheat Germ Extract System (Promega, Madison, Wis., U.S.A.) as directed and as modified (Lapik and Kaufman, 2003). In vitro association assays were conducted as described previously (Lapik and Kaufman, 2003). Samples were resolved on 4-20% gradient SDS-PAGE gels. Results were visualized using a Phosphor-Imager™ (Molecular Dynamics, Sunnyvale, Calif., U.S.A.; Lapik and Kaufman, 2003).

Yeast Two-Hybrid Experiments:

The potential for interaction between PRN1 and either NF-Y-B9 or the closely-related protein NF-Y-B6 was tested in a yeast two-hybrid assay as described (Lapik and Kaufman, 2003). Bait and prey vectors, pGBT9 and pGAD424, respectively, were obtained from Clontech (Palo Alto, Calif., U.S.A.), and used as directed. The indicated combinations of the bait (pGBT9) and prey (pGAD424) constructs were transformed into the yeast reporter strain AH109. The same inserts were also cloned in the opposite vectors (bait and prey switch) with similar results. Empty vector (pGAD424), and the yeast mating response protein, yFUS3, were used as negative bait controls. Other negative controls included NF-Y-B9 and NF-Y-B6 with empty prey vector. The interaction between the yeast Gα (yGPA1) and Gβ (ySTE4) was used as a positive interaction control. Initial transformants were plated on 9 cm SD plates (Trp$^-$, Leu$^-$, Lys$^-$, His$^-$) to select for histidine prototrophy. Positive transformants were also streaked on X-α-Gal-containing, selective media where LacZ reporter gene activity was monitored visually; blue color indicating a positive interaction.

Results

GCR1, GPA1, and PRN1 are Required for BL-Induction of Lhcb:

We have previously demonstrated that PRN1 can act as an effector for GPA1 in a signaling mechanism that acts to inhibit the ABA-induced delay in seed germination (Lapik and Kaufman, 2003); the two proteins can interact and mutants in both share the same phenotype. It has been shown that GPA1 can interact with GCR1 (Pandey and Assmann, (2004), Plant Cell 16: 1616-1632), and later confirmed that GCR1 and GPA1 were in a direct signaling mechanism affecting germination and early development (Pandey et al., (2006), Plant Physiol 141: 243-256). We have identified a positive signaling link between GCR1 and GPA1 regarding their shared role BL and ABA-induced activation of PD1 in the etiolated cotyledon, the immediate production of phenylalanine, and subsequent production of products of the phenylpropanoid pathway (Warpeha et al., (2006), Plant Physiol 140: 844-855).

We sought to determine if GCR1, GPA1 and PRN1 have defined roles in the immature cotyledon, namely induction of Lhcb expression by the BLF System. Six day-old etiolated wt (col) and multiple T-DNA insertion mutants for GCR1, GPA1, and PRN1, were irradiated with a single pulse of BL in the Low Fluence range with a total fluence of 102 µmol m$^{-2}$ or no light (DK). The resulting Lhcb RNA levels were determined by northern analysis. The data indicate that the single pulse of BL, unlike in wild type seedlings, has no effect on Lhcb RNA levels in lines with T-DNA insertions in GCR1, GPA1 and PRN1. The loss of activity occurs regardless of ecotype (col or ws) and is replicated, for most genes, in at least two independent insertion lines for each gene. Insertions distal to the promoter region for GPA1 (approx. 600-680 by upstream from the start of transcriptional initiation) do not result in the loss of BLF System activity. Induction of Lhcb expression was also monitored by qPCR, to confirm the fold-level of induction by BL. The resulting range of BL induction compares well to that observed using Northern analysis, as confirmed by Student's T-Test.

Expression of NF-Y Subunits is Limited in Etiolated Tissue:

NF-Y is a heterotrimeric protein comprised of A, B and C subunits. The Arabidopsis genome codes for 10, 10, and nine potential copies of the A, B, and C subunits, respectively, as determined by DNA and protein sequence analyses (Gusmaroli et al., (2001), Gene 264: 173-185; Gusmaroli et al., (2002), Gene 283: 41-48). The NF-Y family is poorly studied in higher plants, with most of the work focusing on specific members of the NF-Y-B subunit family, particularly NF-Y-B9 (LEC1; Lee et al., 2003) and the closely related NF-Y-B6 (LEC1-LIKE; Kwong et al., 2003) in Arabidopsis. There is some evidence for differential expression in plants of the NF-Y subunits (Gusmaroli et al., (2001), Gene 264: 173-185; Gusmaroli et al., (2002), Gene 283: 41-48).

In order to better define the NF-Y-A, -B and -C family members that have a potential for participation in the signaling mechanism of etiolated seedlings, we performed rtPCR, using RNA from etiolated wild type seedlings and primer pairs specific to each of the 29 NF-Y members. The results, indicate that the NF-Y-A5, NF-Y-B6, NF-Y-B9, and, NF-Y-C1, C4 and —C9 subunits are expressed in the six-day-old etiolated seedlings, suggesting that these NF-Y subunits have a potential role as signal carriers in the BLF system regulation of Lhcb transcription.

NF-Y-B9 (LEC1) and NF-Y-A5 are Required for BLF System Regulation of Lhcb Expression:

T-DNA insertion mutants are available in most members of the NF-Y-A family, the NF-Y-B family, and only a few members of the NF-Y-C family, including C1, and C4. There are no publicly available insertion mutants for the coding region of the C9 gene. In order to identify NF-Y members with a defined role in the BLF-system mediated Lhcb expression, we tested all available T-DNA insertion mutants of NF-Y-A, NF-Y-B and NF-Y-C. The data indicate that insertions in only one A family member, NF-Y-A5, and only one B family member, B9 exhibit a loss of BLF-System mediated Lhcb expression. Both NF-Y-A5 and NF-Y-B9 were identified by rtPCR as being expressed in the etiolated tissue. T-DNA insertions in all other NF-Y-B members, including NF-Y-B6 which is closely related to the NF-Y-B9 protein, do not result in the loss of the BLF System-mediated Lhcb expression. Similarly, insertions in all other NF-Y-A members and NF-Y-C1 and C4 do not exhibit the loss of BLF System-mediated Lhcb expression.

ABA can Elicit Lhcb Expression in the Cotyledons of Etiolated Seedlings and does so Through a GPA1-Mediated Pathway:

The BL signal transduction mechanism is minimally comprised of the GCR1, GPA1, PRN1, NF-Y-A5, NF-Y-B9 and potentially NF-Y-C9. ABA, like BL, can elicit the GCR1-GPA1 effector signaling pathways in etiolated cotyledons, as was demonstrated for the prephenate dehydratase 1 signaling pathway (Warpeha et al., (2006), Plant Physiol 140: 844-855). Thus, it was of interest to determine if ABA can activate Lhcb expression via the GCR1-GPA1-PRN1-NFY signaling chain in etiolated cotyledons.

Lhcb

RNA levels were measured in six-d-old etiolated wild type seedlings that had been treated with 800 nM ABA dissolved in ethanol (approximately 70% saturation for the germination response), or with ethanol alone. The ABA treatment in wild type seedlings, just like low fluence BL, induces Lhcb expression. We also tested the ability of ABA to induce Lhcb in T-DNA insertion mutants of the components of the BLF pathway: gcr1, gpa1, prn1, nf-y-b9, nf-y-a5. ABA fails to induce Lhcb RNA accumulation in the mutant seedlings, indicating that ABA and low fluence BL depend upon the same GPA1-based signaling pathway.

If low fluence BL and ABA utilize the same signal transduction chain, then the combination of a near-saturating BL treatment ($10^4$ µmol $m^{-2}$) and a near-saturating ABA treatment (800 nM) would not be expected to exceed saturation, where the two responses would not be completely additive. The data show the results of treatment with BL and/or ABA. The near-saturating doses of BL and ABA are not additive for Lhcb accumulation. The difference between the individual BL treatment response plus the ABA treatment response (Additive) is significantly different from the combined treatments single response, according to the Student's t-Test (95% confidence level, P=0.012). These data indicate that BL and ABA share all or part of a signal transduction chain, where each, BL and ABA, are capable of activating expression. The data are consistent with a shared signal transduction chain of GCR1-GPA1-PRN1-NF-Y.

GCR1, GPA1, PRN1, NF-Y-A5, NF-Y-B6, NF-Y-B9, and NF-Y-C4 are Required for the Signaling Mechanism that Acts to Inhibit the ABA-Mediated Delay in Seed Germination:

The data establish that ABA can act as a signal for and that PRN1 can act as a signal carrier in the BL-mediated GCR1, GPA1 signal transduction pathway leading to the expression of Lhcb in etiolated seedlings. We have demonstrated that PRN1 acts as the effector for GPA1 in the signaling mechanism that inhibits the ABA-mediated delay in seed germination. It appears that PRN1 participates in different signaling mechanisms in different tissues, and there is redundancy amongst signaling components in the germinating seed and young seedling. We tested the effect of ABA on germination rate in the same T-DNA insertion mutants as those described in the experiments for BL regulation of Lhcb expression in etiolated cotyledons.

The results, indicate that T-DNA insertion mutants of GCR1, NF-Y-A5, NF-Y-B9 and the closely related NF-Y-B6, show a marked increase in the delay in germination in response to ABA (i.e. appear to be hypersensitive to ABA). Insertions in other NF-Y-A or NF-Y-B family members, like NF-Y-A4 or NF-Y-B2, appear similar to wild-type, and therefore are not likely to have a role in this response. We also tested the insertion mutants in NF-Y-C1 and NF-Y-C4 since these components are expressed in etiolated seedlings. The nf-y-c4 mutant seed demonstrates a measurable increase in germination delay when compared to wild-type levels of germination, suggesting a role for NF-Y-C4 in the germination process.

Both NF-Y-B9 and NF-Y-B6 can Physically Interact with PRN1:

The data establish roles for GCR1, GPA1, PRN1, NF-Y-A5, NF-Y-B9, and potentially NF-Y-C9 in the BLF-System activation of Lhcb transcription; and, roles for GCR1, GPA1, PRN1, NF-Y-A5, NF-Y-B6, NF-Y-B9 and NF-Y-C4 in the signaling mechanism responsible for inhibiting the ABA-mediated delay in seed germination. GCR1 and GPA1 and GPA1 and PRN1 have specific interactions. Mammalian pirin is directly interact with mammalian NF-Y for transcription activation. Yeast two-hybrid and in vitro co-precipitation assays were used to determine if specific interactions could occur between PRN1 and NF-Y-B9 or between PRN1 and NF-Y-B6. NF-Y-B9 is active in both Lhcb and germination responses, NF-Y-B6, although a very similar protein to NF-Y-B9, is only active in the germination response. The results of the in vitro co-precipitation experiments indicate that PRN1 has the potential for a specific interaction with both NF-Y-B9 and NF-Y-B6.

The yeast two hybrid data, confirm by a second, independent assay, the potential for a positive physical interaction between PRN1 and NF-Y-B9. The yeast cells expressing NF-Y-B6 undergo 2-3 cell divisions.

Discussion:

The data presented herein demonstrate a) both BL and ABA can induce Lhcb expression in etiolated *Arabidopsis* seedlings; b) the physical interaction of PRN1, and NF-Y-B9; c) the expression of NF-Y-A5, NF-Y-B9, and NF-Y-C9 in etiolated tissue; d) the shared loss of BLF-System induction of Lhcb in T-DNA insertion mutant lines of GCR1, GPA1, PRN1, NF-Y-A5, and NF-Y-B9. Considered with previously published data that the CCAAT box as the BLF-System DNA regulatory element in the Lhcb gene along with the capability of GCR1-GPA1 interaction, allows us to define a potentially complete signal transduction mechanism for the BLF-System-mediated gene expression of Lhcb: GCR1, GPA1, PRN1, NF-Y, and the CCAAT box of Lhcb.

We also report that the same signal transduction mechanism, with the potential involvement of the additional or alternative NF-Y components NF-Y-B6 and NF-Y-C4, is involved in inhibiting the ABA-mediated delay in seed germination.

We recently demonstrated that GCR1 and GPA1, both critical to the BL and ABA mediated Lhcb expression in etiolated seedlings, are also critical to the mechanism through which BL BL and ABA act to increase PD1 activity, phenylalanine synthesis and phenylpropanoid pathway activity in etiolated seedlings (Warpeha et al., (2006), *Plant Physiol* 140: 844-855).

Single genes code for the Gα subunit (GPA1) and the putative G protein-coupled receptor in *Arabidopsis* (GCR1). Our finding that the same signal transduction mechanism would be used by two different signals such as BL and ABA, to achieve the same response in the same tissue is surprising and requires further exploration. Given the large number of systems and phenomena thought to rely on G-protein-mediated signaling it is likely that the sole *Arabidopsis* Gα subunit GPA1 interacts with many effector proteins. However, to date, only a few partners have been identified, including PRN1, Phospholipase C, Phospholipase Eα1, PD1 (Warpeha et al., 2006) and THF1 (Huang et al., (2006), *Plant Cell* 18: 1226-1238).

It is unclear how BL and ABA stimulate the GCR1, GPA1-based pathways in the cotyledons of etiolated seedlings. Given the very different nature of the two signals and therefore the chemical/structural nature of the receptors that would detect the two signals, it would be reasonable to assume the existence of two separate receptors.

Because ABA is derived from an asymmetric cleavage of the BL-absorbing carotenoids (i.e., zeaxanthin, antheraxanthin, violaxanthin) and because of the structural relationship of the heterocyclic head group on ABA and the carotenoid from which it derives, a single receptor could bind, depending on the specific situation, either ABA or a blue light-absorbing carotenoid. Blue light-absorbing carotenoids have been implicated as receptors in other phenomena in plants. The excitatory molecule responsible for the signaling mechanism that acts to interfere with the ABA-mediated delay in seed germination is not certain.

GCR1 belongs to the secretin (so-called 7-TM2) class of G-protein coupled receptors. The secretin class tends to bind ligands on the extracellular surface in part through an N-terminal extracellular extension. There has been some similarity shown to the GPCR transmembrane structure in *Dictyostelium* and *Drosophila*. The lack of structure, and the presence of several sites for potential secondary modification, and the extracellular nature of the ligand binding region, suggests that GCR1 could have many potential ligands in plants. While GCR1 has the characteristics of a classic heterotrimeric G-protein including sequence similarity with predicted seven transmembrane spanning domains, direct interaction with Gα and, localization to the plasma membrane fraction, and, while the phenotypes generated by the overexpression of GCR1 are consistent with its being a receptor, there are no direct data proving that GCR1 functions as a G-protein coupled receptor.

Our data both for Lhcb expression in the etiolated cotyledons and for the ABA effect on seed germination indicate a "standard" or an "in common" type of receptor for both the BL and ABA-G protein relationship in that the phenotypes of the gcr1 and the gpa1 mutants are the same, suggesting that GCR1 and GPA1 act in concert.

Pirin, initially identified as an NF-Y interacting protein in animals, was subsequently identified as also capable of binding to the ankyrin domain of Bcl-3, a nuclear localized member of the IκB proto-oncogene family. IκB normally functions to sequester dimerized members of the NF-κB/REL family of transcription factors in the cytoplasm (thereby preventing their action as transcription factors) and release of the various NF-κB/REL factors occurs in response specific signaling mechanisms including a variety of G-protein mediated pathways. Pirin has been identified as a quercetinase which means it plays a role in UV protection pathways. The GCR1, GPA1, PRN1, NF-Y-A5, B9, and C(?) signal transduction mechanism requires a means to traffic its signal into the nucleus. PRN1 is a likely candidate for that role.

Depending upon the quality and quantity of the materials stored in the endosperm, newly emergent seedlings may or may not have sufficient Phe stored to serve both the immediate need for protein, as well as for UV protection and/or other stresses or developmental processes that rely upon compounds produced by the phenylpropanoid pathway. This leaves a plant open to UV damage at a very immature age. UV damage causes thymidine dimers and permanent heritable damage. One of the enzymes that can be expressed by nucleic acids as described herein and provided to soybean plants and seedlings to address DNA damage is pirin (know as "PRN" in *Arabidopsis*); the actions of pirin proteins are involved with DNA repair as transcriptional regulators. Pirin's enzymatic function is as a quercetinase (see Merkens et al., Archives of Microbiology, 187(6):475-487, 2007; Clifton et al., Inorganic Biochemistry 100 (4):644-669, 2006; Adams, M. and Jia, Z C, Journal of Biological Chemistry 280(31):28675-28682, 2005) and the compound it acts on is quercetin in which it cleaves this compound, a phenylpropanoid pathway pigment ultimately derived from phenylalanine.

In one embodiment, a method of protecting plants from environmental stressors (e.g., UV radiation) as described herein involves transforming seeds or plants with a nucleic acid that suppresses Pirin activity, expression, or stability. In such a method, there is a reduction of the presence and/or action of quercetinase which results in the accumulation of more pigments for screening protection in the young developing seedling. PRN1 is abundantly expressed in seeds, and the effects of the mutations in PRN1 in etiolated and young seedlings have been shown. In an alternative method of protecting a plant from UV radiation, PD1 is overexpressed to produce more phenylalanine and PRN expression is reduced or eliminated in a seedling or young plant to optimize the production of screening pigments very early in development.

In animals, there is evidence that during cell and tissue differentiation there can be large changes and differences in expression of individual subunits of NF-Y. Little data exist on the specific roles for NF-Y in plants. There are data to indicate differential expression, splicing, and tissue distribution for NF-Y-A, B and C subunits (as determined by sequence information), suggesting NF-Y may play diverse roles in *Arabidopsis*. NF-Y-A subunits show much more sequence conservation than that of the B and C subunits, which show some evidence of asymmetric evolution in plants. Recently in sunflower and flax, NF-Y factors have been expressed and shown to be involved in embryogenesis and young cotyledons. In tomato, nuclear regulators of gene expression are able to bind to an NF-Y-C factor which may act as a recruitment factor effecting gene expression.

The rtPCR data presented herein suggest that only the NF-Y-A5, NF-Y-B9, NF-Y-C1, NF-Y-C4 and NF-Y-C9 subunits are expressed in six-day-old etiolated seedlings.

NF-Y-B9, identified herein as a member of the BLF-System and the signaling mechanism inhibiting the ABA-mediated delay in seed germination, was originally described as a desiccation embryonic lethal which, if helped past the desiccation issue, could produce a leafy cotyledon phenotype. NF-Y-B9, more commonly known as LEC1 is critical in the developing seed and that LEC1 regulates many aspects of late embryogenesis.

The closely related member, NF-Y-B6 (LEC1-LIKE) was identified by its ability to partially restore wild-type features to plants mutated in the coding region of NF-Y-B9. Our finding that NF-Y-B6 has a role in the signaling mechanism responsible for interfering with the ABA mediated delay in seed germination, but does not seem to participate in the BLF system induction of Lhcb expression in the etiolated cotyledons is consistent with the previous observations regarding the relationship between NF-Y-B9 and NF-Y-B6. Other embryonic-tissue-active proteins involved with LEC1 and LEC1-Like can be found in tissues other than seed, like FUS3, which may be involved in vegetative processes.

The variety of tissues and developmental stages where GCR1 and GPA1 interaction is important to physiology (guard cells, etiolated cotyledons, roots and embryonic tissue in the seed) may be reflective of the paucity of signal transduction genes in higher plants, and demonstrate that early signaling mechanisms can have shared components. *Arabidopsis* may "redeploy" this signaling mechanism, albeit with different effectors and modifiers at many stages of plant development, or in many tissues of the plant to accommodate the fact there is only one G-protein coupled receptor and one Gα subunit in the genome. In plants in general, these data may serve to underscore the importance of understanding the network of possibilities in G-protein signaling in plant development.

Example 6

G-Protein-Coupled Receptor 1, G-Protein Gα-Subunit 1, and Prephenate Dehydratase 1 are Required for Blue Light-Induced Production of Phenylalanine in Etiolated *Arabidopsis*

Materials and Methods
Plant Materials and Accessions:
Matched seed lots of wild-type Columbia (Col) *Arabidopsis* (*Arabidopsis thaliana*) and siblings carrying T-DNA insertions within coding regions of GCR1 (SALK_027808), GPA1 (SALK_066823), PRN1 (SALK_006939), and PD1 (SALK_013392, called pd1-1; SALK_029949, called pd1-2; both mutants have identical responses in our experiments, were obtained from the *Arabidopsis* Biological Resource Center (Alonzo et al., 2003, *Science* 301: 653-657). Plants intended for seed stocks were grown in Scott Metromix 200 (Scotts) in continuous white light as described elsewhere (Lapik and Kaufman, 2003, Id.). All lines are homozygous for the reported insertion. Gene sequence accessions were obtained from GenBank (www.ncbi.nlm.nih.gov) and SIGnAL (signal.salk.edu), and compared by CLUSTALX program.

Plant Growth and Preparation of Tissue:

Six-day-old dark-grown seedlings of *Arabidopsis* wild-type Col or insertion mutants were grown on 0.8% agarose plates containing only 0.53 Murashige and Skoog media as described in Lapik and Kaufman (2003), Id. The growth media contain no additional sugar, hormones, vitamins, or other nutrients. Seedlings were irradiated with a single pulse (100 s or less) of low fluence BL (total fluence of $10^4$ μmol $m^{-2}$ or $10^2$ μmol $m^{-2}$ [RNA only]; Warpeha and Kaufman, 1990) or no light (DK), and placed back in the dark for 2 or 24 h as indicated. Aerial portions were subsequently harvested to measure PD activity, amino acid analysis, and spectral analysis as described. RNA analysis has been described in full in Lapik and Kaufman (2003), Id. Seedlings were harvested 24 h after treatment and treated in a manner to that described for seedlings irradiated with BL.

Chemicals:

All chemicals unless otherwise noted were obtained from Sigma.

In Vitro GPA1-PD1 Activation Assays:

Full-length GPA1 and PD1 templates were amplified, prepared, and purified by the methods described (Lapik and Kaufman, 2003). GPA1 and PD1 proteins were individually produced by coupled in vitro transcription/translation using TNT T7 coupled wheat germ extract system (Promega). In vitro association assays were conducted by mixing approximately equimolar concentrations of GPA1 with PD1 in PD assay buffer at 4° C. with modifications for plants: 50 mM $K_2PO_4$ pH 7.5, 1.0 mM dithiothreitol, 100 mM phenylmethylsulfonyl fluoride, and 0.5% protease inhibitor cocktail for plants. Activated GPA1 was achieved by preincubation with 100 mM GTPγS (a nonhydrolyzable GTP analog). Inactivated GPA1 was achieved by preincubation with GDP, or GDPγS (a nonhydrolyzable GDP analog). At time zero, prephenate at concentration of 10.0 mM (final concentration 1.0 mM) dissolved in 50 mM $K_2PO_4$ pH 7.5 was added to the reaction mixture. Reaction mixtures were stopped at time zero and various time points thereafter by adding 0.5 volume of 1N NaOH. Absorbance values were read immediately afterward at 320 nm to assess conversion of prephenate to phenylpyruvate. For controls, activity assays with conditions such as buffer only, no protein, one protein (GPA1 or PD1), or GPA1 1 PD1 1 no prephenate, were conducted in the same manner as described above.

Amino Acid HPLC Preparation and Spectral Analysis Experiments:

Amino acid analysis was conducted as described (Razal et al., 1994 *Anal Biochem* 5: 98-104) with these modifications: Amino acid content was assessed in the aerial portions of wild-type Col and insertion mutant seedlings (pd1-1 and pd1-2) 2 h after BL irradiation treatment or mock treatment (no BL). Seedlings were grown and irradiated as described above, aerial portions harvested in liquid nitrogen, ground to a fine powder, and stored at −80° C. until amino acid analysis could be performed. All procedures hereafter were conducted at 4° C. or on ice unless specified. Preweighed ground samples were dissolved in methanol:water:triethylamine (2:2:1 by vol) at approximately 13 mL per 0.5 g of sample by shaking in the dark at 4° C. for 24 h. Two mL of the solution was centrifuged for 6 min at 12,000 rpm. The supernatant was transferred to a new 2.0 mL tube and dried using a using a speed vac (Savant). Quantity of 1.5 mL of acetone at −80° C. was added to the evaporated samples, and the mixture was ultrasonicated until the sample was fully dissolved. The acetone samples were kept at −80° C. for 30 min and centrifuged at 12,000 rpm for 5 min to remove precipitated proteins and other acetone-insoluble materials. The supernatant, containing the amino acids, was dried in a speed vac and used for amino acid or absorption spectra analysis.

Amino Acid Analysis:

The acetone-dried samples were resuspended in 50 mL methanol:water:triethylamine (2:2:1 by volume), redried in the speed vac, resuspended in 50 mL of ethanol:triethylamine:water:phenylisothiocyanate (Pierce; 7:1:1:1 by volume), incubated for 20 min, and dried in a speed vac. The dried phenylisothiocyanate-labeled samples were dissolved in 200 mL of disodium hydrogen phosphate (pH 7.4) buffer and passed over a pico tag column (Waters) per the manufacturer's specifications. Amino acid standard H (Pierce) was used as the standard to assign peak position.

Anthocyanins Extraction and Quantification:

Seedlings were grown in continuous DK for 7 or 5 d followed by 48 h of continuous BL irradiation at a fluence rate of $10^0$ μmol $m^{-2}$ $s^{-1}$. BL irradiation materials have been described in full (Warpeha and Kaufman, 1990a, *Plant Physiol* 92: 495-499). Anthocyanins were extracted and quantified according to Noh and Spalding (1998) *Plant Physiol* 116: 503-509. Replicates (three) and means were analyzed with the Student's t test.

Absorbance Spectra:

Absorbance spectra were obtained from samples in assay buffer as described above for the in vitro activation assays. Additional spectral analyses were carried out using samples prepared in the same manner as for amino acid analysis. Acetone dried samples were mixed with disodium hydrogen phosphate (pH 7.4) buffer and filtered once using a 0.45 μm syringe filter. Absorption spectra between 200 to 450 nm were obtained using a duel beam spectrophotometer (Spectronic Genesys 5; Thermo Electron).

Microscope Images:

Fluorescent images were obtained of living unfixed seedlings 24 h post BL or ABA treatment as described in the "Plant Growth and Preparation of Tissue" section. Optical sectioning was achieved by using a Zeiss Axiovert 200M microscope (Carl Zeiss), equipped with ApoTome (collected by grid projection), and a digital camera and the 4#,6-diamino-phenylindole, fluorescein isothiocyanate, and Texas Red filter sets (Chroma). Photographs of whole cotyledon fluorescence were snapped on the same microscope set up, minus the apoTome setting.

Results

PD1 has a Specific Interaction with GPA1:

A yeast (*Saccharomyces cerevisiae*) two-hybrid screen was used to identify transcripts derived from etiolated *Arabidopsis* seedlings that encode for proteins with the potential to interact with GPA1. The screen identified several different transcripts encoding potential partners including PD1, a putative cytosolic PD approximately 46 kD, encoded by At2g27820. The potential for physical interaction between GPA1 and PD1 was confirmed using an in vitro pull-down procedure. The *Arabidopsis* genome is reported as having five additional genes coding for PD (GenBank; www.ncbi.nlm.nih.gov; signal.salk.edu).

BL Stimulates the Production of Phe:

Because GPA1 has a role in BL signal transduction, and because of the role of PD in the production of Phe in bacteria and fungi (Haslam, 1993, Shikimic Acid Metabolism and Metabolites. John Wiley and Sons, New York), the levels of several amino acids were measured in mock-irradiated in darkness (DK) and BL-treated (BL, single pulse of $10^4$ µmol $m^{-2}$) 6-d-old dark-grown wild-type *Arabidopsis* seedlings.

The data indicate that a single pulse of low-fluence BL enhances the accumulation of Phe and Tyr in etiolated wild-type *Arabidopsis* by approximately 6- and 4-fold, respectively, 2 h after irradiation. In wild-type seedlings, the levels of Trp, whose synthetic pathway branches at chorismate, the immediate precursor to prephenate (the presumed substrate for PD1) and other amino acids (e.g. Ser, Gly, and Met) are generally unaffected by the BL treatment. The data indicate that BL enhances the synthesis of the aromatic amino acids and may be a key regulator downstream of the chorismate branch point.

BL-Induced Phe and Tyr Accumulation Occurs Via a PD1-Requiring Pathway:

To determine if PD1 is in fact responsible for the demonstrated BL-induced increase in Phe and Tyr accumulation, we tested T-DNA insertion mutants of PD1 for their ability to accumulate Phe, Tyr, and Trp in response to BL treatment. The data indicate that neither Phe nor Tyr accumulates in the pd1-1 or pd1-2 mutants 2 h after BL irradiation. The levels of Trp and other amino acids also remain unaffected by the BL. These data confirm that PD1 is responsible for BL induced accumulation of the aromatic amino acids in etiolated *Arabidopsis* and strongly supports the idea that phenylpyruvate, the immediate product of PD, can act as the immediate precursor to Phe.

Cytosolic PD Activity is Increased by BL:

The derived amino acid sequence for PD1 suggests that it codes for a cytosolic PD. To test for PD activity in a plastid-free cytosolic fraction and to determine if that activity is BL regulated, we adapted a standard cell extract assay based on Euverink et al. (1995), *Biochem J*, 308: 313-320 for use with *Arabidopsis*. Wild type and insertion mutants of PD1 *Arabidopsis* seedlings were grown for 6 d in complete DK, given a mock BL treatment (DK), or irradiated with a single brief pulse of BL (total fluence $10^4$ µmol $m^{-2}$) and returned to the dark for 2 h. Cytosolic extracts were tested for their ability to convert exogenously added prephenate (the precursor) to phenylpyruvate (the product) by measuring the change in $A_{320}$ over time.

The data confirm the presence of a PD activity in the cytosolic fraction and indicate that the activity is enhanced only in those extracts derived from the BL-treated wild-type seedlings. Extracts obtained from pd1-1 and pd1-2 mutant seedlings do not indicate BL-induced phenylpyruvate synthesis, suggesting that PD1 is the sole cytosolically located, BL-induced PD activity in etiolated seedlings.

Phenylpyruvate, the immediate product of PD1, is a committed precursor to Phe. Phenyl-alanine itself is a precursor to those compounds in phenylpropanoid pathway, many of which absorb in the UV/BL range (e.g. anthocyanins). The resultant absorption spectra obtained from the cytosolic extract assay of BL irradiated wild-type seedlings show a profound increase in, and difference in, compounds that absorb light in the UV/BL region. Changes in pigment composition and quantity of absorbing molecules can be seen in the cytosolic extracts themselves and in the absorption spectra of those extracts. Absorption spectra of extracts from the pd1-1 and pd1-2 mutants with and without BL irradiation are highly similar to extracts from dark-grown wild-type seedlings, suggesting that PD1 is responsible for the Phe that in turn leads to the production of those BL-induced compounds responsible for the spectral changes in etiolated wild-type seedlings.

GCR1, GPA1, and PD1 Form a Signaling Chain that Effects BL-Induced Phe Accumulation:

The data demonstrate that GPA1 can interact with PD1 and that PD1 is responsible for the BL induction accumulation of phenylpyruvate, Phe, and a range of UV- and BL-absorbing compounds. GCR1 can interact with GPA1, and we demonstrated that both GCR1 and GPA1 participate in the BL induction of Lhcb RNA accumulation. Together, these data suggest that GCR1, GPA1, and PD1 form all or part of a signal transduction mechanism responsible for BL-induced Phe accumulation in etiolated *Arabidopsis*.

To test this hypothesis, we measured the ability of etiolated T-DNA single-insertion mutants in GCR1 and GPA1 genes to accumulate the amino acids Phe, Tyr, and Trp, as well as UV- and BL-absorbing compounds in response to irradiation with BL. The data indicate that neither mutant accumulates Phe or Tyr, confirming a role for GCR1 and GPA1 in this BL response. The difference in spectra indicate that the cytoplasmic constituents of BL-irradiated gcr1 and gpa1 mutants differ considerably from wild type, each other, and the pd1 mutants. The general trend appears to be one in which the pd1 mutant has lost the widest range of UV absorbing material (actually resembling unirradiated wild-type seedlings), the gcr1 mutant has lost the least, and the gpa1 mutant is somewhat intermediate.

Activated GPA1 can Increase PD1 Activity:

The data confirm that GPA1 and PD1 can interact, but do not address the biochemical consequences of that interaction. The fact that a single pulse of BL can activate both Gα and PD1, and that BL activation of PD1 activity is lost in the gpa1 mutant suggests that the interaction between activated (GTP-bound) GPA1 and PD1 is responsible for the BL-induced increase in PD1 activity.

PD1 and GPA1 were synthesized and purified as previously described (Lapik and Kaufman, 2003, *Plant Cell*, 15: 1578-1590). GPA1 is generally thought to be synthesized in an inactive state (i.e. resembling the structure when GDP is bound, even though no GDP is present). This structure can be changed to an active one by incubating GPA1 with the non-hydrolyzable GTP analog GTPγS (Lapik and Kaufman, 2003, Id).

GPA1 was preincubated with GTPγS (producing activated GPA1), GDP, or GDPβS (a nonhydrolyzable analog of GDP-producing inactive GPA1), prior to incubation with PD1 and prephenate, and subsequent monitoring of PD1 activity. The data indicate that incubation of PD1 with activated GPA1 results in a 2-fold increase in PD1 activity when compared with inactive (incubation with GDP or GDPβS) or no GPA1. The increase in activity occurs quickly as approximately 90% of the measured increase in activity occurs within the first 10 min of incubation. These data are confirmed by HPLC analysis of the prephenate-to-phenylpyruvate conversion rate.

pd1, gcr1, and gpa1 Mutants Do Not Synthesize Specifically Located UV- and BL-Absorbing Compounds in Response to Treatment with BL: The absorption spectra and visual data indicate that BL treatment of wild-type *Arabidopsis* results in a significant increase in the amount and range of UV- and BL-absorbing compounds, and that PD1 activity is required for the synthesis of these compounds. We used deconvolution microscopy and optical sectioning to help define the location(s) of the absorbing compounds synthesized in wild-type seedlings in response to BL treatment, and as a consequence of PD1 activity. The results indicate the presence of a set of cells in the upper layers of the cotyledon tip containing UV- and BL-absorbing fluorescent material, which increases in accumulation in response to the BL treatment. This fluorescent material is absent from unirradiated (DK) and irradiated (BL) pd1 mutants.

Because ABA is able to elicit Lhcb transcription in etiolated cotyledons using a signal transduction pathway identical to that of BL and requiring both GCR1 and GPA1 we tested application of ABA to etiolated cotyledons to determine the effect on accumulation of UV- and BL-absorbing fluorescent material. ABA treatment results in a phenotype identical to that observed in wild-type seedlings for BL irradiation, and, like BL, the response to ABA is dependent upon PD1.

The data indicate the natural fluorescence of whole cotyledons and confirms that gcr1 and gpa1 mutants also lack the BL-induced UV-absorbing fluorescent material at the tip of the cotyledon observed for pd1-1 and pd1-2 mutants. The prn1 mutant appears to have the same fluorescence pattern as wild-type seedlings.

Dark-Grown Pd1 Mutants do not Accumulate Anthocyanins:

The data indicate that similar UV- and BL-absorbing compounds are synthesized in etiolated wild-type (nonirradiated) and pd1-1 and pd1-2 mutant seedlings, although a greater quantity is synthesized in wild-type seedlings. The data also suggest that an additional set of UV- and BL-absorbing compounds are synthesized in wild-type seedlings via a BL-activated PD1-dependent pathway. BL will stimulate anthocyanin (a UV/BL-absorbing product of the PD1-dependent phenylpropanoid pathway) synthesis in *Arabidopsis*. The data in Table 4 show that etiolated pd1-1, pd1-2, and wild-type seedlings accumulate anthocyanin and that the level of accumulation in wild type is approximately 30% greater then in the pd1 mutant seedlings, and this difference is significantly different according to the Student's t test. This is consistent with the overall difference in UV- and BL-absorbing compounds. Table 5 also shows that measurable anthocyanins in wild-type seedlings exposed to continuous BL for 48 h does not differ appreciably from that measured for pd1-1 or pd1-2 seedlings similarly treated.

Table 5 shows anthocyanins production in dark-grown seedlings. Seedlings were grown for 7 d in complete DK or for 5 d in complete DK followed by 48 h of continuous BL at $10^0$ μmol m$^{-2}$ s$^{-1}$. Anthocyanins extraction and quantification were performed on fresh tissue. Data derive from three independent replicates. Errors represent the SEM. Replicates (three) and means were analyzed with the Student's t test

TABLE 5

| Anthocyanins accumulation (absorbance/g fresh weight) | | | |
|---|---|---|---|
| | Col Wild Type | pd1-1 | pd1-2 |
| DK | 0.03$^a$ +/− 0.004 | 0.02$^a$ +/− 0.002 | 0.02$^a$ +/− 0.002 |
| Continuous BL | 1.54 +/− 0.056 | 1.31 +/− 0.013 | 1.25 +/− 0.056 |

$^a$The means of the mutant anthocyanins levels are significantly different from wild-type levels (>95% confidence level).

The BL-Induced Accumulation of Phe is not Part of the Post-GPA1-Signaling Mechanism that Leads to the BL Regulation of Lhcb:

The iterative interaction between GCR1, GPA1, and PD1, the common phenotype of the T-DNA insertion mutants, and the ability of activated GPA1 to activate PD1 defines PD1 as a GPA1 effector and GCR1, GPA1, and PD1 as a signal transduction chain for the BLF system activation of PD1 activity.

A single pulse of low-fluence BL also induces the immediate expression of Lhcb in etiolated pea (*Pisum sativum*) and *Arabidopsis* (Marrs and Kaufman, 1991, Planta 183: 327-333; Gao and Kaufman, 1994, Plant Physiol 104: 1251-1257). The signal transduction mechanism responsible for this gene expression is comprised in part by a GCR1, GPA1, PRN1, and NF-Y-signaling chain, wherein PRN1 acts as the GPA1 effector. To confirm the divergence of these two signaling mechanisms at the level of the effectors, we tested a T-DNA insertion mutant in the PRN1 gene for ability to accumulate the amino acids Phe, Tyr, and Trp in response to BL treatment, and ability to produce fluorescent material at the tip of the cotyledon in response to BL treatment. In both instances, the prn1 mutant appears to respond like wild type: The prn1 mutant accumulates both Phe and Tyr, and the tip of the cotyledon has natural fluorescence similar to that observed for wild-type seedlings.

We also tested the ability of pd1 insertion mutants to accumulate Lhcb RNA in response to BL treatment. The data indicate that BL-induced accumulation of Lhcb RNA for pd1 mutants is similar to the level of accumulation observed for wild-type seedlings.

Discussion:

Phe-derived compounds can account for as much as 30% to 40% of the mass of a plant. The two main synthetic pathways by which prokaryotes and fungi produce Phe rely on the committed synthesis of prephenate from chorismate-via-chorismate mutase. The major synthetic pathway proceeds via the conversion of prephenate to phenylpyruvate by PD and the subsequent conversion phenylpyruvate to Phe by phenylpyruvate amino transferase. Chorismate mutase and PD activities can occur as two separate proteins or, in the case of P protein in *Escherichia coli*, as a fused protein with both activities. An alternative pathway proceeds via the conversion of chorismate to arogenate via the action of a prephenate amino transferase and the subsequent conversion of arogenate to Phe via the action of arogenate dehydratase. Cyclohexadienyl dehydratase is reported to have both PD and arogenate dehydratase activities.

It has been the assumption that in plants, unlike fungi wherein synthesis takes place in the cytosol, that the postchorismate steps occur in the chloroplast via an arogenate intermediate (for review, see Schmid and Amrhein, 1995, *Phytochemistry* 39: 737-749). Examination of the *Arabidopsis* genome reveals no copies of arogenate dehydratase or cyclohexadienyl dehydratase. Prior studies, (Razal et al. (1994) *Anal Biochem* 5: 98-104) were unable to isolate or detect arogenate from any plant grown under any light condition.

In contrast, the *Arabidopsis* genome contains three genes coding for chorismate mutase, two chloroplastic and one cytosolic. Six PD genes are described for *Arabidopsis*, where sequence analysis predicts four have signal peptides, suggesting they are chloroplastic, and two less likely to have signal peptides (including PD1), which we believe they are cytosolic. Given the importance of Phe to plants and the large investment of genetic material in phenylpyruvate based pathways in both the chloroplast and cytoplasm, it would seem likely that the process of Phe production can occur via phenylpyruvate both in the cytosol and in the mature plant, the chloroplast. Our findings herein confirm that in etiolated seedlings, this pathway can occur in the cytoplasm and can occur via a phenylpyruvate intermediate.

Data presented herein deriving from the use of T-DNA insertion mutants and biochemical and protein interaction studies, considered along with interaction data confirm that GCR1, GPA1, and PD1 form all or part of a BL-induced signal transduction mechanism resulting in an immediate increase in the rate of phenylpyruvate synthesis and the subsequent increase in the levels of Phe. It remains unclear if GCR1 acts as, or downstream of, the responsible BL receptor. The fact that pd1 insertion mutants lack the BL-induced responses indicates that none of the other five genes coding for PD has the capacity to compensate the PD1 activity in etiolated seedlings. All of our plant material is derived from dark-grown seedlings, where BL irradiations are less than 2 min, so we are examining early fast responses to discrete pulses.

We have recently demonstrated that PRN1, like PD1, can act as a GPA1 effector. In this signaling chain, the BL-induced PRN1-mediated pathway leads to the induction of Lhcb transcription. GCR1 is also involved in this BL-mediated pathway and, similarly, with an undefined role. The data presented herein support our hypothesis that the two BL-signaling pathways branch immediately downstream of GPA1, via its separate interaction with PD1 or PRN1.

Because GPA1 is the only Gα-subunit in *Arabidopsis*, and because it is known to be involved in several different signal transduction pathways, may not interact with many different effector proteins. Proteins known to both interact with and participate in the same signaling pathways as GPA1 include PRN1, Phospholipase C, and Phospholipase Eα1. Based on our data and what is known about PDs we have designed a model of Phe formation in etiolated seedlings.

Etiolated *Arabidopsis* seedlings have relatively small pools of prephenate or Phe. Phe is the first committed precursor for the phenylpropanoid pathway, itself responsible for the synthesis of a large number of UV- and BL-absorbing compounds. It would seem likely that many of the BL- and UV-absorbing compounds that occur as a result of the BL activation of the GCR1, GPA1, and PD1 pathway intimately derive from the phenylpropanoid pathway. Irradiation resulted in a greater than 100-fold induction in phenylpropanoid synthesis. Phe is the precursor for Phe-derived compounds including the light-induced UV and visible protective pigments. The seedling mutants for PD1 fail to accumulate the phenylpropanoid precursor Phe and display either little or no fluorescence (mock-irradiated, i.e. no light), or diffuse reddish fluorescence (BL-irradiated) upon excitation by UV and blue wavelengths.

The compounds causing the fluorescence observed in wild-type seedlings, which are absent from the PD1-deficient seedlings, are unknown. Likely candidates include the anthocyanins and sinapolymalate. Sinapolymalate, a UV-fluorescent compound, accumulates in the upper leaf epidermis and can cause a blue-green fluorescence under UV light. Anthocyanins are present in etiolated pd1-1 and pd1-2 albeit at levels about 30% less than measured in etiolated wild-type seedlings.

Growth of pd1-1 and pd1-2 for 48 h in continuous BL results in anthocyanins levels approximating those measured for wild-type seedlings.

Example 7

Transforming Plants

Phe in Soybean Seeds.

When Soybean seeds of commonly used varieties for commercial growth were assessed for aromatic amino acid content, we found per weight very little Phe in the seed. If transformation can occur whereby Phe synthesis could occur during seed maturation, there would be a suitable method to increase Phe in the seed. Hence the Phe is available during germination, the young plant's most sensitive time to UV radiation. We have cloned PD1 into the Gateway vector system (Invitrogen, Carlsbad, Calif., USA). This is a versatile vector which will allow for many expression studies and easy manipulation and transformation by many methods is possible.

Method (b) Overexpression of PAH.

Cis-regulatory sequences and transcription factors controlling seed protein gene expression in soybean and the legume family, in general, are highly conserved across plant species. Seed storage proteins like phaseolin have a high level of expression, are seed-specific promoters, and are formed in seed development; this protein and similar proteins have been used with success (Karchi et al. 1994; Falco et al., 1995). A gene construct with seed specific expression is unlikely to perturb other metabolic processes in the plant.

Methods

Transformations.

Constructs of PD1 that are Gateway™ (Invitrogen, Carlsbad, Calif.)-compatible have been made. A Gateway-compatible destination vector capable of overexpressing PD1 transcript with hygromycin resistance for plant selection, and expression of spectinomycin for *agrobacterium* or *E. coli* transformation with a visible marker (GFP) for selection of transformants was made. Constructs of other PDs (e.g., PD2, PD3, PD5) can be made easily (e.g., constructs that express phe at other times of development) in the same fashion as described by Folta and Dhingra (2006). Several phaseolin promoters are tested for strength of expression as determined by Phe accumulation (HPLC) in the developing seed as measured by seed HPLC analysis, where controls are compared to seeds expressing constructs. The HPLC analysis is sensitive to picogram quantities of Phe, Tyr and Trp amino acids (Warpeha et al., Plant Physiol. 143:1590-1600, 2006).

For the construction of vectors, see Warpeha, K. M., Gibbons, J., Carol, A., Tree, R., Durham, W., Slusser, J., and Kaufman, L. S. Critical exploration of UV-signaling versus UV damage by using mutants of the prephenate dehydratase1 gene in etiolated *Arabidopsis*. Submitted, 2008; Warpeha, K. M., Sullivan, J., Gibbons, J., Carol, A., Tree, R., Durham, W., Slusser, J., and Kaufman, L. S. (2007) Phenylalanine is the rate limiting step for protection from atmospheric UV Radiation Damage in Soybean (*Glycine max* L.). Submitted, 2008.

Example 8

Phenylalanine Physically Shields Molecules in Solution from UV Damage

The data in FIG. 16 show that phenylalanine treatment added to a solution containing one or more chemicals such as herbicides and fungicides can be applied to crops or other targeted plants and can physically prevent the breakdown of these chemicals in the solution—breakdown as a result of natural sunlight. Phenylalanine can physically shield other compounds in solutions and thus can be used to shield herbicides, fungicides, as well as any other compounds that farmers would want to use in fields to apply to plants or soil.

Example 9

The Role of GCR1-GPA1-PD1 in Stress

The role of heterotrimeric G proteins in seedling responses to the environment is emerging as a fascinating area of basic research. Where animals have many GPCR's and Gα, β and γ subunits, evolution has been economical in *Arabidopsis*, with one Gα, (GPA1; Ma et al., Proc Natl Acad Sci USA 86:3821-3825, 1990), one Gβ (AGB1; (Weiss et al., Proc Natl Acad Sci USA 91:9554-9558, 1994), two Gγ (AGG1 & AGG2; (Mason et al., Proc Natl Acad Sci USA 97:14784-14788, 2000; Mason et al., Biochem. Biophys. Acta 1520: 147-153, 2001) subunits, and one potential G-protein coupled receptor identified, GCR1 (Josefsson and Rask, Eur J Biochem 249:415-420, 1997; Perfus-Barbeoch et al., Curr Opin Plant Biol 7:719-731, 2004). The sole Gα-subunit in *Arabidopsis* is involved in a number of processes in multiple tissues, at different stages of the life cycle. GPA1 interacts with an ever-growing list of effectors including Pirin1 (PRN1), Phospholipase Dα1, THYLAKOID FORMATION1 protein (THF1), and Prephenate dehydratase1 (PD1/ADT3 (Warpeha et al., Plant Physiol. 140:844-855, 2006) which catalyzes the penultimate step of L-phenylalanine (Phe) formation.

Etiolated seedlings treated with blue light (BL) UV-A, UV-B and ABA exhibit increases in Phe levels as a result of the activation of the GCR1-GPA1-PD1 signaling pathway (Warpeha et al., Plant Physiol. 140:844-855, 2006; Warpeha et al., Plant Physiol. 143:1590-1600, 2007). Data presented herein also demonstrate that UV-B, salt and heat as well as the phytohormones ABA and Jasmonic acid use the GCR1-GPA1-PD1 pathway.

Figure 23:
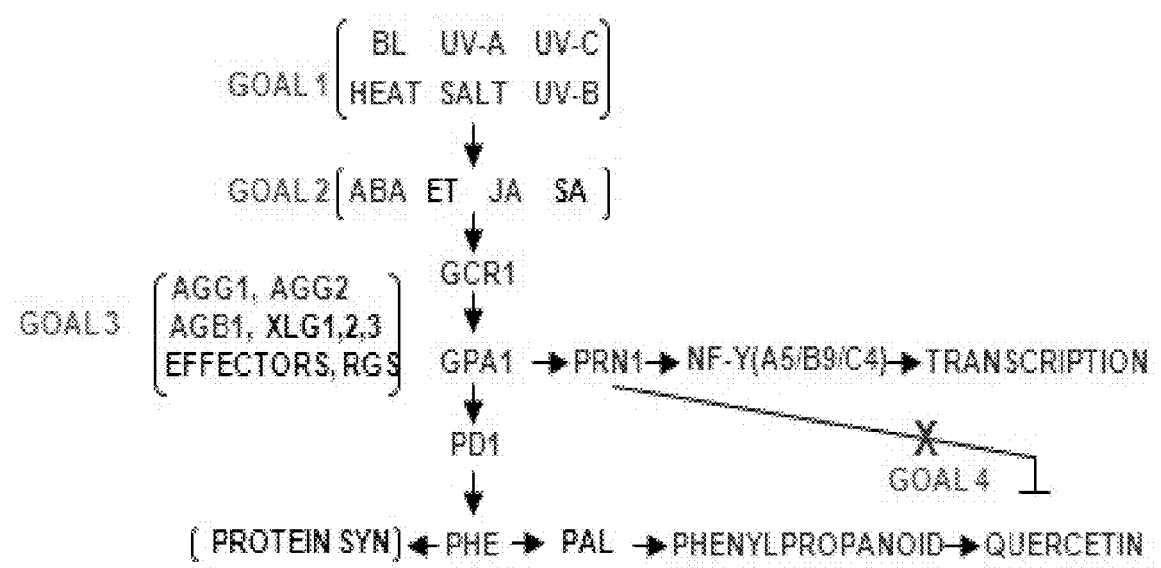
FIG. 23 is a schematic depicting a model for the stress induced signaling pathway in young etiolated seedlings. BL=blue light; UV-A=320-380 nm; UV-B=290-320 nm; UV-C=150-290 nm; ABA—abscisic acid; ET=ethylene; JA=jasmonic acid; SA=salicylic acid; phe=phenylalanine; PAL=phenyl ammonia lyase.

It is hypothesized herein that the GCR1-GPA1-PD1 signaling "cassette" is a signal response chain that orients the new seedling to its environment post-germination. The GCR1-GPA1-PD1 pathway mediates the appearance of stress symptoms, as well as the acclimation process and the induction of stress tolerance in the young seedling. The role of GCR1-GPA1-PD1 in stress, the role of hormonal second messengers, and the role of other G-protein components is explored. It has been shown that GPA1 interacts with a protein known as Pirin1 (Lapik et al., Plant Cell 15:1578-1590, 2003). Data described herein indicates that PRN1 may be involved in the regulation of quercetin levels. The role of PRN1 in the GCR1-GPA1-mediated signaling pathway forms is explored. A model describing the potential relationships of the signaling components under study is shown in FIG. 23.

In *Arabidopsis*, six genes code for prephenate dehydratase/arogenate dehydratase, so named as it can work with either prephenate or arogenate although the later appears to the substrate of choice. Only PD1/ADT3 is expressed in etiolated seedlings (Warpeha et al., Plant Physiol. 140:844-855, 2006). The product encoded by At2g27808 is referred to herein as PD1. The aromatic amino acid Phe is required for protein synthesis, and is the precursor to the large number of secondary metabolites called phenylpropanoids (Hahlbrock and Scheel, Annual Review of Plant Physiology and Plant Molecular Biology 40:347-369, 1989; Kliebenstein, D. J., Plant Cell Environment 27:675-684, 2004; Winkel, B. S. J., Annual Rev Plant Biol 55:85-107, 2004), many of which can serve as protectants to various environmental stresses. Phe which can account for up to 30-40% of the total organic carbon in a plant is the first committed precursor of the phenylpropanoid pathway, and thought to be a concentration limiting substrate. PD1 is critical in etiolated seedlings for synthesis of the amino acid Phe.

Addition of exogenous Phe to the growth media restores waxes, fatty acids, UV-absorbing materials and restores resistance to UV damage in pd1 mutants. Quercetin, found in large reserves in the seed is likely to be important in the young seedlings.

Abiotic stressors such as heat/cold (Wahid et al., Env. Exp. Bot. 61:199-223, 2007; Guy et al., Phys. Plant 132:220-235, 2008; Levya et al., Plant Physiol. 108:39-46, 1995; Christie et al., Planta 194:541-549, 1994; Wade et al., Plant Physiology 131:707-715, 2003; Kreps et al., Plant Physiol. 130:2129-2141, 2002; Zhue, J. K. Annu. Rev. Plant Biol. 53:247-273, 2002; Mittler et al., Trends Plant Sci. 11:15-19, 2006; Misra et al., Plant J. 51:656-669, 2007) and UV-B, can elicit Phe-derived phenylpropanoids. Less studied for phenylpropanoid induction is salt stress, but recent metabolome profiling, and studies using *Arabidopsis* cell culture indicate that phenylpropanoids might be key responders to all abiotic stress.

It has been reported that if there is adequate induction of the phenylpropanoid pathway within the first three weeks post-germination, it may influence the plant's ability to respond to later stresses. *Arabidopsis* seeds do have stored flavonols (quercetins) and other similar compounds. It has been shown that young (6-7 d) etiolated wt seedlings are capable of responding to UV via the GCR1-GPA1-PD1. Thus, each of these components must exist in the etiolated seedling by 6 d. When etiolated pd1 mutants are complemented with Phe, they are able to respond to UV like wild type. This indicates that enzymes like PAL and CHS are already present and active at sufficient levels. Both abiotic and biotic stimuli can elicit PD1 activity via GPA1 within minutes. The fact that Phe is the ultimate precursor of thousands of compounds involved in stress responses suggests that the GCR1-GPA1-PD1 could be a mediator of a number of stressors in young seedlings. Three common abiotic stressors which may utilize the GCR1-GPA1-PD1 pathway to affect Phe synthesis are examined herein. These stressors are UV-, B, salt and heat.

Abiotic stressors can also induce production of phytohormones that are small signaling molecules, which may be involved in the up-regulation of Phe and subsequent phenylpropanoids including ABA, jasmonic acid (JA) salicylic acid (SA) and ethylene (ET). Because it is desirable to understand GCR1-GPA1-PD1 signaling and specifically in how it may mediate abiotic stress signals, how these phytohormones may utilize this same signaling pathway perhaps to prepare the young seedling for future stressors is examined. The GCR1-GPA1-PD1 pathway is critical to prevention of damage by UV-B radiation.

The initial signaling components of most abiotic stressors and the mechanisms that control tolerance to specific stressors remain unknown. Although many stressors ultimately effect changes in the expression of the same gene families, there is also evidence that different stressors may share early signal transduction components, often referred to as "crosstalk". In addition to previously published data, the data described herein indicate that ABA and the GCR1-GPA1-PD1 signaling pathway mediates the initial response to a number of different abiotic stress signals in young etiolated *Arabidopsis* seedlings and is one source of cross talk.

*Arabidopsis*, a genetic model organism, has one Gα subunit (GPA1), one Gβ subunit (AGB1), and two Gγ subunits (AGG1, AGG2) making the young etiolated *Arabidopsis* is an ideal system in which to study G protein signaling (Lapik and Kaufman, Plant Cell 15:1578-1590, 2003; Warpeha et al., Plant Physiol. 140:844-855). Although developmentally simple, young etiolated seedlings respond to stress by immediately synthesizing Phe as a result of the activation of the GCR1-GPA1-PD1 pathway.

FIG. 23 depicts the following, testable model. Individual abiotic stressors (eg. salt, heat, UV-B) act through one or several phytohormone second messenger (eg. ABA, ET, JA, SA). These second messengers, alone or in combination lead to the activation of CGR1. GCR1 activates GPA1 which in turn activates PD1 leading to an enhanced rate of Phe synthesis. A portion of the Phe is used as substrate for the phenylpropanoid pathway and the synthesis of protective compounds, including quercetin, enabling the etiolated seedlings to tolerate stress. In young etiolated seedlings that have not been exposed to stressors, small amounts of Phe are made via the basal activity level of PD1. This Phe can be used by the phenylpropanoid pathway to synthesize small amounts of stress-protective compounds, including quercetin. In the absence of stress, PRN1, acting as a quercetinase, degrades quercetin and returns the catabolites to the metabolic pool. Stressor activated GPA1 (in addition to activating PD1) interacts with PRN1 and thereby turns off the quercetinase activity. PRN1 then assumes its role as a ccaat-box interactive protein and as a transcriptional activator.

There are several measurable end points of the GCR1-GPA1-PD1 signaling cascade that can be used as assays to test this model; direct measures include determining the level of Phe and the level of PD1 activity; indirect measures include determining the levels and location of UV-B absorbing, fluorescent compounds (including quercetin) and the ability to survive stress.

The experiments described herein provide the opportunity to characterize a complete G-protein mediated signaling pathway in young etiolated seedlings. Understanding this specific pathway is especially important as young seedlings are vulnerable to stress damage that can lead to lower productivity (i.e. seed mass) in adult plants. Thus, not only will the information learned be useful to a basic understanding of G-protein mediated signaling in plants, but will also be useful in developing models whereby stress acts on young seedlings and perhaps ways of mediating that stress.

Using the experiments described herein, the following questions are answered. What is the role of the GCR1-GPA1-PD1 signal transduction pathway in the response of young etiolated seedlings to various abiotic stressors? Can the well-characterized stress signaling molecules ABA, JA, SA or ethylene excite this GCR1-GPA1-PD1 cassette and if so how does this relate to stress based activation of the GCR1-GPA1-PD1 pathway? Do AGB1, AGG1 and AGG2 and other characterized G-protein associated proteins have a role in the GCR1, GPA1, PD1 mediated response of young etiolated seedling to exposure to UV-B, salt and/or heat stress? Can PRN1 act as a quercetinase and does the GCR1-GPA1-PRN1 signaling pathway have a regulatory role in effecting the products of the GCR1-GPA1-PD1 signaling pathway?

Unless otherwise stated, all experiments are performed using six day old etiolated *Arabidopsis* seedlings. Seeds are imbibed in the dark, and "planted" on 0.8% agar supplemented with 0.5× MS on phytotrays. Trays are then placed at 4° C. for 48 h and subsequently moved to dark growth chambers at 20° C. for 6 d, treated under green safelight conditions and returned to darkness for the time indicated by the specific experiment. A full listing of insertion mutants to be tested are found in Table 6. Unless indicated all mutant and wild type are the Columbia ecotype.

Example 10

The Role of the GCR1-GPA1-PD1 Signal Transduction Pathway in the Response of Young Etiolated Seedlings to Various Abiotic Stressors Young etiolated seedlings have little or no protection against abiotic stressors. The young seedling is also a stage in which exposure to low levels of certain stressors confers a tolerance to those and other stresses. Several lines of current research indicate that different stressors may share signal transduction components, referred to as "cross-talk". It is therefore germane that we understand the signal transduction systems activated by abiotic stresses and how these signal transduction systems operate to produce compounds that in turn protect the plants against future stress.

It has been demonstrated that treatment of young etiolated seedlings with BL or UV-A, both known to enhance stress responses in young etiolated seedlings, activate the GCR1-GPA1-PD1 signal transduction chain and result in the increased accumulation of Phe. The same is true of ABA, a stress-related plant hormone, and of UV-C, an abiotic, but not environmental stress. There is a need to understand if common abiotic stresses, such as UV-B, salt and heat, also act through the GCR1-GPA1-PD1 signaling pathway, result in PD1 activation and the subsequent synthesis of Phe. There is also a need to define the basic characteristics of the stress induction of CGR1-GPA1-PD1 cassette so that productive experiments can be designed to address the potential for cross talk in this system.

Multiple, well-characterized T-DNA insertion, knock-out, mutants (see Table 6) are used to characterize the roles of GCR1, GPA1 and PD1 in the responses of young etiolated *Arabidopsis* seedlings to the environmental abiotic stressors UV-B, salt, and heat. The excitation of the GCR1-GPA1-PD1 signaling pathway is measured by using four published, well characterized assays (Warpeha et al., Plant Physiol. 140; 844-855, 2006; Warpeha et al., Plant Physiol. 143:1590-1600, 2007). The four assays consist of two direct measurement of pathways activity, determination of PD1 enzymatic activity levels and Phe levels in whole cell extracts of the aerial portions of appropriately treated wt and mutant seedlings, and two indirect methods, observation of the accumulation of fluorescent compounds in the tip and adaxial surface of the cotyledons of appropriately treated wt and mutant seedlings, and the ability of appropriately treated wt and mutant seedlings to survive subsequent exposure to normally sub-lethal levels of UV-C (254 nm).

Those stressors that both effect all four assays and whose activity is dependent on all three signaling component (GCR1, GPA1 and PD1) are characterized. Published data and data described herein suggest that all three stressors, UV-B, salt and heat meet these criteria. Fluence—dose response, time course, and in the case of UV-B, reciprocity, measurements are performed. Time course measurements are conducted using ¾ saturation levels of the appropriate stress. The range of exposure times, if any, during which the Bunsen-Rocoe Law of Reciprocity holds for UV-B induced stress responses is determined.

TABLE 6

T-DNA Insertion Lines for G-proteins and G-protein Related Components Used

| Gene | Acccessions for insertion | lines |
| --- | --- | --- |
| GCR1 (At1g48270) | SALK_027808 (gcr1) | SAIL_1142_D06 |
| GPA1 (At2g26300) | SALK_066823 (gpa1-3) | SALK_001846 (gpa1-4) |
| AGB1 (At4g34460) | SALK_061896 (agb1-2) | SALK_020330 |
| AGG1 (At3g63420) | SAIL_381_HO2 | GABI-Kat 736A08 (agg1-2) |
| AGG2 (At3g22942) | SALK_039423 | SALK_010956 (agg2-1) |
| PD1/ADT3 (At2g27820) | SALK_029949 (pd1-2) | SALK_013392 (pd1-1) |
| RGS1 (At3g26090) | SALK_074376 (rgs1-2) | SALK_107240 |
| XLG1 (At2g23460) | SALK_119657 | SAIL_393_G05 |

TABLE 6-continued

T-DNA Insertion Lines
for G-proteins and G-protein Related Components Used

| Gene | Accessions for insertion | lines |
| --- | --- | --- |
| XLG2 (At4g34390) | SALK_062645 | SALK_007758 |
| XLG3 (At1g31930) | SALK_107656 | SALK_030162 |
| THF1 (At2g20890) | SALK_094925 | SALK_094926 |
| PLD (At3g15730) | SALK_067533 | SALK_087355 |

Referring to Table 6, the basic parameters describing the response to each of the three stressors are established, that information is used to determine if UV-B, salt and/or heat act through the same exact GCR1-GPA1-PD1 molecules in the same cells and subsequently if one stress can confer protection against subsequent exposure to either the same stress or perhaps to a different stress.

Six day old, etiolated wt and multiple well characterized T-DNA insertion mutant for GPA1, GPA1 and PD1 (Table 6) seedlings are assayed for the effect of UV-B, heat, and salt treatment on the levels of Phe and PD1 enzymatic activity in whole cell extracts of the aerial portions of the seedlings, for accumulation of fluorescent compounds in the tip and adaxial surface of the cotyledons and for the ability appropriately to survive subsequent exposure to sub-lethal levels of UV-C (254 nm). Initial assays are conducted 24 h after exposure to the stressor.

The initial tests are conducted using a single dose or fluence based on those used in recently published *Arabidopsis* studies. Broad band UV-B (300-317 nm) and narrow band pass (10 nm) 317 nm light is tested at a total fluence of $10^4$ $\mu molm^{-2}$ (Warpeha et al., Plant Cell and Environ. Vol. 31:1756-1770, 2008; Warpeha et al., Plant Physiol. Vol. 140: 844-855, 2006). The light source, filters and times of irradiation are described in Warpeha et al. ("Presence of adequate phenylalanine mediated by G-protein is critical for protection from UV radiation damage in young etiolated *Arabidopsis thaliana* seedlings: Plant Cell & Env., Accepted pending minor revisions). Heat is tested by rafting seedling in a water bath pre-set to 48° C. for 1 h. Salt is tested by applying 100 mM NaCl (final concentration) to the surface of the top agar.

The preparation of whole cell extracts from the areal portions of the seedlings for the quantification of Phe levels and PD1 activity levels is described in (Warpeha et al., Plant Physiol. 143:1590-1600, 2007). Phe concentration is determined by HPLC. PD1 activity in cell extracts is quantified as prephenate dehydratase activity via the spectrophotomotric monitoring of phenylpyruvate (product) levels in response to the addition of prephenate (substrate). Natural fluorescence of the cotyledons is visualized and quantitated by deconvoluting microscopy using a "DAPI-Long Pass" filter which allows excitation between 300-380 nm and emits with a cut-off below 400 nm.

Figures 24A, 24B, 24C:
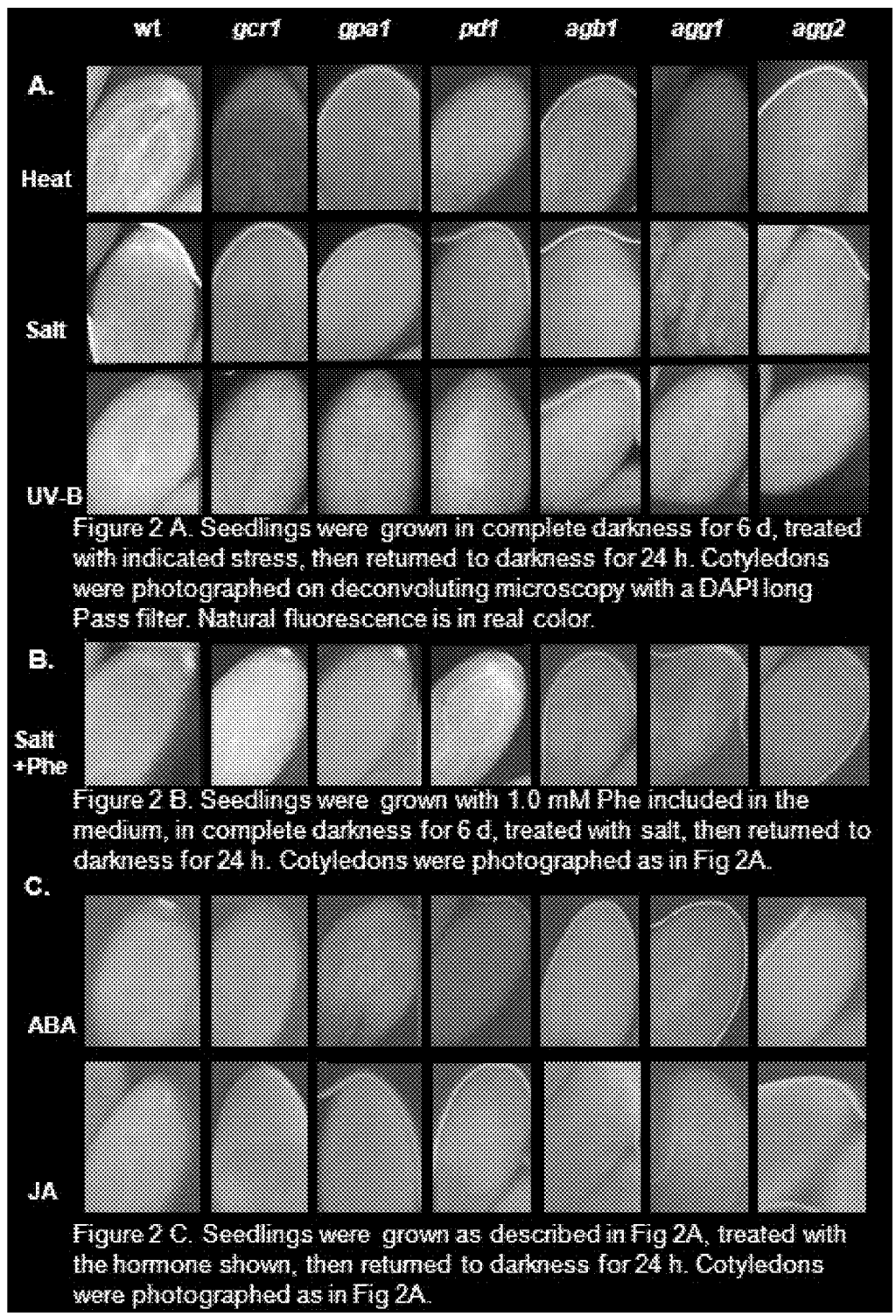
FIG. 24A is a series of photographs of seedlings that were grown in complete darkness for 6 days, treated with the indicated stress, then returned to darkness for 24 hours. Cotyledons were photographed on deconvoluting microscopy with a DAPI long Pass filter.
FIG. 24B is a series of photographs of seedlings that were grown in 1.0 mM Phe included in the medium, in complete darkness for 6 days, treated with salt, then returned to darkness for 24 hours. Cotyledons were photographed as in FIG. 24A.
FIG. 24C is a series of photographs of seedlings that were grown as described in FIG. 2A, treated with the hormone shown, then returned to darkness for 24 hours. Cotyledons were photographed as in FIG. 24A.
Figure 25:
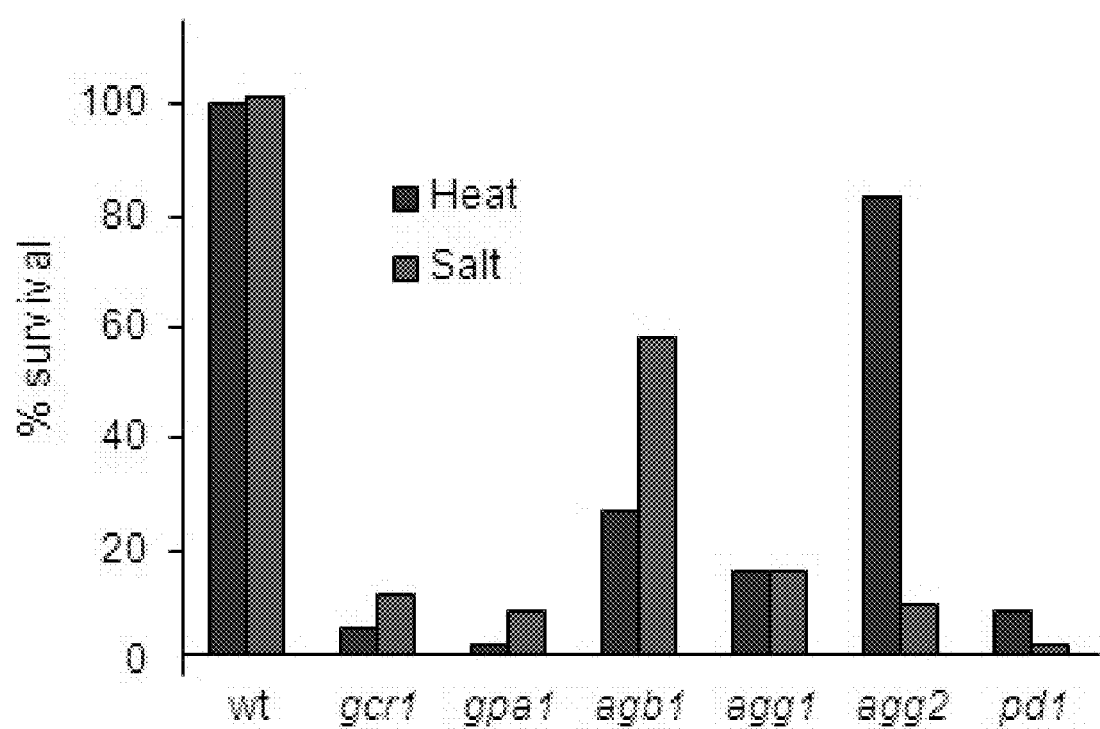
FIG. 25 is a graph showing results from an experiment in which seedlings were grown in complete darkness for 6 days, treated with heat or salt, then returned to darkness for 24 hours. Percent survival is shown.

It is expected that all three stressors will be determined to require all three signaling components in order to elicit the four assayed responses. Further, by measuring the levels of Phe and PD1 activity, whether or not PD1 is necessary is confirmed, as well as whether or not its activity is induced by all three stresses. FIGS. 24A and 25 present data measuring the levels of cotyledon abaxial surface fluorescence (for UV-B, salt and heat) and the ability of the seedlings to survive the stress (salt and heat), respectively. The data demonstrate that the ability of young etiolated seedlings to respond to UV-B, salt and heat stress is dependent upon GCR1, GPA1, and PD1.

The affirmation that young etiolated seedlings require GCR1, GPA1 and PD1 to respond to any or all of the three stressors (UV-B, stress and heat), and that the stresses lead to increased levels of Phe and PD1 activity, does not address the question of whether the response to the stress requires the additional Phe produced by the enhanced PD1 activity. If the Phe produced by activated PD1 is necessary for the ability of young etiolated seedlings to respond to UV-B, salt or heat stress, then it is possible that the addition of exogenous Phe (effectively cross feeding Phe) could restore a wild type response to GCR1, GPA1 and PD1 mutants when assayed for cotyledon fluorescence and the ability to survive sub-lethal levels of UV-C. To determine if exogenous Phe can restore wild type responses to GCR1, GPA, and PD1 mutants, 1 mM Phe is added to the top agar during planting and the experiment described above specifically testing for cotyledon surface fluorescence and the ability to survive sub-lethal levels of UV-C is repeated. Serine and L-Phe are used as negative controls in these assays.

It is expected that exogenous Phe will be found able to restore wt type responses to GCR1, GPA1 and PD1 mutants under all three stress conditions. The experiment does not address but does raise the interesting question of whether the additional Phe is necessary for the production of specific proteins and/or specific products of the phenylpropanoid pathway and of course what are the respective products. This question can potentially be addressed through the use of protein synthesis inhibitors, and single and combinatorial mutants in pal-1, 2 & 3.

FIG. 24B presents data demonstrating the restoration of surface fluorescence to GCR1, GPA, and PD1 mutants that have been treated for salt stress. The data confirm that Phe can restore the responses in the mutants to those observed for wild type seedlings.

To address whether the response to heat uses the same exact molecules of PD1, GPA1, or GCR1 as does UV-B, whether or not the response observed to two different stressors, for example heat and UV-B, when given together are additive such that the sum of the two stressors exceeds the arithmetic level of either alone or exceeds the saturation level is determined.

The experiment described above used to address whether or not GCR1, GPA1 and PD1 are required for young etiolated seedlings to respond to UV-B, salt or heat stress can be used (with and without supplemental phe) to test a range of dose/fluence for each of the three stresses. The assay is performed at 24 h. Both the broad-band and narrow band (317 nm) UV-B are tested for by decades between $10^{-1}$ and $10^5$ $\mu molm^{-2}$. Heat stress will range from 20° C. (room temp) to 60° C. (hottest temp recorded on land, Libya, 1922) by 10° intervals. The initial salt concentration series will range from 0 mM to 350 mM NaCl, by 50 mM increments.

Given that dose/fluence response curves are generally assumed to reflect the receptor and signal transduction mechanisms and not the biochemistry of the response itself, it is expected that for any given stress the fluence/dose response curves for the different assays should be similar. Given that Phe is both synthesized in response to stress and used as substrate for either protein and/or phenylpropanoid synthesis it is possible that it may not follow the pattern of the other assays.

It is possible that the GCR1, GPA1 and/or PD1 mutants may show a low level of response to the various stresses at fluence/dose responses that approximates saturation for wild type seedlings. This would suggest that a second signaling mechanism, independent of the GCR1-GPA1-PD1 mechanism is active at those doses/fluences.

If any two (or all three) stresses activate the same exact GCR1, GPA1, PD1 signal chain, then it is expected that the level of cotyledon fluorescence, Phe accumulation and PD1 activity will be identical at saturating doses/fluences regardless of the stress. If the levels of any of these parameters differ between any two or all three stresses, it would suggest that those stresses use independent signal transduction chains.

Wild type and mutant seedlings with and without Phe supplements are exposed to each stress at ¾ of saturation. Phe accumulation, survival to sub-lethal doses of UV-C and cotyledon fls will be measured at 0, ½, 1, 2, 6, 12, and 24 h post stress treatment. Data described herein indicate changes in surface fluorescence and Phe levels within minutes after UV-B treatment. If responses are observed within ½ h, a second time course is conducted focusing on the first 2 h post treatment. The PD1 activity tests are performed after the pre 2 h time course is complete.

It is possible that the Phe assay may exhibit a different time course then than the other assays. It is also possible that GCR1, GPA1, or PD1 mutants may exhibit a small response near maximal response times. It will be important to avoid such response times for future experiments.

To determine the range of times over which reciprocity exists for UV-B (assuming there is no interference from other signaling mechanisms), reciprocity is measured at ¾-saturation using delivery time ranging from 100 seconds to 10,000 seconds.

Genetic data, PD1 activity assays and phe-feeding experiments (FIGS. 24A, 24B, 25) suggest that young etiolated seedlings require GCR1, GPA1 and PD1, as well as PD1 activity and the Phe produced as a result of that activity in order to respond to UV-B, salt and heat stress If two stressors act through the same exact signal transduction chain, then the response to simultaneous exposure to both stresses, each at a dose/fluence of ¾-saturation, should not exceed the saturation level of response for either stress alone. If the simultaneous treatment results in a response that exceeds the level of saturation for either treatment, it implies that the two stresses act through separate signal transduction chains.

6-day old etiolated wt *Arabidopsis* seedlings are treated simultaneously (or as much as possible) with ¾-saturation levels of UV-B, salt and heat, alone and in pair-wise combinations. After 24 hrs (or a more suitable time as defined by the time-course data obtained from the experiment described above), cotyledon fluorescence, Phe accumulation and PD1 activity are measured. The response to sub-lethal doses of UV-C is not used as the assay itself (death) cannot exceed the saturation response of any individual stress already defined as 100% death.

There are two possible outcomes: an additive response that exceeds the saturation level for either stress alone, or a stop at or below normal saturation levels. If the effect of two stresses is additive this indicates the two stresses do not share the same exact signaling chain. If the results of the two stresses does not exceed the normal saturation level of either stress alone, the result would be consistent with the same exact signaling chain being used by the two stresses.

Irrespective of whether UV-B, salt and heat stress activate the same or different GCR1-GPA1-PDI signaling chains, and/or use the same Phe pool, it is unclear if the molecules made by the young etiolated seedling in response to one stress will protect the seedling from a subsequent exposure to the same or a different stress. Experiments are performed wherein UV-B, salt and heat are used in pair-wise combinations separated by the time it takes for the initial stress to reach ¾-maximal-response. In all cases the initial stress is delivered at threshold (as a control) and separately, at saturation for PD1 activity (presumably representing maximal Phe production). The second stress is delivered at saturation for killing in response to sub-lethal levels of UV-C. In all cases the ability of the seedlings to survive exposure to sub-lethal levels of UV-C is measured. Experiments are performed using wt seedlings as well as GCR1, GPA1 and PD1 mutants, on plates with and without 1 mM phe.

In the cases wherein the primary stress is delivered at threshold doses/fluences, it is expected that all of the seedlings will be killed by the sub-lethal levels of UV-C owing to the saturation dose/fluence of the second stress. In cases where the initial stress is delivered at saturating levels for PD1, the level of protect afforded by the compounds produced in response to the exposure of saturating levels of the first stress will be inversely reflected in the number of seedlings that die in response to exposure to sub-lethal levels of UV-C Loss of protection from the second stress in the GCR1, GPA1 and PD1 mutants serve as confirmation that some or all of the compounds necessary to protect against the second stress are produced as a result of excitation of the GCR1-GPA1-PD1 pathway. Restoration of the loss of protection in the GCR1, GPA1 and PD1 mutants grown on media supplemented with 1 mM Phe serves as confirmation that all or some of the compound necessary to confer protection against the second stress derive from Phe. Asymmetric protection, where stress 1 can protect the seedling from stress 2 but not visversa, suggests that different stress treatment can lead to the synthesis of different protective compounds. It is expected that exposure to any one stress would allow for protection from a second exposure that stress. If this is not the case it would suggest that the compounds made in response to the stress have a short half-life.

The data obtained as a result of the experiments described herein help to refine the model described herein of how young etiolated seedlings experience and respond to environmentally significant abiotic stressors. Understanding how young seedlings respond to, and protect themselves from, various abiotic stresses is critical given the crop losses due to abiotic stress. Given the changing nature of the environment it is also imperative that the relationships among the ways in which plants respond to different abiotic stress are understood.

Example 11

Analyzing Whether or not the Well-Known Stress Signaling Molecules ABA, JA, SA or Ethylene Excite The GCR1-GPA1-PD1 Cassette Stress responses often involve the phytohormones Abscisic Acid (ABA), Ethylene (ET), Jasmonic acid (JA), and/or Salicylic Acid (SA), either alone or in combination. Published data and the data described herein indicate that exposure of young etiolated seedlings to the abiotic stresses UV-B, heat, salt and UV-C results in the activation of the GCR1-GPA1-PD1 pathway. It has also been demonstrated that exposure to BL and UV-A light results in activation of the GCR1-GPA1-PD1 pathway. It is unlikely that all of these environmental signals interact directly or independently with GCR1 and it more likely that there are several different signaling intermediaries that lead to a common, or few structurally similar, GCR1 excitatory compound(s).

It has also been demonstrated that ABA, at physiologically relevant concentrations, can activate the GCR1-GPA1-PD1 and GCR1-GPA1-PRN1 pathways in young etiolated seedlings. It has been similarly shown that ABA is capable of eliciting the activity of GCR1-GPA1 mediated signaling pathways in *Arabidopsis*. Given that ABA can activate the GCR1-GPA1-PD1 signal transduction system and given that the phytohormones ABA, ET, JA, and SA are known to act as secondary messengers in most stress responses it seems reasonable to hypothesize that one or several of these phytohormones, including ABA, act as intermediaries between the various abiotic stresses and GCR1.

There is a need to determine if ABA, ET, JA, and/or SA, elicit the same responses as abiotic stress (cotyledon fluorescence, Phe synthesis, PD1 activity and protection against sub-lethal levels of UV-C) in young etiolated seedlings, and if so, are these responses dependent on the activity of the GCR1-GPA1-PD1 pathway, PD1 activity and Phe. If this is the case, it is then necessary to establish the relationship between the perception of each specific abiotic stress and each individual phytohormone with regard to the GCR1-GPA1-PD1 pathway.

The experiments described herein are designed to identify which of the four stress-related phytohormones have a role in the responses to UV-B, salt and/or heat stress in young etiolated seedlings. The initial experiments parallel those described above for examining the role of the GCR1-GPA1-PD1 signal transduction pathway in the response of young etiolated seedlings to various abiotic stressors but with ABA, ET, JA, or SA substituting for the abiotic stress. Those phytohormones that effectively mimic UV-B, salt and heat stress, in that they require GCR1, GPA1 and PD1, activation of PD1 activity and the Phe that result from that enhanced activity, are used for further analysis. The data shown in FIG. 24C indicate that ABA and JA have a potential role in mediating abiotic stress in young etiolated seedlings.

As for the responses to UV-B, salt and heat, it will be necessary to fully define the dose-response, time course and as possible reciprocity characteristics of the phytohormones responses. This information is then used to conduct experiments designed to determine which, if any, of the phytohormones act through the same exact GCR1-GPA1-PD1 signaling chains, or use the same Phe-pool, as do UV-B, salt and/or heat stress. The detailed characteristics are also used to determine if treatment of the young etiolated seedlings with the phytohormones acts to protect the seedlings from the effects of subsequent exposure to UV-B, salt and/or heat stress.

Phytohormones that mimic the various stressors, and are seen to act through the same exact GCR1-GPA1-PD1 signaling chain and use the same phe pool as does UV-B, salt or heat stress, and which can elicit a response in young seedlings that protects the seedling from the effects of a subsequent exposure to UV-B, salt and/or heat stress, will be assumed to act between that stress and GCR1 activation. Because of the difficulty of working with ET, the initial survey work is performed by using ACC (1-Aminocyclopropane-1-Carboxylate Synthase) in the media which in turn leads to the production of ET by the seedling (Kieber et al., Cell 72:427-441, 1993).

The experiments described above for examining if GCR1, GPA1 and PD1 are required for young etiolated seedlings to respond to UV-B, salt or heat stress are performed but with ABA, ACC, JA and SA substituting for UV-B, salt and heat. For these experiments, ABA is tested at 1.0 µM dissolved in ethanol and applied as an atomized mist. ACC is added to the bottom agar at 10 µM. JA is tested at 500 µM dissolved acetone and applied as an atomized mist. SA is used at 1.0 mM as a spray. The data described herein suggest that both ABA and JA have a role in mediating abiotic stress in young etiolated seedlings.

The data in FIG. 24B shows cotyledon flourescence assays for wt and GCR1, GPA1, and DP1 T-DNA insertion, knock-out mutants treated with 1.0 µM ABA and 500 µM JA. Note that the response pattern is identical to that of UV-B, salt and heat.

Whether or not the additional Phe produced by activated PD1 is required for young etiolated seedlings to respond to ABA, ACC, JA or SA is examined. The experiments described above for analyzing if the additional Phe produced by activated PD1 required for young etiolated seedlings to respond to UV-B, salt or heat stress are performed but with ABA, ACC, JA and SA substituting for UV-B, salt and heat.

What the dose/fluence-response, time-course, and reciprocity characteristics of the phytohormones mediated activation of the GCR1-GPA1-PD1 pathway in young etiolated seedlings are is examined. The experiments described above for analyzing the dose/fluence-response, time course and reciprocity characteristics of the stress mediated activation of the GCR1-GPA1-PD1 pathway in young etiolated seedlings are performed but with ABA, ACC, JA and SA substituting for UV-B, salt and heat.

Whether or not ABA, ACC, JA and/or SA, activate the same exact GCR1-GPA1-PD1 signal transduction chain and/or rely on the same pool of Phe as do UV-B, salt and heat is examined. The experiments described above for analyzing if UV-B salt and/or heat activate the same exact GCR1-GPA1-PD1 signal transduction chain and/or rely on the same pool of Phe are performed, except that rather then test two abiotic stresses, pair-wise combinations of the three abiotic stressors (UV-B, salt and heat) with those phytohormones determined in the experiment described above to have a potential role in mediating abiotic stress responses in young etiolated seedlings are tested.

Whether or not exposure to ABA, ACC, JA and/or SA make the seedling resistant to the effects of exposure to UV-B, salt or heat stress is examined. The experiments described above for analyzing if exposure to one stress makes the seedling more resistant to subsequent exposure to the same stress and/or to a different stress are performed, except that rather then use an abiotic stress as the initial treatment, those phytohormones determined in the experiment described above to have a potential role in mediating abiotic stress responses in young etiolated seedlings are tested for their ability to make the seedling resistant to the effects of exposure to UV-B, salt or heat stress. The experiments described herein test the model described herein and contribute to the building of a large signaling network encompassing stress, phytohormones and G-protein mediated signaling.

Example 12

Analyzing if AGB1, AGG1, and AGG2 and Other Characterized G-Protein Associated Proteins have a Role in the GCR1, GPA1, PD1 Mediated Response of Young Etiolated Seedling to Exposure to UV-B, Salt and/or Heat Stress The *Arabidopsis* genome codes for one Gα(GPA1), one Gβ (AGB1) and two Gγ (AGG1 and AGG2) subunits. CHIP and published expression data all suggest that all 4 genes are expressed in the young etiolated seedlings (Zimmerman et al., Plant Physiol. 136:2621-2632). The presence of 2 Gγ subunits suggests two heterotrimeric G-proteins with potentially different functions.

Recent reports from several labs indicate that plant G-protein subunits may function in a more independent manner then their animal counterparts. GPA1 has a basal GTPase activity suggesting that it may not need to interact with a 7-TMS (e.g. GCR1) to become active. AGB1 knock-out mutants do not phenocopy AGG1/AGG2 double mutants as would be expected given the tight linkage observed between Gβ and Gγ subunits observed in animal systems. In addition to the canonical subunits, *Arabidopsis* also codes for at least three so-called extra-large Gα subunits (Pandey et al., Plant J. 55:311-322, 2008; Ding et al., Plant J. 53; 248-263, 2008). Given the variations in plant G-protein subunit activities, and the specific occurrence of two Gγ subunits, it is important that we understand the relationship of AGB1, AGG1 and AGG2, to the GCR1-GPA1-PD1 pathway.

Several groups have reported on Gα interacting proteins representing potential effectors. T-DNA insertion mutants in the genes coding for these proteins are surveyed to determine if any have a role in the response of young etiolated seedlings to abiotic stress (Table I). PRN1, representing, a potential quercetinase as discussed above.

The experiments in this section are designed to identify G-protein associated proteins other then GPA1, GCR1 and PD1 that a have a role in how young etiolated seedlings respond to UV-B, salt and/or heat stress. Those proteins that affect the activity of the GCR1-GPA1-PD1 pathway are especially interesting. A special case, PRN1, is discussed in Example 13.

Experiments similar to those described above for analyzing if GCR1, GPA1 and PD1 are required for young etiolated seedlings to respond to UV-B, salt or heat stress are used but with T-DNA insertion, knock-out mutants in the various GPA1 associated proteins (AGB1, AGG1, AGG2, XLG1, XLG2, XLG3, RGS and potential effectors; see Table 6) substituting for GCR1, GPA1 and PD1. Mutants are tested for cotyledon fluorescence, the ability to survive exposure to sub-lethal levels of UV-C, and levels of Phe and PD1 activity in cell free extracts.

Mutants exhibiting a response pattern similar to GPA1 mutants in response to exposure to UV-B, salt and heat stress and whose response can be restored to wild type by the addition of exogenous Phe are further tested to determine their response to those phytohormones identified as intermediaries between abiotic stress and GCR1. Those mutants continuing to exhibit GPA1 like responses are fully characterized (dose/fluence response, time course and as possible reciprocity). Data described herein (shown in FIGS. 24A, B, C and 25) suggest that AGB1 and AGG1 have a significant role in the response to abiotic stress and that AGG2 may not.

Whether or not AGB1, AGG1, AGG2, XLG1, XLG2, XLG3, RGS and other characterized G-protein associated proteins required for young etiolated seedlings to respond to UV-B, salt or heat stress is examined. The experiment itself is identical to that described above for analyzing if GCR1, GPA1, and PD1 are required for young etiolated seedlings to respond to UV-B, salt or heat stress are performed but with T-DNA insertion knock-out mutant lines in AGB1, AGG1, AGG2, XLG1, XLG2, XLG3, RGS and other genes coding for G-protein associated proteins, substituting for mutants of GCR1, GPA1 and PD1. The specific T-DNA insertion mutant lines to be used are indicated in Table 6. Note that two different lines are used for each gene. All of the lines indicated have been identified as so-called knock-out lines with the exception of the XLG's.

The presence of 2 Gγ subunits allows for five potential outcomes, for each stress tested. 1) insertions in AGG1 but not AGG2 affect the stress responses 2) insertions in AGG2 but not AGG1 affect the stress responses 3) neither AGG1 nor AGG2 effect the stress responses, 4) insertions in both AGG1 and AGG2 effect the stress responses, and 5) there is no discernable pattern. This is further complicated by the possibility that UV-B, salt and heat stress may differ in their use of AGG1 and AGG2.

In the first two cases it is fairly certain that the mutant exhibiting the loss of stress induced responses represents the Gγ subunit active in that stress pathway. The third case, wherein single mutants of either AGG1 or AGG2 alone show no phenotype, suggests that both AGG1 and AGG2 can act in this pathway, each complementing the loss of the other, or that neither has a role in this pathway. These two possibilities can be discriminated by testing an AGG1AGG2 double mutant. Loss of response in the double mutant would indicate the former possibility; no loss of responses in the double mutant would imply the later possibility. The fourth possibility, loss of induced responses for both subunits suggests that both are required for the signaling network to function. Possibilities include a single complex that requires both AGG1 and AGG2 to function. Given the way Gγ works in other organisms, it is not likely. A second, more likely scenario is that neither AGG1 nor AGG2 alone produces enough protein to allow for normal signaling responses. Testing the single mutants at different times, or dose of stress might reveal conditions under which either AGG1 or AGG2 alone can allow for a normal response. In this case an AGG1AGG2 double mutant would remain unresponsive at all times and doses tested.

FIGS. 24A and 25 present data measuring the levels of cotyledon adaxial surface fluorescence (for UV-B, salt and heat) and the ability of the seedlings to survive the stress (salt and heat). The data demonstrate that AGB1 is necessary for young etiolated seedlings to respond to UV-B, salt and heat stress. The data suggest that AGG1 is solely responsible for heat stress responses and that while AGG1 has a role in UV-B and salt stress, AGG2 may also have a role. This experiment is performed with the AGG1AGG2 double mutant.

Whether or not the additional Phe produced by activated PD1 is required for young etiolated seedlings to respond to UV-B, salt or heat stress is examined as described above. In these experiments, T-DNA insertion knock-out mutant lines in AGB1, AGG1, AGG2, and other, appropriate G-protein associated proteins substitute for mutants of GCR1, GPA1 and PD1. The data presented in FIG. 2B indicate that exogenous Phe can restore wild type responses to AGB1 and AGG1 mutants, suggesting that the AGB1 and AGG1 have a role in the GCR1-GPA1-PD1 signaling pathway and the production of Phe as a result of the activation of that pathway.

Whether or not GCR1, GPA1 & PD1 are required for young etiolated seedlings to respond to ABA, ACC JA, or SA is examined as described above. In these experiments, T-DNA insertion knock-out mutant lines in AGB1, AGG1, AGG2, and other, appropriate G-protein associated proteins substitute for mutants of GCR1, GPA1 and PD1. The data presented in FIG. 24C for cotyledon fluorescence indicate that AGG2 has no role in either ABA or JA signaling in this system consistent with the data for heat and salt stress. JA seems to require AGG1 but not AGB1, while ABA seems only to need AGG1.

The dose/fluence-response, time-course, and reciprocity characteristics for UV-B, salt and heat mediated activation of the GCR1-GPA1-PD1 pathway in young etiolated seedlings are examined as described above. In these experiments, T-DNA insertion knock-out mutant lines in AGB1, AGG1, AGG2, and other, appropriate G-protein associated proteins substitute for mutants of GCR1, GPA 1 and PD1.

The experiments described herein and resulting data will provide a strong tool for assessing the various roles of the G-protein subunits and other associated proteins in a single, relatively simple, well defined, signaling transduction system.

Example 13

Analyzing if PRN1 Acts as a Quercetinase and if the GCR1-GPA1-PRN1 Signaling Pathway has a Regulatory Role in Effecting the Products of the GCR1-GPA1-PD1 Signaling Pathway Young, etiolated, wild type seedlings are resistant to UV-B, salt, and heat at levels reported to cause stress in adult plants. This implies that protection factors are present in young etiolated seedlings and that the factors need to have been synthesized during embryo/seed development and stored until needed, and/or synthesized in the etiolated seedling itself. Extensive analysis of the *Arabidopsis* seed indicates that flavonols and other phenylpropanoids are in abundance, and that Phe, the compound from which they derive is only present at low levels.

Published data and the data described herein indicate that the stress resistance exhibited by young etiolated seedlings requires GCR1, GPA1, and PD1, PD1 activity and the Phe that derives from that activity. It is also known that the system is capable of turning on immediately in response to exposure to heat, UV-B, and salt (FIG. 24), stress related phytohormones (ABA and JA; FIG. 24) and UV and BL (Warpeha et al., Plant Physiol. 140:844-855, 2006) and that exogenously added Phe is immediately used by the etiolated, un-treated seedlings to synthesize compounds from the phenylpropanoid pathway, indicating that all of the enzymatic activities of the pathway are present and active.

These data suggest that the stress-responsive GCR1-GPA1-PD system is a rapid-response systems and therefore might actually be constitutively "on" at a low level. The protective factors would be made and subsequently destroyed if not utilized. When called for, the destruction would stop and the synthesis would increase, resulting in a large and rapid accumulation of the protection factors. The SAURS (small up regulated auxin responders) are one example of a gene family that is so-regulated. The genes are constitutively transcribed producing transcript. The RNA produced is rapidly degraded by an RNase activity that itself is the substrate of a specific protease that cleaves the RNase. Auxin activates the protease, in turn it degrades the RNase and the SAUR transcripts rapidly accumulate to very high levels.

There are a number of phenylpropanoid compounds that have been proposed to absorb harmful UV-B irradiation. The specific flavonol quercetin has been identified as the main inducible pigment for UV-protection in many plant species, and likely to be very important in the very young seedling due to the reserves of quercetin in the *Arabidopsis* seed. Quercetin is not only an efficient absorber of UV-B, but also has strong anti-oxidant capabilities, likely to assist the seedling in resisting the damaging effects of other types of stress.

Given the levels of stress protection already present in etiolated young seedlings, and the fact that providing exogenous Phe rapidly increases the level of stress resistance, it is determined if the etiolated seedling rapidly turns over quercetin until exposure to stress. This would provide a constitutive level of protection to the developing seedlings and a means of rapidly increasing stress protection as needed. As such in a stress situation, it might be expected that the GCR1-GPA1-PD1 pathway could in some manner both turn off the destabilization of quercetin, and at the same time act to increase the rate of synthesis of quercetin. The later is likely to be achieved via the stress induced activation of the GCR1-GPA1-PD1 pathway leading to the rapid synthesis of Phe followed by the rapid synthesis of quercetin via the flavanol branch of the polypropanoid pathway.

Several recent reports indicate that Pirin, in addition to being an NFY interacting protein, can also act as a quercetinase in animal and bacteria cells. There is over 55% amino acid identity and over 65% similarity between the *Arabidopsis*, human and *E. coli* pirins. It has been reported that PRN1 is expressed in etiolated *Arabidopsis*, has the ability to interact with GPA1, functions as a GCR1-GPA1 effector regulating ABA and BL mediated gene expression via its interaction with NFY (A5, B9, C4) and the CCAAT box located in several genes (Warpeha et al., Plant Physiol. 143:1590-1600, 2007).

It is possible that *Arabidopsis* PRN1 acts as a quercetinase in etiolated tissue, actively degrading the quercetin made in the etiolated seedling and that activation of the GCR1-GPA1 pathway via abiotic stress (UV-B, heat, salt), stress related phytohormones (ABA, JA) or pre-stress activators (BL, UV-A) allows an interaction between activated GPA1 and PRN1 that effectively turns off the PRN1 quercetinase activity. This would allow PRN1 to interact with NFY and carry out its role as a transcriptional activator, and at the same time allowing for a rapid increase in quercetin fueled by the Phe produced by the interaction between the activated GPA1 and PD1 (see FIG. 23). This is a testable model.

If PRN1 can act as a quercetinase in etiolated *Arabidopsis* seedlings is determined and if so, if that activity is inhibited through interaction with activated GPA1 is determined. Assuming that PRN1 is found to have quercetinase activity in vitro, and that its activity is regulated through interaction with GPA1, if PRN1 acts as a quercetinase in vivo and if that activity is regulated through activation of the GCR1-GPA1 pathway is determined. The levels of quercetin and quercetinase activity in cyptoplasmic extracts of young etiolated wild type and T-DNA insertion knock-out mutants in GCR1, GPA1 and PRN1 are examined, before after exposure to UV-B, salt and heat stress, and the appropriate stress related phytohormones as determined above.

Whether or not in vitro synthesized/purified PRN1 has quercetinase activity and if so whether or not it is regulated through interaction with activated GPA1 is examined. PRN1 is synthesized and purified as described in (Lapik et al., Plant Cell 15:1578-1590, 2003). The purified PRN1 is assayed for quercetinase activity according to (Adams and Jia, J Biol Chem 280:28675-28682, 2005). Whether or not the interaction between purified PRN1 and activated GPA1 affects the quercetinase activity in a manner identical to that used by Warpeha et al. (Plant Physiol. 140:844-855, 2006) is determined to determine the effects of GPA1 and PD1 interaction on PD1 activity. Based on the strong homology exhibited between the *Arabidopsis*, human and *E. coli* enzymes it is very likely that PRN1 will act as a quercetinase.

Whether or not the cytoplasm of young etiolated seedlings contains a quercitnase activity and if so what the relationship is of that activity to GCR1, GPA1, PRN1, stress and stress related phytohormones is determined. Six-day-old etiolated wt and T-DNA insertion knock-out mutants for GCR1, GPA1, and PRN1, treated with UV-B, salt and heat or left untreated, are returned to darkness and subsequently assayed for cytoplasmic levels of quercetin (via HPLC), and for quercetinase activity as described (Adams and Jia J. Biol. Chem. 280: 28675-28682, 2005). Quecertin and quercetinase activity are tested for at 4, 8 and 16 hrs after the stress treatments.

Per the working model described herein, it is expected that low levels of quercetin and high levels of quercetinase activity will be found in etiolated wt seedlings and that these would invert upon exposure to stress such that the level of quercetin increased while the level of quercetinase activity decreased. For mutants in GCR1 and GPA1, it is expected that the etiolated seedlings will resemble wt in that the cyptoplasmic levels of quercetin would be low and level of quercetinase activity would be high. However, upon stress exposure, it is not expected that an increase in quercetin levels nor a decrease in the levels of quercetinase activity will be observed. For the PRN1 mutants, it is expected that moderate levels of quercetin will be seen, depending on how high the basal dark level of synthesis is, and low levels of quercetinase activity. Exposure to stress should result in a rapid increase in the level of quercetin with no change in quercetinase activity.

Figure 26A:
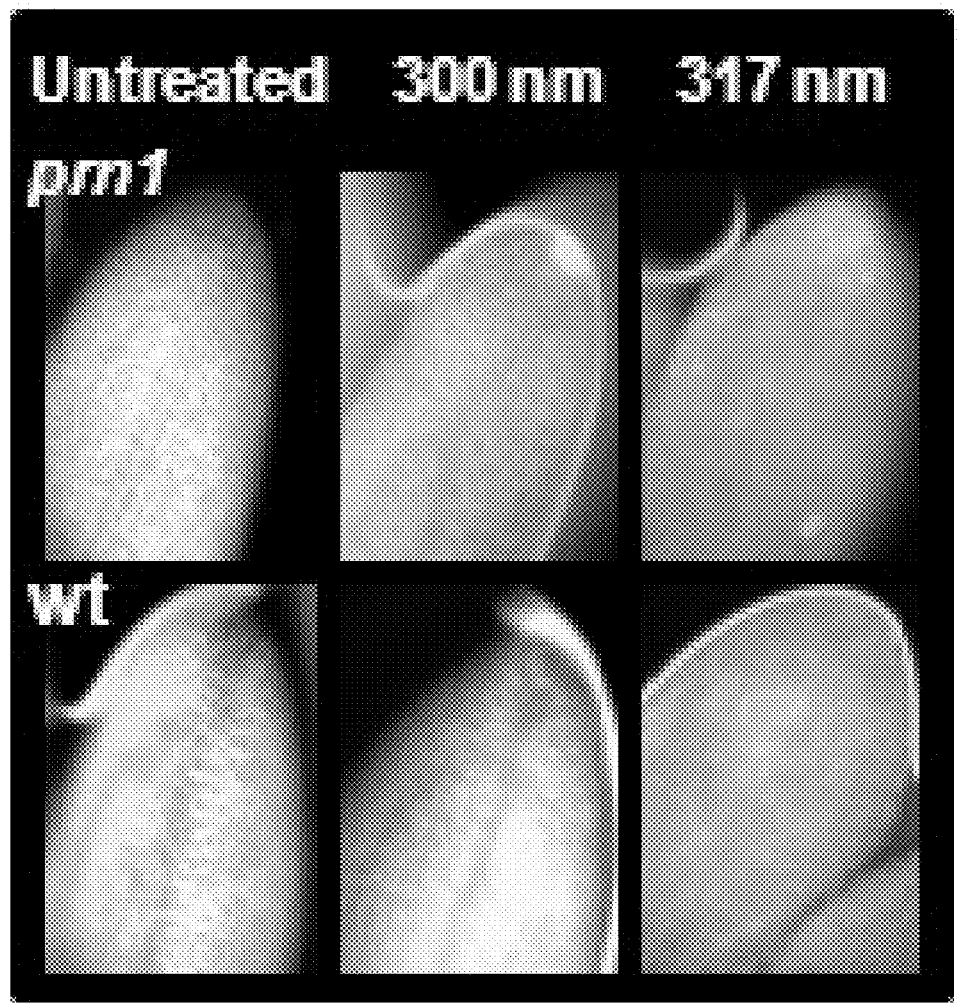
FIG. 26A is a series of photographs of seedlings that were grown in complete darkness for 6 days, treated with UV-B wavelengths, then returned to darkness for 24 hours. Seedlings were photographed using deconvoluting microscopy.
Figure 26B:
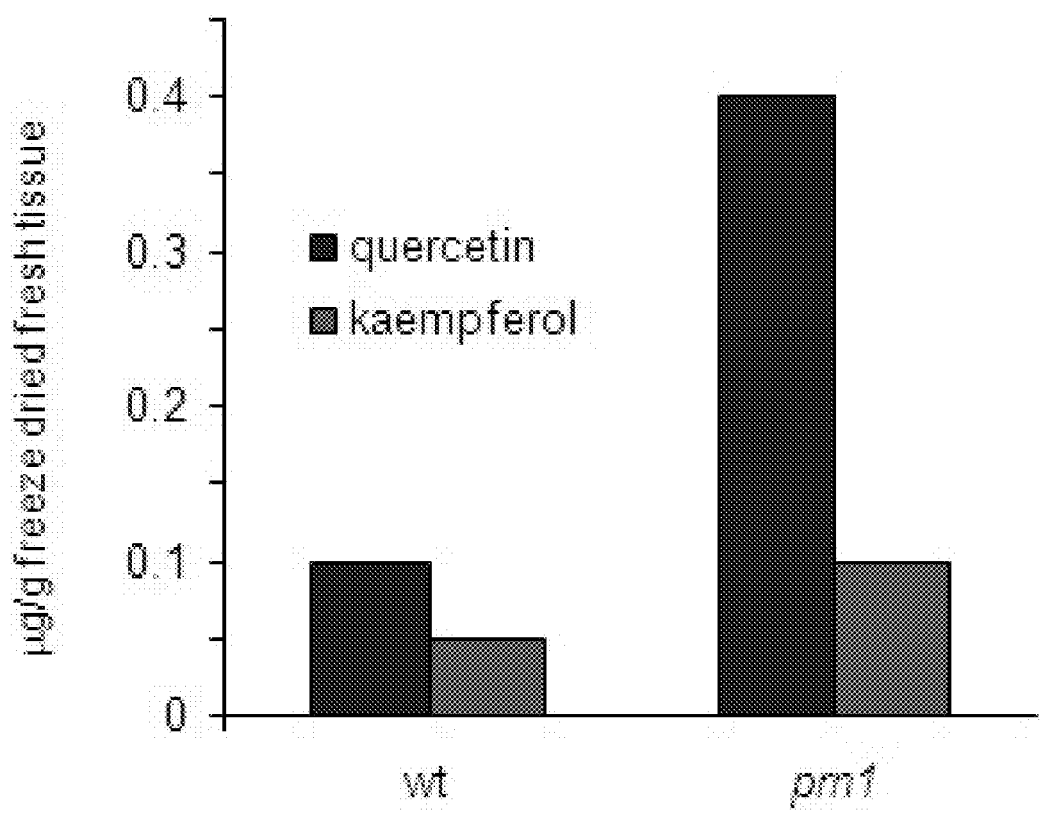
FIG. 26B is a graph showing results from an experiment in which seedlings were grown in complete darkness for 6 days, treated with UV-B (317 nm for 11 min=$10^4$ μmolm$^{-2}$), then returned to darkness for 24 hours. Aerial portions of seedlings were frozen in liquid nitrogen in darkness, then assessed by HPLC to quantify quercetin & kaemperoi in wt and prn1 mutants against purified standards.

The data shown in FIGS. 26A & B strongly indicate that etiolated wt seedlings exhibit low levels of quercetin and kempherol (a closely related compound). The data also clearly indicate that those levels are greater in the PRN1 mutants consistent with PRN1 acting as a quercetinase.

The data obtained as a result of the experiments described herein will help to refine an understanding of flexibility in the G-protein environment, and an understanding of how to piece together a signaling pathway in order to broaden the understanding of signaling in general.

Upon reviewing the aforementioned embodiments, it would be evident to an artisan with ordinary skill in the art that said embodiments can be modified, reduced, or enhanced without departing from the scope and spirit of the claims described below. For example, plants can be protected from stressors in addition to heat, ultraviolet radiation, and salt (i.e., any stressor a plant may be subjected to).

Example 14

Specific Mutant Seedlings Exposed to UV-B Radiation Demonstrate Variation in Response to Fungus—Overproduction of Quercetin can Deter Fungal Infection We have shown that very young seedlings are particularly sensitive to UV-B, and that exposure to even small amounts of UV-B during early seedling development effects germination, greening, hypocotyl length, cell and tissue morphology in the young seedling as well as seed set, pod number in the adult plant. The inclusion of Phe in the planting media can prevent these effects of exposure of young seedlings abiotic stressors of all kinds including but not limited to salt, heat, UV radiation, high light, and biotic stressors such as hormones and products of organisms (Warpeha et al., 2006; 2007). Mutants of the phenylalanine biosynthesis and regulation pathway can alter the quantities of Phe and phenylpropanoids available to the plant for defense responses.

Specific mutants involved in Phe regulation were grown for 7 d in complete darkness along with wild type to examine the products of the Phe pathway and effects of infection and affects of fungus. pd1 mutants (produce little or no Phe in dark grown conditions hence no phenylpropanoids), prn1 produce excessive phenylpropanoids particularly quercetin and wild type are unaffected in Phe production. Six days after planting plants were surface inoculated with 1 colony of Cryptococcus fungus of 1 mm in diameter. Plants were returned to darkness for 24 h or irradiated with 317 nm and returned to darkness for 24 h then photographed on deconvoluting microscopy for effects of fungus. Data is shown in FIG. 27. Wild type mutants produced infection but the infection was limited to the cotyledon tip and stress signaling/pathway allowed for a walling off of the infection limited to 3 mm radius from initial wipe/inoculation. Other pigments and products appeared as normal wild type treated with 317 nm or Untreated (Warpeha et al., Plant Cell and Environ. Vol. 31:1756-1770, 2008). pd1 mutants treated with fungus were 21.2±0.2% shorter than wild type Untreated and treated with 317 nm, respectively where the cotyledon was only 64.8+4.9% of the size of the equivalent wild type treatment and no pigments were produced indicating that the lack of Phe in these seedlings was causing the plant to experience more insult stress to the cotyledon and seedling itself. prn1 mutants on the other hand appeared completely uninfected—no reduction or changes in growth or cotyledon expansion were observed compared to wild type untreated. The pigments produced in prn1 cotyledons compared to wild type cotyledons are in excess (quercetin is increased four-fold), and this may explain the complete failure of the fungus to be able to successful infect the plant cells in the 24 h period post-inoculation compared to wild type. These data indicate that biosynthesis of Phe and its downstream products are utilized for plant defense against fungal infection.

Example 15

Germinating Soybean Seedlings Exposed to UV-B Radiation Demonstrate Increased Predation that can be Reduced by Phe We have shown that very young seedlings are particularly sensitive to UV-B, and that exposure to even small amounts of UV-B during early seedling development effects germination, greening, hypocotyl length, cell and tissue morphology in the young seedling as well as seed set, pod number in the adult plant. The inclusion of Phe in the planting media can prevent these effects of exposure of young seedlings presumably by allowing the plant to produce compounds from the phenylpropanoid pathway that help screen the harmful UV-B.

As Phe is the starting substrate of the phenylpropanoid pathway it may be that inclusion of Phe in the growth media of young seedlings allows for the synthesis of many phenylpropanoids in addition to those that can act as UV-B screening pigments, and thereby prevent the deleterious effects other abiotic and biotic stress. To test this hypothesis we planted sets of seeds of Harosoy dense and Harosoy glabrous. Planting media for one set of plants of each isoline was supplemented with 1 mM final concentration of Phe. Three d after planting, germinating sets of seedlings were irradiated with a low fluence pulse of 300 nm (i.e. an abiotic stress), or no light (Untreated), then transplanted outside to grow in natural conditions for 21 d during the normal growing season. A random planting pattern for was generated for the six One leaf from the first set of leaves and one leaf (the middle of the trifoliate) from the second set of leaves was harvested on day 21. These leaves were each weighed directly (fresh weight) and scanned to have a pictorial representation of the experienced damage as shown in FIG. 28. The resulting leaf masses and morphologies suggest specific predation and the organisms that were directly found on the leaves in the 2-3 weeks period giving the appearance as shown in the Figures were confirmed as Japanese beetles. Comparison among the six variations indicates predation mainly on the glabrous (hairless) plants. Seedlings germinated in media with Phe experienced less predation.

OTHER EMBODIMENTS

Any improvement may be made in part or all of the compositions and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A plant seed coated with a composition comprising phenylalanine in an amount sufficient to protect the plant seed and a plant that grows from the plant seed from damage from a stressor selected from the group consisting of: UV radiation, arthropods and nematodes.

2. The plant seed of claim 1, wherein the plant seed is a soybean plant seed.

3. The plant seed of claim 1, wherein the composition further comprises gelatin.

\* \* \* \* \*